United States Patent [19]

Lee et al.

[11] Patent Number: 5,436,233
[45] Date of Patent: Jul. 25, 1995

[54] 4-AMINOQUINAZOLINE DERIVATIVES

[75] Inventors: Sung J. Lee, Clarks Summit, Pa.;
Yoshitaka Konishi, Osaka, Japan;
Orest T. Macina, Clarks Summit, Pa.;
Kigen Kondo, Osaka, Japan; Dingwei T. Yu, Easton, Pa.

[73] Assignee: Ono Pharmaceutical Co., Ltd., Osaka, Japan

[21] Appl. No.: 154,518

[22] Filed: Nov. 19, 1993

Related U.S. Application Data

[63] Continuation-in-part of Ser. No. 76,431, Jun. 14, 1993, abandoned, which is a continuation-in-part of Ser. No. 913,473, Jul. 15, 1992, abandoned.

[51] Int. Cl.⁶ .................. C07D 239/95; C07D 215/16; A61K 31/395; A61K 31/505
[52] U.S. Cl. ...................... 514/63; 514/212; 514/218; 514/241; 514/259; 540/575; 540/600; 544/180; 544/284; 544/293
[58] Field of Search ....................... 544/180, 284, 293; 540/575, 600; 514/63, 212, 218, 241, 259

[56] References Cited

U.S. PATENT DOCUMENTS

| | | | |
|---|---|---|---|
| 3,324,122 | 6/1967 | Burch | 544/284 |
| 3,705,898 | 12/1972 | Alaimo | 544/293 |
| 3,753,981 | 8/1973 | Breuer et al. | 514/259 |
| 3,772,295 | 11/1973 | Robba et al. | 514/259 |
| 3,772,295 | 11/1973 | Robba et al. | 544/284 |
| 3,819,628 | 6/1974 | Simpson | 514/259 |
| 3,971,783 | 7/1976 | Barnish et al. | 514/259 |
| 4,055,642 | 10/1977 | Nesvadba et al. | 544/293 |
| 4,060,615 | 11/1977 | Matier et al. | 514/259 |
| 4,269,834 | 5/1981 | Nauta | 514/259 |
| 4,306,065 | 12/1981 | Chen | 514/259 |
| 4,694,000 | 9/1987 | Timmerman et al. | 514/187 |
| 5,047,404 | 9/1991 | Coates et al. | 514/259 |

FOREIGN PATENT DOCUMENTS

| | | |
|---|---|---|
| 0135975 | 4/1985 | European Pat. Off. . |
| 0395328 | 4/1990 | European Pat. Off. . |
| 0371731 | 6/1990 | European Pat. Off. . |
| 2081456 | 12/1971 | France . |
| 2102221 | 4/1972 | France . |
| 2310756 | 12/1976 | France . |
| 58-172379 | 10/1983 | Japan . |
| 578556 | 8/1976 | Switzerland . |
| 1199768 | 10/1967 | United Kingdom . |
| 2002746 | 2/1979 | United Kingdom . |
| 461621 | 11/1975 | U.S.S.R. . |
| 89-05297 | 6/1989 | WIPO . |
| 9307124 | 4/1993 | WIPO . |

*Primary Examiner*—Mukund J. Shah
*Assistant Examiner*—Matthew V. Grumbling
*Attorney, Agent, or Firm*—Stevens, Davis, Miller & Mosher

[57] ABSTRACT

The compounds of the formula:

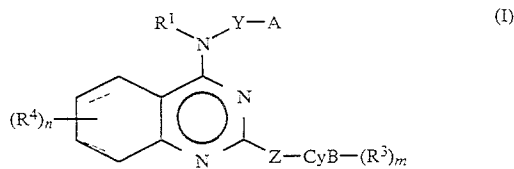

wherein $R^1$, Y, A, $R^4$, n, Z, CyB, $R^3$, and m are defined in the specification.

26 Claims, No Drawings

4-AMINOQUINAZOLINE DERIVATIVES

CROSS REFERENCE TO RELATED APPLICATIONS

This application is a continuation-in-part of our co-pending application Ser. No. 08/076,431 filed Jun. 14, 1993. now abandoned, which is a continuation-in-part of our application Ser. No. 07/913,473 filed July 15. 1992, which is now abandoned.

FIELD OF THE INVENTION

The present invention relates to novel 4-aminoquinazoline derivatives. More particularly, this invention relates to:

(i) 4-aminoquinazoline derivatives of the following formula:

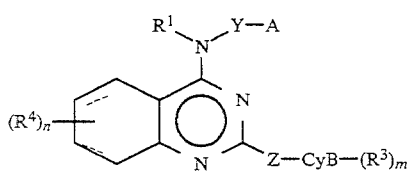

wherein all of the symbols have the same meanings as described hereinafter, and the pharmaceutically acceptable acid addition salts thereof, the pharmaceutically acceptable salts thereof, and the hydrates thereof, which have inhibitory activity on cyclic guanosine 3',5'-monophosphate phosphodiesterase, or additionally on thromboxane A2 synthetase, (ii) processes for the preparation thereof, (iii) inhibitors of cyclic guanosine 3',5'-monophosphate phosphodiesterase, or additionally of thromboxane A2 synthetase containing them, and (iv) methods of prevention and treatment of symptoms and diseases of mammals, including humans, by administering an effective amount of the compounds of the formula (I), the pharmaceutically acceptable acid addition salts thereof, the pharmaceutically acceptable salts thereof, and the hydrates thereof, to the patient to be treated.

BACKGROUND OF THE INVENTION

Cyclic guanosine 3',5'-monophosphate (abbreviated as cGMP hereafter) was found in urine in rats by D. F. Ashman in 1963. Till now, it has been known that cGMP is distributed broadly in tissues of many animals including human beings. cGMP is biosynthesized from guanosine triphosphate (GTP) by the action of guanylate cyclase.

cGMP has been experimentally confirmed to have various physiological activities. For example, cGMP induces the relaxation of heart muscle and of smooth muscle. Further, it is related to the formation of neuronal synapses, and it acts as a trigger of cell proliferation and it induces the proliferation of lymphocyte.

cGMP is metabolized to physiologically inactive 5'-GMP by the action of cGMP phosphodiesterase (abbreviated as cGMPoPDE hereafter).

Accordingly, the inhibition of the action of cGMP-PDE is considered to be useful for the prevention and-/or treatment of diseases induced by enhancement of the metabolism of cGMP, such as hypertension, heart failure, myocardial infarction, angina, atherosclerosis, cardiac edema, renal insufficiency, nephrotic edema, hepatic edema, asthma, bronchitis, dementia, immunodeficiency, pulmonary hypertension.

On the other hand, thromboxane A2 (abbreviated as TXA2 hereafter) was found as a constituent of the arachidonate cascade, in platelets by M. Hamberg in 1975. TXA2 is biosynthesized from arachidonic acid released from cell membrane via prostaglandin G2 and prostaglandin H2, and rapidly metabolized to inactive thromboxane B2. TXA2 is known to induce platelet aggregation and to contract smooth muscle, particularly blood vessel muscle and bronchial muscle. TXA2 synthetase was isolated and purified from microsome in platelets.

Accordingly, the inhibition of TXA2 synthetase decreases the biosynthesis of TXA2, and is useful for the prevention and/or treatment of inflammation, hypertension, thrombosis, arteriosclerosis, cerebral apoplexy, asthma, myocardial infarction, cardiostenosis, cerebral infarction, etc.

RELATED ARTS

Up to now, some compounds have been known as cGMP-PDE inhibitors, for example,

Zaprinast

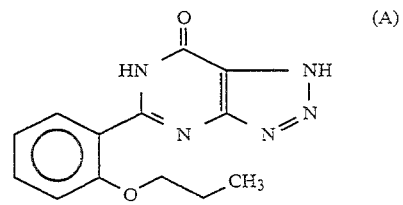

AR-L57

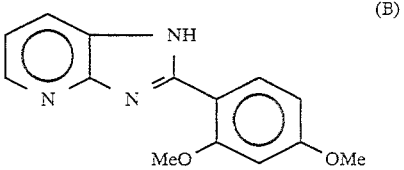

MY-5445

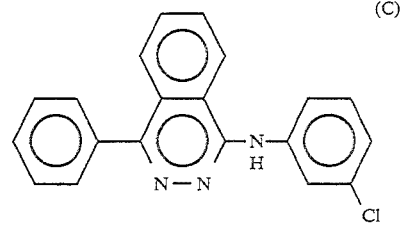

Many compounds derived from the above lead compounds have been proposed and many patent applications relating to those have been filed. For example, as derivatives of Zaprinast, compounds wherein the 1H-1,2,3-triazole skeleton is replaced by various other hetero cycles (see U.S. Pat. No. 5,047,404), those wherein the triazole is replaced by a benzene ring (see EP-371731), and those wherein the triazole is eliminated, i.e. those having only the pyrimidine skeleton (see EP-395328), have been proposed. The above mentioned compounds always contain an oxo group at the 4th position of the pyrimidine skeleton. The compounds having an amino group at the said position are described in U.S. Pat. No. 4,060,615. The specification discloses 4-amino-6,7-dimethoxy-2-piperazinylquinazoline derivatives of the following formula:

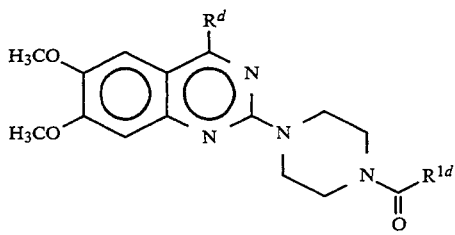

wherein $R^d$ is amino or hydrazino, $R^{1d}$ is C3–8 cycloalkyl, C3–8 methylcycloalkyl or C4–8 cycloalkenyl, and their acid addition salts.

More recently, quinazoline derivatives having inhibitory activity on cGMP-PDE have been laid open (see WO 93/07124). In this specification, the quinazoline derivatives of the following formula is disclosed.

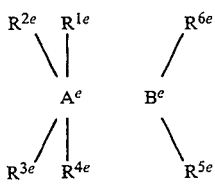

wherein ring $A^e$ is, for example, benzene, cyclohexane; ring $B^e$ is, for example, pyrimidine;

$R^{1e}$, $R^{2e}$, $R^{3e}$ and $R^{4e}$ are each, for example, hydrogen, halogen, lower alkyl optionally substituted by halogen, lower alkoxy, hydroxyalkyl, nitro, cyano, acylamino, optionally protected COOH, $S(O)n^e$—$R^{7e}$ ($n^e$ is 0,1,2, $R^{7e}$ is lower alkyl), $NR^{45e}R^{46e}$ ($R^{45e}$ and $R^{46e}$ are each, for example, hydrogen, lower alkyl);

$R^{5e}$ is, for example, optionally substituted heteroaryl (for example, pyridinyl, imidazolidinyl, qunazolidinyl);

$R^{6e}$ is, for example,

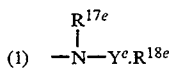

($R^{17e}$ is, for example, hydrogen, lower alkyl, alkoxyalkyl, hydroxyalkyl;

$Y^e$ is, for example, $(CH_2)q^e$ ($q^e$ is 0 to 8); $R^{18e}$ is, for example, hydrogen, hydroxy, optionally substituted heteroaryl, optionally substituted cycloalkyl),

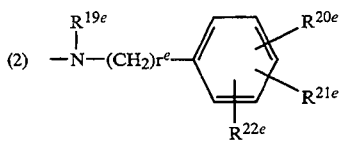

($R^{19e}$ is, for example, hydrogen, lower alkyl; $R^{20e}$, $R^{21e}$ and $R^{22e}$ are each, for example, hydrogen, halogen, nitro, low alkyl, alkoxy; $r^e$ is 0 to 8);

Furthermore, some $TXA_2$ synthetase inhibitors have been known, for example,

OKY-046

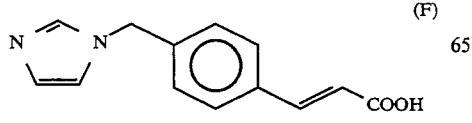

ONO-1581

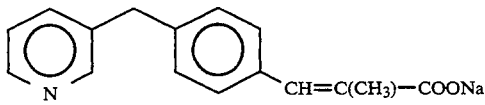

Many derivatives containing an imidazole or pyridine ring as the basic skeleton have been proposed. However, there appears to be no $TXA_2$ synthetase inhibitor having both the said ring and quinazoline ring.

Each of the foregoing documents are herein incorporated, in their entirety, by reference.

PURPOSE OF THE INVENTION

Energetic investigation has been carried out in order to discover compounds having inhibitory activities on cGMP-PDE or additionally $TXA_2$ synthetase, and as a result, the present inventors have found the compounds of the present invention.

SUMMARY OF THE INVENTION

The present invention relates to:
(i) quinazoline derivatives of the formula:

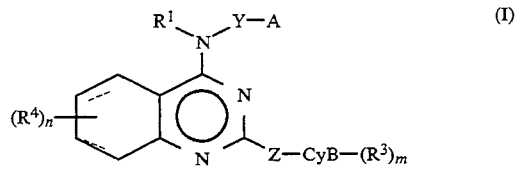

wherein $R^1$ is hydrogen or C1–4 alkyl;
Y is single bond or C1–6 alkylene;
A is
(i) —CyA—$(R^2)l$,
(ii) —O—$R^0$ or —S(O)p—$R^0$
in which $R^0$ is $R^{OA}$ or $R^{OB}$;
$R^{OA}$ is —CyA—$(R^2)l$;
$R^{OB}$ is hydrogen or C1–4 alkyl; p is 0–2;
CyA is
(1) 3–7 membered, saturated or unsaturated, monocyclic carbocyclic ring,
(2) 7-membered, unsaturated or partially saturated, monocyclic hetero ring containing as hetero atoms, one nitrogen atom, one nitrogen and one oxygen atoms, two nitrogen and one oxygen atoms, or one nitrogen and two oxygen atoms,
(3) 6-membered, unsaturated or partially saturated, monocyclic hetero ring containing as hetero atoms, one nitrogen and one oxygen atoms, two nitrogen and one oxygen atoms, or one nitrogen and two oxygen atoms,
(4) 6-membered, unsaturated or partially saturated, monocyclic hetero ring containing as hetero atoms, one nitrogen atom,
(5) 4- or 5-membered, unsaturated or partially saturated, monocyclic hetero ring containing as hetero atoms, one nitrogen atom, one nitrogen and one oxygen atoms, two nitrogen and one oxygen atoms, or one nitrogen and two oxygen atoms,
(6) 4–7 membered, unsaturated or partially saturated, monocyclic hetero ring containing as hetero atoms, one or two sulfur atoms or
(7) 4–7 membered, unsaturated or partially or fully saturated, monocyclic hetero ring containing as hetero atoms, one or two oxygen atoms;

$R^2$ is $R^{2A}$ or $R^{2B}$;

$R^{2A}$ is (1) —$NRGAR^{7A}$, in which $R^{6A}$ and $R^{7A}$ independently are hydrogen or C1–4 alkyl (with the proviso that $R^{6A}$ and $R^{7A}$ are not hydrogen at same time), (2) —$SO2NRGR^7$, in which $R^6$ and $R^7$ independently are hydrogen or C1–4 alkyl, (3) trifluoromethyl or (4) trifluoromethoxy;

$R^{2B}$ is (1) hydrogen, (2) C1–4 alkyl, (3) C1–4 alkoxy, (4)—$COOR^5$, in which $R^5$ is hydrogen or C1–4 alkyl, (5) halogen, (6) nitro or (7) —$NRGBR^{7B}$, in which $R^{6B}$ and $R^{7B}$ are hydrogen;

Z is $Z^A$ or $Z^B$;

$Z^A$ is methylene, ethylene (CH2CH2), vinylene (CH=CH) or ethynylene (C≡C);

$Z^B$ is single bond;

CyB is
(1) 7-membered, unsaturated or partially saturated, monocyclic hetero ring containing as hetero atoms, one, two or three nitrogen atoms,
(2) 6-membered, unsaturated or partially saturated, monocyclic hetero ring containing as hetero atoms, two or three nitrogen atoms,
(3) 6-membered, unsaturated or partially saturated, monocyclic hetero ring containing as hetero atoms, one nitrogen atom,
(4) 4- or 5-membered, unsaturated or partially saturated, monocyclic hetero ring containing as hetero atoms, one, two or three nitrogen atoms, or
(5) 4–7 membered, unsaturated or partially saturated, monocyclic hetero ring containing as hetero atoms, one or two oxygen atoms, or one or two sulfur atoms;

R3 is hydrogen, C1–4 alkyl, C1–4 alkoxy, halogen or trifluoromethyl;

$R^4$ is $R^{4A}$ or $R^{4B}$;

$R^{4A}$ is (1) —$NHSO_2R^{11}$, in which $R^{11}$ is C1–4 alkyl, (2) $SO_2NR^9R^{10}$, in which $R^9$ is hydrogen, C1–4 alkyl or phenyl(C1–4 alkyl) and $R^{10}$ is hydrogen or C1–4 alkyl, (3) —$OCOR^{11}$, in which $R^{11}$ is as hereinbefore defined, (4) hydroxy, (5) —$SO_2N=CHNR^{12}R^{13}$ in which $R^{12}$ is hydrogen or C1–4 alkyl and $R^{13}$ is C1–4 alkyl, (6) —$CONR^{14}R^{15}$ in which $R^{14}$ is hydrogen or C1–4 alkyl and $R^{15}$ is C1–4 alkyl or phenyl(C1–4 alkyl), (7) ethynyl, (8) tri(C1–4 alkyl)silylethynyl or (9) acetyl;

$R^{4B}$ is (1) hydrogen, (2) C1–4 alkyl, (3) C1–4 alkoxy, (4)-$COOR^8$, in which R8 is hydrogen or C1–4 alkyl, (5) —$NR^9R^{10}$, in which $R^9$ and $R^{10}$ are as hereinbefore defined, (6) —$NHCOR^{11}$, in which $R^{11}$ is as hereinbefore defined, (7) halogen, (8) trifluoromethyl, (9) nitro, (10) cyano, (11) C1–4 alkylthio, (12) C1–4 alkylsulfinyl, (13) C1–4 alkylsulfonyl, (14) hydroxymethyl, and l, m and n independently are 1 or 2; with the proviso that
(1) the group of the formula: —CyA—$(R^2)_l$ does not represent a cyclopentyl and trifluoromethylphenyl group when Y is a single bond, that
(2) a CyB ring should not bond to Z through a nitrogen atom in the CyB ring when Z is vinylene or ethynylene, that
(3) a CyB ring should not be pyridine or thiophene when CyA is a ring of CyA—(7), that
(4) Y is not a single bond, when A is (ii) —O—RO or —S(O)p-$R^0$ and that
(5) A should not be —CyA—$(R^2B)l$ and —$OR^{0B}$, when Z is $Z^B$ and $R^4$ is $R^{4B}$; or pharmaceutically acceptable acid addition salts thereof, pharmaceutically acceptable salts thereof, or hydrates thereof,
(ii) process for the preparation thereof, (iii) cGMP-PDE inhibitors, or additionally $TXA_2$ synthetase inhibitors, containing them as active ingredient, and
(iv) methods of prevention and treatment of mammals, including humans, by administering an effective amount of the compounds of the formula (I), the pharmaceutically acceptable acid addition salts thereof, the pharmaceutically acceptable salts thereof, and the hydrates thereof, to the patient to be treated.

This present invention can be classified in three groups of the formula indicated as follows;

(1) A compound of the formula [I-(A)];

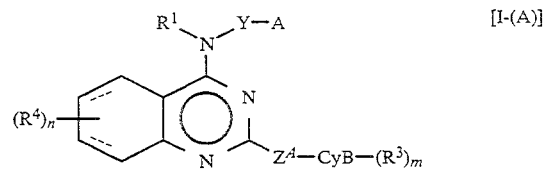

(wherein $Z^A$ is methylene, ethylene, vinylene or ethynylene; and the other symbols have the same meanings as hereinbefore defined)

(2) A compound of the formula [I-(B)];

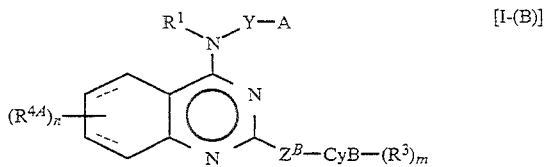

(wherein $Z^B$ is single bond; $R^{4A}$ is —$NHSO_2R^{11}$, $SO_2NR^9R^{10}$, —$OCOR^{11}$, hydroxy, —$SO_2N=CHNR^{12}R^{13}$, —$CONR^{14}R^{15}$, ethynyl, tri(C1–4 alkyl)silylethynyl or acetyl; and the other symbols have the same meanings as hereinbefore defined)

(3) A compound of the formula [I-(C)];

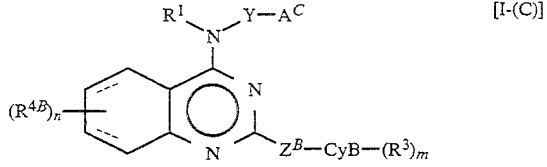

(wherein $Z^B$ is single bond; $A^C$ is —CyA—$(R^2A)l$, —O—$R^{04}$ or —S(O)p—$R^0$; $R^{0A}$ is —CyA—$(R^2)l$; $R^0$ is hydrogen, C1–4 alkyl or—CyA—$(R^2)l$; p is 0-2; $R^{2A}$ is —$NRGAR^{7A}$ (with the proviso that $R^{6A}$ and $R^{7A}$ are not hydrogen at same time), —$SO_2NRGR^7$, trifluoromethyl or trifluoromethoxy; $R^{4B}$ is hydrogen, C1–4 alkyl, C1–4 alkoxy, —$COOR^8$, —$NR^9R^{10}$, —NH$COR^{11}$, halogen, trifluoromethyl, nitro, cyano, C1–4 alkylthio, C1–4 alkylsulfinyl, C1–4 alkylsulfonyl, hydroxymethyl; and the other symbols have the same meanings as hereinbefore defined) or pharmaceutically acceptable acid addition salts thereof, pharmaceutically acceptable salts thereof, or hydrates thereof.

COMPARISON

There is no description of the compounds of the formula (I) of the present invention in those of the formulae (D) and (E) mentioned above. In detailed description, the compounds of the formula (I), of the present invention have —N—Y—A (i.e., Y is single bond or alkyl, A is —CyA—($R^2$)L, —O—$R^0$ or —S(O)p—$R^0$) group at the 4th position of a quinazoline skeleton. On the other hand, the compounds of the formula (D) in the related arts have merely an amino or hydrazino group.

The compounds of the formula (I) differ from those of formula (E) at the following points.

(1) $Z^A$ in the formula [I-(A)] dose not represent a single bond (that is, CyB is bonded to the quinazoline skeleton through a carbon chain.), but in the formula (E), $R^{5e}$ (heteroaryl) is directly bonded to the skeleton ring $B^e$, (2) $R^{4A}$ in the formula [I-(B)] represents definite groups, i.e., sulfonylamino, aminosulfonyl, acyloxy, hydroxy, —$SO_2N$=$CHNR^{12}R^{13}$, aminocarbonyl, ethynyl, tri(C1–4alkyl)silylethynyl, acetyl group, but $R^{1e}$ to $R^{4e}$ in the formula (E) do not represent them at all, (3) when $A^C$ in the formula [I-(C)] represents —CyA($R^2$A)l, $R^{24}$, the substituents of CyA, represents alkylamino, aminosulfonyl, trifluoromethane or trifluoromethoxy. However, in the formula(E), substituents $R^{20e}$ to $R^{22e}$, and substituents "substituted heteroaryl" or "substituted cycloalkyl", do not represent those of $R^{24}$, (4) $A^C$ in the formula [I-(C)] represents oxygen-containing group (i.e., 0—CyA-($R^2$)l), but $R^{6e}$ in the formula (E) dose not represent the group of O-cyclic ring, and (5) $A^C$ in the formula [I-(C)] represents sulfur-containing group (i.e., S(O)p—$R^0$), but $R^{6e}$ in the formula (E) does not represent such a group.

Accordingly, the compounds of the present invention are quite novel. Furthermore, the fact that compounds of the present invention have inhibitory activity on cGMP-PDE or additionally $TXA_2$ synthetase, is not suggested from pharmaceutical use disclosed in any related arts mentioned above. Accordingly, the compounds of the present invention are useful for the prevention and/or treatment of diseases induced by only enhancement of the metabolism of cGMP, or the increase of $TXA_2$, or induced by both factors.

DETAILED DESCRIPTION OF THE INVENTION

In the formula (I), the C1–4 alkyl group represented by $R^0$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$, mean methyl, ethyl, propyl, butyl and the isomers thereof.

In the formula (I), the C1–4 alkoxy group represented by $R^2$, $R^3$ and $R^4$ mean methoxy, ethoxy, propoxy, butoxy and isomers thereof.

In the formula (I), the halogen atom represented by $R^2$, $R^3$ and $R^4$ mean fluorine, chlorine, bromine and iodine.

In the formula (I), the C1–6 alkylene group represented by Y means methylene, ethylene, trimethylene, tetramethylene, pentamethylene, hexamethylene and isomers thereof.

In the formula (I), examples of 3–7 membered, saturated or unsaturated, monocyclic carbocyclic ring, represented by CyA—(1), are cyclobutadiene, cyclopenta-diene, benzene, cycloheptatriene ring, and partially or fully saturated rings thereof, for example, cyclobutane, cyclopentane, cyclohexane, cycloheptane ring, and cyclopropane ring.

Examples of 7-membered, unsaturated or partially saturated, monocyclic hetero ring containing as hetero atoms, one nitrogen atom, one nitrogen and one oxygen atoms, two nitrogen and one oxygen atoms, or one nitrogen and two oxygen atoms, represented by CyA—(2), are azepine, oxazepine, and partially saturated rings thereof.

Examples of 6-membered, unsaturated or partially saturated, monocyclic hetero ring containing as hetero atoms, one nitrogen and one oxygen atoms, two nitrogen and one oxygen atoms, or one nitrogen and two oxygen atoms, represented by CyA—(3), are oxazine, oxadiazine, and partially saturated rings thereof.

Examples of 6-membered, unsaturated or partially saturated, monocyclic hetero ring containing as hetero atoms, one nitrogen atom, represented by CyA—(4) and CyB-(3), are pyridine, dihydropyridine, and tetrahydropyridine.

Examples of 4- or 5-membered, unsaturated or partially saturated, monocyclic hetero ring containing as hetero atoms, one nitrogen atom, one nitrogen and one oxygen atoms, two nitrogen and one oxygen atoms, or one nitrogen and two oxygen atoms, represented by CyA—(5), are pyrrole, azetine, oxazole, isoxazole, furazan, and partially saturated rings thereof.

Examples of 4–7 membered, unsaturated or partially saturated, monocyclic hetero ring containing as hetero atoms, one or two sulfur atoms, represented by CyA—(6), are thiophene, thiain, dithiain, and partially saturated rings thereof.

Examples of 4–7 membered, unsaturated or partially or fully saturated, monocyclic hetero ring containing as hetero atom one oxygen atom represented by CyA—(7), are furan, pyran, dioxin and partially or fully saturated rings thereof.

In the formula (I), examples of 7-membered, unsaturated or partially saturated, monocyclic hetero ring containing as hetero atoms, one, two or three nitrogen atoms, represented by CyB-(1 ), are azepine, diazepine, triazepine, and partially saturated rings thereof.

Examples of 6-membered, unsaturated or partially saturated, monocyclic hetero ring containing as hetero atoms, two or three nitrogen atoms, represented by CyB-(2) are pyridazine, pyrimidine, pyrazine, triazine, and partially saturated rings thereof.

Examples of 4- or 5-membered, unsaturated or partially saturated, monocyclic hetero ring containing as hetero atoms, one, two or three nitrogen atoms, represented by CyB-(4), are pyrrole, imidazole, pyrazole, triazole, azetine, and partially saturated rings thereof, Examples of 4–7 membered, unsaturated or partially saturated, monocyclic hetero ring containing as hetero atoms, one or two oxygen atoms, or one or two sulfur atoms represented by CyB-(5), are thiophene, furan, thiain, pyran, dithiain, dioxin, dioxole, and partially saturated rings thereof.

Examples of representative compounds of the present invention are listed as follows:

| | |
|---|---|
| 1 | 4-(4-(N,N-dimethylamino)phenylmethyl)amino-2-(3-pyridyl)-quinazoline, |
| 2 | 4-(4-sulfamoylphenylmethyl)amino-2-(3-pyridyl)quinazoline, |
| 3 | 4-(3-trifluoromethylphenylmethyl)amino-2-(3-pyridyl)quinazoline, |
| 4 | 4-(3-trifluoromethoxyphenylmethyl)amino-2-(3-pyridyl)quinazoline, |
| 5 | 4-phenylmethylamino-6-methanesulfonylamino-2-(3-pyridyl)quinazoline, |

-continued

| | |
|---|---|
| 6 | 4-phenylmethylamino-6-dimethylaminosulfonyl-2-(3-pyridyl)quinazoline, |
| 7 | 4-phenylmethylamino-6-sulfamoyl-2-(3-pyridyl)quinazoline, |
| 8 | 4-phenylmethylamino-6-acetoxy-2-(3-pyridyl)quinazoline, |
| 9 | 4-phenylmethylamino-6-hydroxy-2-(3-pyridyl)quinazoline, |
| 10 | 4-phenylmethylamino-6-(N,N-dimethylaminocarbonyl)-2-(3-pyridyl)quinazoline, |
| 11 | 4-phenylmethylamino-6-ethynyl-2-(3-pyridyl)quinazoline, |
| 12 | 4-phenylmethylamino-6-trimethylsilylethynyl-2-(3-pyridyl)quinazoline, |
| 13 | 4-phenylmethylamino-6-acetyl-2-(3-pyridyl)quinazoline, |
| 14 | 4-phenylmethylamino-6-methanesulfonylamino-2-(4-pyridyl)quinazoline, |
| 15 | 4-phenylmethylamino-6-dimethylaminosulfonyl-2-(4-pyridyl)quinazoline, |
| 16 | 4-phenylmethylamino-6-sulfamoyl-2-(4-pyridyl)quinazoline, |
| 17 | 4-phenylmethylamino-6-hydroxy-2-(4-pyridyl)quinazoline, |
| 18 | 4-phenylmethylamino-6-(N,N-dimethylaminocarbonyl)-2-(3-pyridyl)quinazoline, |
| 19 | 4-phenylmethylamino-6-ethynyl-2-(4-pyridyl)quinazoline, |
| 20 | 4-phenylmethylamino-6-trimethylsilylethynyl-2-(4-pyridyl)quinazoline, |
| 21 | 4-phenylmethylamino-6-acetyl-2-(4-pyridyl)quinazoline, |
| 22 | 4-phenylmethylamino-6-methanesulfonylamino-2-(1-imidazolyl)quinazoline, |
| 23 | 4-phenylmethylamino-6-dimethylaminosulfonyl-2-(1-imidazolyl)quinazoline, |
| 24 | 4-phenylmethylamino-6-sulfamoyl-2-(1-imidazolyl)quinazoline, |
| 25 | 4-phenylmethylamino-6-hydroxy-2-(1-imidazolyl)quinazoline, |
| 26 | 4-phenylmethylamino-6-(N,N-dimethylaminocarbonyl)-2-(1-imidazolyl)quinazoline, |
| 27 | 4-phenylmethylamino-6-ethynyl-2-(1-imidazolyl)quinazoline, |
| 28 | 4-phenylmethylamino-6-trimethylsilylethynyl-2-(1-imidazolyl)quinazoline, |
| 29 | 4-phenylmethylamino-6-acetyl-2-(1-imidazolyl)quinazoline, |
| 30 | 4-phenylmethylamino-2-(2-(3-pyridyl)ethyl)quinazoline, |
| 31 | 4-phenylmethylamino-2-(2-(3-pyridyl)vinyl)quinazoline, |
| 32 | 4-phenylmethylamino-2-((1-imidazolyl)methyl)quinazoline, |
| 33 | 6-methanesulfonylamino-4-(4-tetrahydropyranylmethyl)amino-2-(1-imidazolyl)quinazoline, |
| 34 | 6-dimethylaminosulfonylamino-4-(4-tetrahydropyranylmethyl)amino-2-(1-imidazolyl)quinazoline, |
| 35 | 6-sulfamoyl-4-(4-tetrahydropyranylmethyl)amino-2-(1-imidazolyl)quinazoline, |
| 36 | 6-hydroxy-4-(4-tetrahydropyranylmethyl)amino-2-(1-imidazolyl)quinazoline, |
| 37 | 6-(N,N-dimethylaminocarbonyl)-4-(4-tetrahydropyranylmethyl)amino-2-(1-imidazolyl)quinazoline, |
| 38 | 6-ethynyl-4-(4-tetrahydropyranylmethyl)amino-2-(1-imidazolyl)quinazoline, |
| 39 | 6-trimethylsilylethynyl-4-(4-tetrahydropyranylmethyl)amino-2-(1-imidazolyl)quinazoline, |
| 40 | 6-acetyl-4-(4-tetrahydropyranylmethyl)amino-2-(1-imidazolyl)quinazoline, |
| 41 | 6-methanesulfonylamino-4-(2-methoxyethyl)amino-2-(1-imidazolyl)quinazoline, |
| 42 | 6-dimethylaminosulfonyl-4-(2-methoxyethyl)amino-2-(1-imidazolyl)quinazoline, |
| 43 | 6-sulfamoyl-4-(2-methoxyethyl)amino-2-(imidazolyl)quinazoline, |
| 44 | 6-hydroxy-4-(2-methoxyethyl)amino-2-(1-imidazolyl)quinazoline, |
| 45 | 6-(N,N-dimethylaminocarbonyl)-4-(2-methoxyethyl)amino-2-(1-imidazolyl)quinazoline, |
| 46 | 6-ethynyl-4-(2-methoxyethyl)amino-2-(1-imidazolyl)quinazoline, |
| 47 | 6-trimethylsilylethynyl-4-(2-methoxyethyl)amino-2-(1-imidazolyl)quinazoline, |
| 48 | 6-acetyl-4-(2-methoxyethyl)amino-2-(1-imidazolyl)quinazoline, |
| 49 | 6-methanesulfonylamino-4-(2-dimethylaminoethyl)amino-2-(1-imidazolyl)quinazoline, |
| 50 | 6-dimethylaminosulfonyl-4-(2-dimethylaminoethyl)amino-2-(1-imidazolyl)quinazoline, |
| 51 | 6-sulfonyl-4-(2-dimethylaminoethyl)amino-2-(1-imidazolyl)quinazoline, |
| 52 | 6-hydroxy-4-(2-dimethylaminoethyl)amino-2-(1-imidazolyl)quinazoline, |
| 53 | 6-(N,N-dimethylaminocarbonyl)-4-(2-dimethylaminoethyl)amino-2-(1-imidazolyl)quinazoline, |
| 54 | 6-ethynyl-4-(2-dimethylaminoethyl)amino-2-(1-imidazolyl)quinazoline, |
| 55 | 6-trimethylsilylethynyl-4-(2-dimethylaminoethyl)amino-2-(1-imidazolyl)quinazoline, |
| 56 | 6-acetyl-4-(2-dimethylaminoethyl)amino-2-(1-imidazolyl)quinazoline, |
| 57 | 6-methanesulfonylamino-4-(2-phenoxyethyl)amino-2-(1-imidazolyl)quinazoline, |
| 58 | 6-dimethylaminosulfonyl-4-(2-phenoxyethyl)amino-2-(1-imidazolyl)quinazoline, |
| 59 | 6-sulfamoyl-4-(2-phenoxyethyl)amino-2-(1-imidazolyl)quinazoline, |
| 60 | 6-hydroxy-4-(2-phenoxyethyl)amino-2-(1-imidazolyl)quinazoline, |
| 61 | 6-(N,N-dimethylaminocarbonyl)-4-(2-phenoxyethyl)amino-2-(1-imidazolyl)quinazoline, |
| 62 | 6-ethynyl-4-(2-phenoxyethyl)amino-2-(1-imidazolyl)quinazoline, |
| 63 | 6-trimethylsilylethynyl-4-(2-phenoxyethyl)amino-2-(1-imidazolyl)quinazoline, |
| 64 | 7-acetyl-4-(2-phenoxyethyl)amino-2-(1-imidazolyl)quinazoline, |
| 65 | 6-ethynyl-4-(2-methoxyethyl)amino-2-(2-azepinyl)quinazoline, |
| 66 | 6-ethynyl-4-(2-methoxyethyl)amino-2-(1,5-diazepin-2-yl)quinazoline, |
| 67 | 6-ethynyl-4-(2-methoxyethyl)amino-2-(2-pyrimidinyl)quinazoline, |
| 68 | 6-ethynyl-4-(2-methoxyethyl)amino-2-(2-triazinyl)quinazoline, |
| 69 | 6-ethynyl-4-(2-methoxyethyl)amino-2-(2-pyridyl)quinazoline, |
| 70 | 6-ethynyl-4-(2-methoxyethyl)amino-2-(4-pyridyl)quinazoline, |
| 71 | 6-ethynyl-4-(2-methoxyethyl)amino-2-(2-(3-pyridyl)ethyl)quinazoline, |
| 72 | 6-ethynyl-4-(2-methoxyethyl)amino-2-(2-(3-pyridyl)vinyl)quinazoline, |
| 73 | 6-ethynyl-4-(2-methoxyethyl)amino-2-(2-pyrrolyl)quinazoline, |
| 74 | 6-ethynyl-4-(2-methoxyethyl)amino-2-(1-imidazolyl)quinazoline, |
| 75 | 6-ethynyl-4-(2-methoxyethyl)amino-2-((1-imidazolyl)methyl)quinazoline, |
| 76 | 6-ethynyl-4-(2-methoxyethyl)amino-2-(2-methyl-1-imidazolyl)quinazoline, |
| 77 | 6-ethynyl-4-(2-methoxyethyl)amino-2-(1-triazolyl)quinazoline, |
| 78 | 6-ethynyl-4-(2-methoxyethyl)amino-2-(2-thienyl)quinazoline, |
| 79 | 6-ethynyl-4-(2-methoxyethyl)amino-2-(2-furyl)quinazoline, |
| 80 | 6-ethynyl-4-((2-azepinylmethyl)methyl)amino-2-(3-pyridyl)quinazoline, |
| 81 | 6-ethynyl-4-((3-pyridylmethyl)methyl)amino-2-(3-pyridyl)quinazoline, |
| 82 | 6-ethynyl-4-((1-methyl-2-pyrrolyl)methyl)amino-2-(3-pyridyl)quinazoline, |
| 83 | 6-ethynyl-4-((3-isoxazolyl)methyl)amino-2-(3-pyridyl)quinazoline, |
| 84 | 6-ethynyl-4-((2-thienylmethyl)methyl)amino-2-(3-pyridyl)quinazoline, |
| 85 | 6-ethynyl-4-(3-pyridylmethyl)amino-2-(3-pyridyl)quinazoline, |
| 86 | 4-(2-methylthioethyl)amino-2-(2-azepinyl)quinazoline, |
| 87 | 4-(2-methylthioethyl)amino-2-(1,5-diazepin-2-yl)quinazoline, |

-continued

| | |
|---|---|
| 88 | 4-(2-methylthioethyl)amino-2-(2-pyrimidinyl)quinazoline, |
| 89 | 4-(2-methylthioethyl)amino-2-(2-triazinyl)quinazoline, |
| 90 | 4-(2-methylthioethyl)amino-2-(2-pyridyl)quinazoline, |
| 91 | 4-(2-methylthioethyl)amino-2-(4-pyridyl)quinazoline, |
| 92 | 4-(2-methylthioethyl)amino-2-(2-(3-pyridyl)ethyl)quinazoline, |
| 93 | 4-(2-methylthioethyl)amino-2-(2-(3-pyridyl)vinyl)quinazoline, |
| 94 | 4-(2-methylthioethyl)amino-2-(2-pyrrolyl)quinazoline, |
| 95 | 4-(2-methylthioethyl)amino-2-(1-imidazolyl)quinazoline, |
| 96 | 4-(2-methylthioethyl)amino-2-((1-imidazolyl)quinazoline, |
| 97 | 4-(2-methylthioethyl)amino-2-(2-methyl-1-imidazolyl)quinazoline, |
| 98 | 4-(2-methylthioethyl)amino-2-(1-triazolyl)quinazoline, |
| 99 | 4-(2-methylthioethyl)-2-(2-thienyl)quinazoline, |
| 100 | 4-(2-methylthioethyl)amino-2-(2-furyl)quinazoline, |
| 101 | 4-(2-methylsulfinylethyl)amino-2-(2-azepinyl)quinazoline, |
| 102 | 4-(2-methylsulfinylethyl)amino-2-(1,5-diazepin-2-yl)quinazoline, |
| 103 | 4-(2-methylsulfinylethyl)amino-2-(2-pyrimidinyl)quinazoline, |
| 104 | 4-(2-methylsulfinylethyl)amino-2-(2-triazinyl)quinazoline, |
| 105 | 4-(2-methylsulfinylethyl)amino-2-(2-pyridyl)quinazoline, |
| 106 | 4-(2-methylsulfinylethyl)amino-2-(4-pyridyl)quinazoline, |
| 107 | 4-(2-methylsulfinylethyl)amino-2-(2-(3-pyridyl)ethyl)quinazoline, |
| 108 | 4-(2-methylsulfinylethyl)amino-2-(2-(3-pyridyl)vinyl)quinazoline, |
| 109 | 4-(2-methylsulfinylethyl)amino-2-(2-pyrrolyl)quinazoline, |
| 110 | 4-(2-methylsulfinylethyl)amino-2-(1-imidazolyl)quinazoline, |
| 111 | 4-(2-methylsulfinylethyl)amino-2-((1-imidazolyl)methyl)quinazoline, |
| 112 | 4-(2-methylsulfinylethyl)amino-2-(2-methyl-1-imidazolyl)quinazoline, |
| 113 | 4-(2-methylsulfinylethyl)amino-2-(1-triazolyl)quinazoline, |
| 114 | 4-(2-methylsulfinylethyl)amino-2-(2-thienyl)quinazoline, |
| 115 | 4-(2-methylsulfinylethyl)amino-2-(2-furyl)quinazoline, |
| 116 | 4-(2-methylsulfonylethyl)amino-2-(2-azepinyl)quinazoline, |
| 117 | 4-(2-methylsulfonylethyl)amino-2-(1,5-diazepin-2-yl)quinazoline, |
| 118 | 4-(2-methylsulfonylethyl)amino-2-(2-pyrimidinyl)quinazoline, |
| 119 | 4-(2-methylsulfonylethyl)amino-2-(2-triazinyl)quinazoline, |
| 120 | 4-(2-methylsulfonylethyl)amino-2-(2-pyridyl)quinazoline, |
| 121 | 4-(2-methylsulfonylethyl)amino-2-(4-pyridyl)quinazoline, |
| 122 | 4-(2-methylsulfonylethyl)amino-2-(2-(3-pyridyl)quinazoline, |
| 123 | 4-(2-methylsulfonylethyl)amino-2-(2-(3-pyridyl)quinazoline, |
| 124 | 4-(2-methylsulfonylethyl)amino-2-(2-pyrrolyl)quinazoline, |
| 125 | 4-(2-methylsulfonylethyl)amino-2-(1-imidazolyl)quinazoline, |
| 126 | 4-(2-methylsulfonylethyl)amino-2-((1-imidazolyl)methyl)quinazoline, |
| 127 | 4-(2-methylsulfonylethyl)amino-2-(2-methyl-1-imidazolyl)quinazoline, |
| 128 | 4-(2-methylsulfonylethyl)amino-2-(1-triazolyl)quinazoline, |
| 129 | 4-(2-methylsulfonylethyl)amino-2-(2-thienyl)quinazoline, |
| 130 | 4-(2-methylsulfonylethyl)amino-2-(2-furyl)quinazoline, | and further those described in Examples below are also representative compounds of the present invention.

Salts and Acid Addition Salts

The compounds of the formula (I), if desired, may be converted into acid addition salts by known methods. Preferably, acid addition salts are non-toxic and water-soluble. The suitable acid addition salts are, for example, salts of an inorganic acid such as hydrochloric acid, hydrobromic acid, hydroiodic acid, sulfuric acid, phosphoric acid, nitric acid, or an organic acid such as acetic acid, lactic acid, tartaric acid, benzoic acid, citric acid, methanesulfonic acid, ethanesulfonic acid, benzenesulfonic acid, toluenesulfonic acid, isethionic acid, glucuronic acid and gluconic acid.

The compounds of the formula (I), if desired, may be converted into salts by known methods. Preferable, salts are non-toxic salts and water-soluble. The suitable salts are salts of alkaline metal (sodium, potassium etc.), salts of alkaline earth metal (calcium, magnesium etc.), ammonium salts, salts of pharmaceutically acceptable organic amine (tetramethylammonium, triethylamine, methylamine, dimethylamine, cyclopentylamine, phenylmethylamine, phenethylamine, piperidine, monoethanolamine, diethanolamine, tris(hydroxymethyl)methylamine, lysine, arginine, N-methyl-D-glucamine etc.).

Throughout the specification including claims, it may be easily understood by those skilled in the art, that the alkyl, alkoxy, groups include straight-chained and also branched-chained ones. Accordingly, all isomers produced by the difference in stereo configuration, such as asymmetric carbons are included in the present invention.

Preparations

According to the present invention, of the compounds of the present invention, the compounds of the formula:

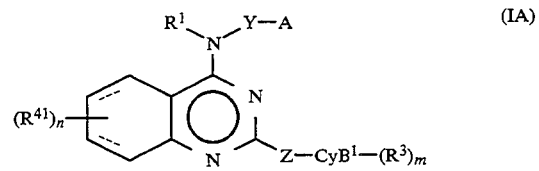
(IA)

wherein $R^{41}$ is (1) hydrogen, (2) C1-4 alkyl, (3) C1-4 alkoxy, (4) —COOR$^8$, (5) —NR$^{91}$R$^{101}$, in which R$^{91}$ is hydrogen, C1-4 alkyl or phenyl(C1-4 alkyl) and R$^{101}$ is hydrogen or C1-4 alkyl, provided that both R$^{91}$ and R$^{101}$ are not hydrogen, (6) SO$_2$NR$^9$R$^{10}$, in which R$^9$ and R$^{10}$ are as hereinbefore defined, (7) halogen, (8)trifluoromethyl, (9) nitro, (10)cyano, (11)C1-4 alkylthio, (12) tri(C1-4 alkyl)silylethynyl, (13) —SO$_2$N=CHNR$^{12}$R$^{13}$, in which R$^{12}$ and R$^{13}$ are the same meaning as hereinbefore defined, or (14) —CONR$^{14}$R$^{15}$, in which R$^{14}$ and R$^{15}$ are the same meaning as hereinbefore defined, CyB$^1$ is as hereinbefore defined for CyB, provided that a carbon atom in the ring should bond to Z, and the other symbols are as hereinbefore defined; and the compounds of the formula:

(IB)

wherein $Z^1$ is single bond or methylene, $CyB^2$ is as hereinbefore defined for CyB, provided that a nitrogen atom in the ring should bond to $Z^1$, and the other symbols are as hereinbefore defined; may be prepared by using a series of reactions depicted in Scheme A and B, respectively, wherein $R^{50}$ is C1-4 alkyl and the other symbols are as hereinbefore defined.

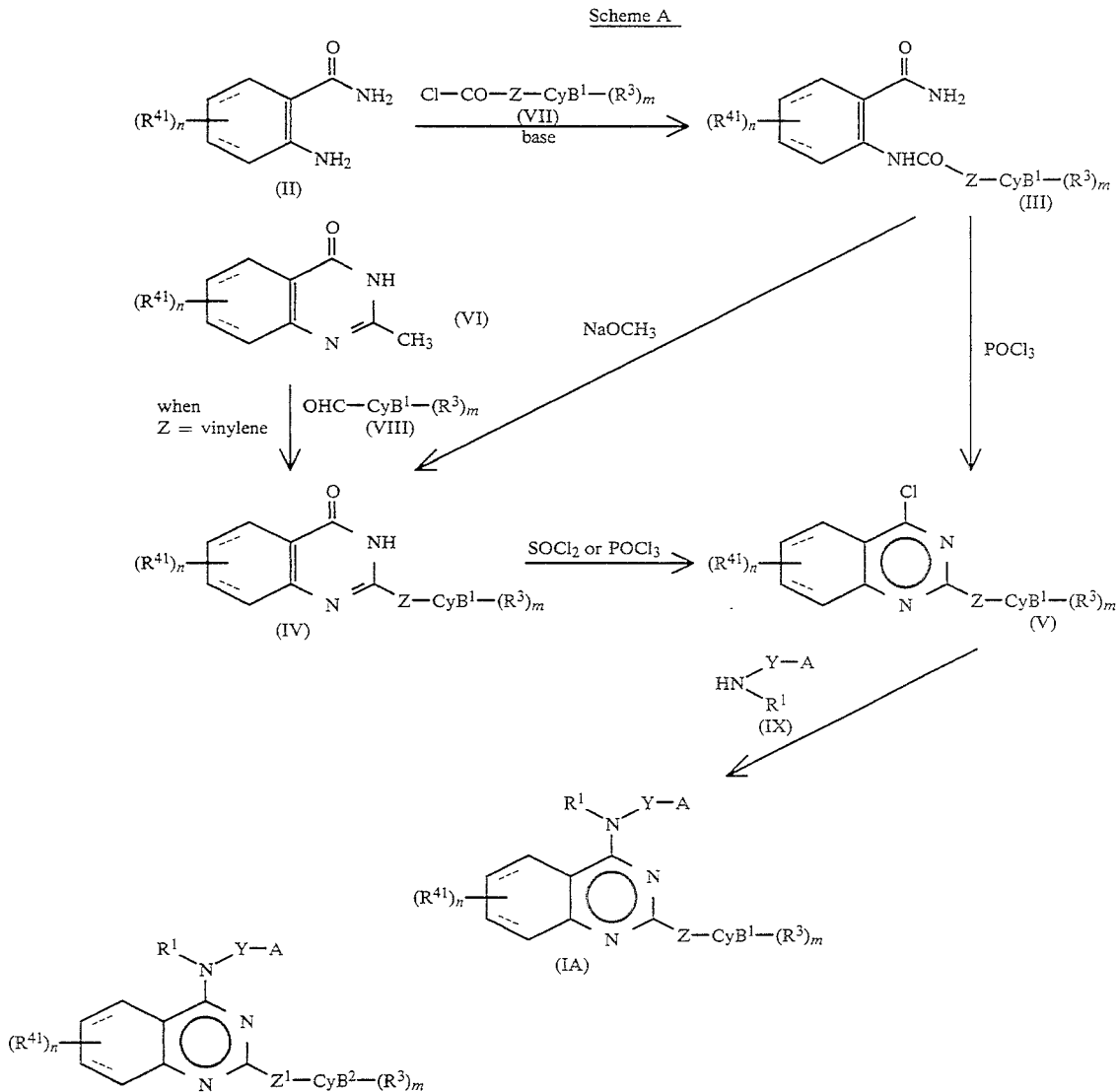

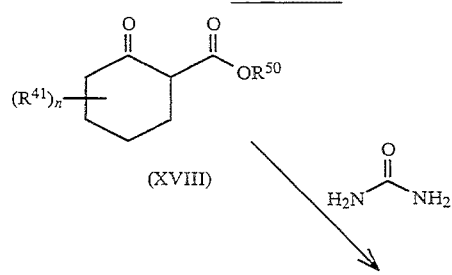

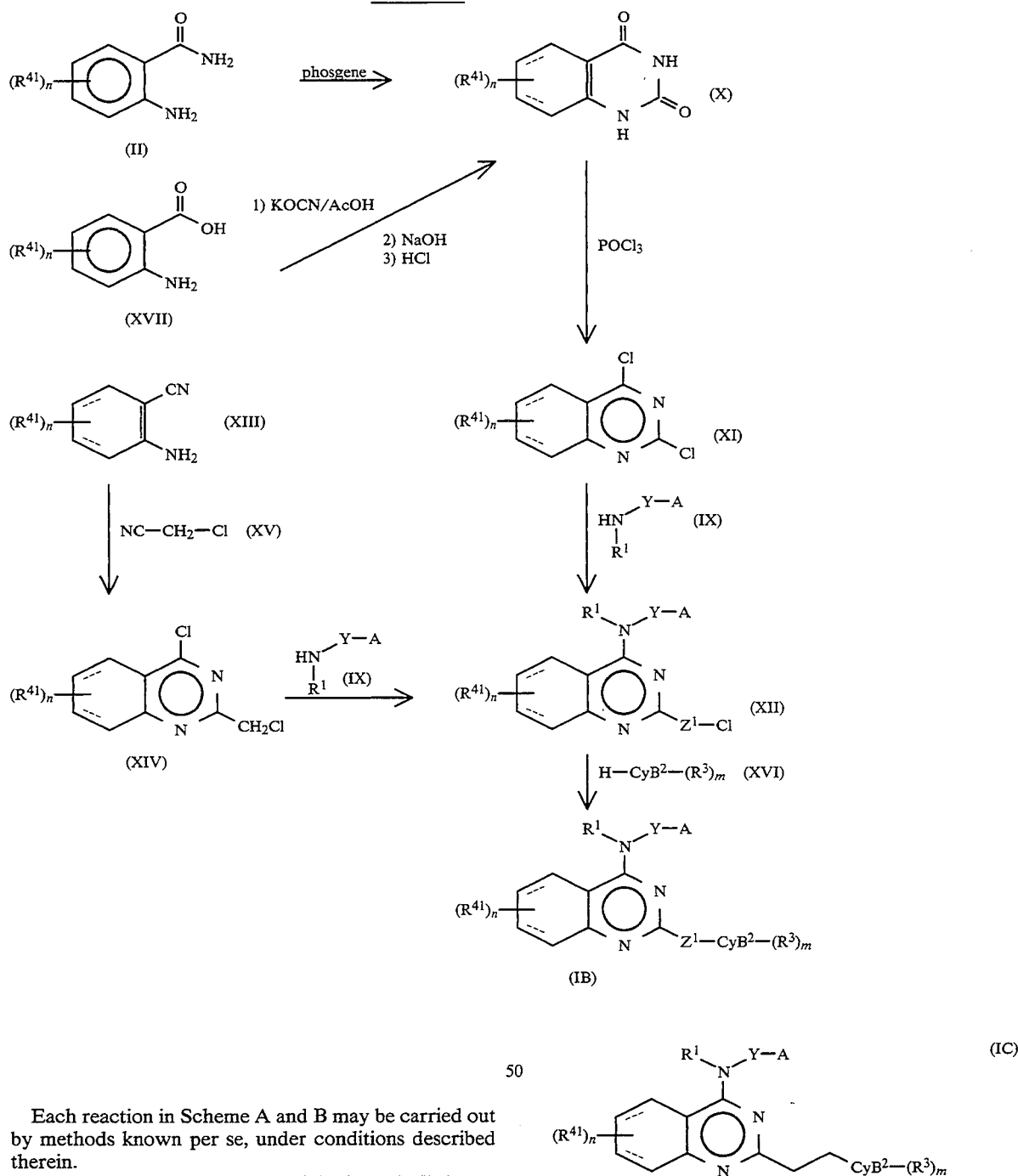

Each reaction in Scheme A and B may be carried out by methods known per se, under conditions described therein.

For example, the compounds of the formula (IA) may be prepared from those of the formula (V) by the reaction with an amine of the formula (IX) in a proper organic solvent such as a lower alkanol (e.g. ethanol) or tetrahydrofuran, or a mixture thereof, at a temperature from ambient to reflux, for several hours to several days, if necessary in the presence of a base such as triethylamine.

Further, the compounds of the formula (IB) may be prepared from those of the formula (XII) by the reaction with a cyclic amine of the formula (XVI) in phenol at a reflux temperature for several hours.

Furthermore, the compounds of the present invention, of the formula:

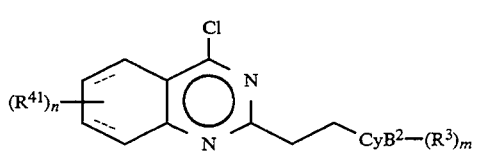

wherein the various symbols are as hereinbefore defined; may be prepared from those of the formula:

(XVII)

wherein the various symbols are as hereinbefore defined; by the methods described hereinbefore for the conversion of the compounds of the formula (V) into those of the formula (IA). The compounds of the formula (XVII) may be prepared by the methods similar to those described hereinbefore in Scheme A.

On the other hand, the compounds of the formula (I) other than those of the formulae (IA), (IB) and (IC) may be prepared by the methods known per se described below.

The compounds of the formula (I) wherein $R^4$ is amino may be prepared from those wherein $R^4$ is nitro, by the reduction with zinc etc. in a proper organic solvent.

The compounds of the formula (I) wherein $R^4$ is hydroxy may be prepared from those wherein $R^4$ is alkoxy such as methoxy, by the reaction with hydrogen bromide or tribromoboron.

The compounds of the formula (I) wherein $R^4$ is—$NHCOR^{11}$, wherein $R^{11}$ is as hereinbefore defined, may be prepared from those wherein $R^4$ is nitro, by the reaction with the corresponding organic acid such as acetic acid in the presence of zinc dust.

The compounds of the formula (I) wherein $R^4$ is $NHSO_2R^{11}$, wherein $R^{11}$ is as hereinbefore defined, may be prepared from those wherein R4 is amino by the reaction with the corresponding alkylsulfonyl chloride such as methanesulfonyl chloride.

The compounds of the formula (I) wherein $R^4$ is —$OCOR^{11}$, wherein $R^{11}$ is as hereinbefore defined, may be prepared from those wherein $R^4$ is hydroxy by the esterification with the corresponding organic acid such as acetic acid.

The compounds of the formula (I) wherein $R^4$ is C1–4 alkylsulfinyl or C1–4 alkylsulfonyl may be prepared from those wherein $R^4$ is C1–4 alkylthio by the oxidation by oxidating agent such as hydrogen peroxide.

The compounds of the formula (I) wherein $R^4$ is hydroxymethyl may be prepared from those wherein $R^4$ is alkyoxycarbonyl, by the reduction with reducing agent such as lithium borohydride, lithium aluminum hydride etc.

The compounds of the formula (I) wherein $R^4$ is ethynyl may be prepared from those wherein $R^4$ is tri(C1–4 alkyl)silylethynyl, by the removal reaction of silyl group with tetrabutylammonium halide.

The compounds of the formula (I) wherein $R^4$ is acetyl may be prepared from those wherein $R^4$ is ethynyl, by the reaction with mercury sulfate and acetic acid in an acidic condition.

In each reaction in the present specification, products may be purified by conventional manner. For example, it may be carried out by distillation at atmospheric or reduced pressure, high performance liquid chromatography, thin layer chromatography or column chromatography using silica gel or magnesium silicate, washing or recrystallization. Purification may be carried out after each reaction, or after a series of reactions.

The starting materials of the formulae (II), (VI) and (XIII), and each reagents of the formulae (VII), (VIII), (IX), (XV), (XVI), (XVII) and (XVIII) used in the process for the preparation of the present invention are known per se or may be easily prepared by known methods.

Effect

The compounds of the formula (I), pharmaceutically acceptable acid addition salts thereof, pharmaceutically acceptable salts thereof, or hydrates thereof, of the present invention have an inhibitory effect on cGMPPDE, or additionally on $TXA_2$ synthetase, and are, therefore, useful for the prevention and/or treatment of not only diseases induced by enhancement of the metabolism of cGMP, such as hypertension, heart failure, myocardial infarction, angina, atherosclerosis, cardiac edema, renal insufficiency, nephrotic edema, hepatic edema, asthma, bronchitis, dementia, immunodeficiency, pulmonary hypertension, but also diseases induced by enhancement of the synthesis of $TXA_2$ such as inflammation, thrombosis, cerebral apoplexy, asthma, cardiostenosis, cerebral infarction etc, in mammals, especially in humans.

The inhibitory effect on cGMP-PDE and $TXA_2$ synthetase, of the compounds of the present invention were confirmed by screening tests as described below.

(1) Inhibitory effect on cGMP-PDE

Method

PDE IC was isolated from human platelets according to standard methods previously described in Lugnier, C. et al., *Biochem. Pharmacol.* 35: 1743, 1986 (incorporated in its entirety by reference). Typically, connective tissue and adventitia were removed and 1–2 units of platelets were suspended in 10 volumes of buffer A (20 mM Tris-HCl, pH 7.5, containing 2 mM magnesium acetate, 1 mM dithiothreitol, and 5 mM Na2EDTA) using a Brinkman polytron. The proteinase inhibitors leupeptin, pepstatin A, and phenylmethyl-sulfonyl fluoride (PMSF) were also included in this buffer (final concentration of 100 nM each). The homogenate was centrifuged at 100,000g for 60 minutes. The supernatant was then removed and filtered through four layers of cheesecloth. The supernatant was applied to a DWAE-Trisacryl M column. The column was washed with several bed volumes of buffer B (20 mM Tris-HCl, pH 7.5, containing 2 mM magnesium acetate, 1 mM dithiothreitol, and proteinase inhibitors) and eluted by two successive linear NaCl gradients (0.05–0.15M, 300 ml total; 0.15–0.40M, 200 ml total). Five milliliter fractions were collected and assayed for cyclic GMP PDE activity.

Phosphodiesterase activity was measured, as described by Thompson, et al., *Adv. Cyclic Nucleotide Res.* 10: 69, 1979 (incorporated in its entirety by reference), in a reaction medium containing 40 mM Tris-HCl (pH 8.0), 5 mM MgCl2, and 1 mM dithiothreitol. The concentration of substrate ($^3$H-cGMP) was 0.2 mM. Compounds of the present invention were dissolved in dimethyl sulfoxide (DMSO) at a final concentration of 2.5%. This concentration of DMSO inhibited enzyme activity by approximately 10%. The $IC_{50}$ values (concentration that produced 50% inhibition of substrate hydrolysis) for the compounds examined were determined from concentration-response curves in which concentrations typically ranged from $10^{-8}$ to $10^{-3}$M for the less potent inhibitors (half-log increments).

Result

TABLE 1

| Inhibitory activity on cGMP-PDE | | |
|---|---|---|
| Compounds Example No. | | Inhibitory activity $IC_{50}$, (M) |
| 3(o) | (3HCl salt) | $2.4 \times 10^{-6}$ |
| 6(b) | (2HCl salt) | $3.0 \times 10^{-7}$ |
| 6(j) | (2HCl salt) | $1.35 \times 10^{-7}$ |
| 7 | (free base) | $2.0 \times 10^{-7}$ |
| 18 | (2HCl salt) | $4.6 \times 10^{-8}$ |
| 18(b) | (2HCl salt) | $5.3 \times 10^{-10}$ |

(2) Inhibitory effect on $TXA_2$ synthetase

Method

Male Wistar rats were starved overnight. Five hundreds microliter of heparinized (10 U/mL) whole blood was collected from abdominal aorta using polyethylene syringe (needle: 22 or 26G). The blood freshly drawn from animal was preincubated with 5 μL of test compound at 37° C. Five minutes later, 2.5 μL of 6 mM of Ca ionophore A23187 (final concentration of 30 μM) was added into tube, and incubation mixture was further incubated for 15 min. The reaction was terminated by centrifugation of tubes at 12,000 rpm for 2 min. $TXB_2$ content in the supernatant was determined by EIA as follows.

One milliliter of 0.5M glycine-HCl buffer (pH 3.2) was added to 100 μL of sample. The samples were mixed well and centrifuged at 1,700 G for 10 min at 4° C. The extracted supernatant was applied to a SEP-PAK (registered Trade Mark) $C_{18}$ cartridge (Waters Assoc.). After washing with 10 mL of distilled water followed by 10 mL each of 15% ethanol and petroleum ether, the sample was eluted with 3 mL of ethyl acetate. The ethyl acetate fraction was evaporated to dryness under gentle $N_2$ stream and the residue was dissolved in EIA buffer (final volume of 1 mL) following the addition of 300 μL of 0.01M $NaHCO_3$-NaOH buffer (pH 10.0). EIA for $TXB_2$ was carried out according to a legend attached to the kit (Chyman Chemical Co., Inc.). Overall recovery of $TXB^2$ in this extraction procedure was 90%. The $IC_{50}$ values (concentration that produced 50% inhibition of $TXB_2$ synthesis) for the compounds examined were determined from concentration-response curves.

Result

TABLE 2

| Inhibitory activity on $TXA_2$ synthetase | | |
|---|---|---|
| Compounds Example No. | | Inhibitory activity $IC_{50}$, (M) |
| 18 | (2HCl salt) | $2.4 \times 10^{-6}$ |

On the other hand, it was confirmed that the acute toxicity of the compound of the present invention is very weak. Therefore, the compounds of the present invention may be considered to be sufficiently safe and suitable for pharmaceutical use.

Application for Pharmaceuticals

For the purpose above described, the compounds, of the formula (I), of the present invention, pharmaceutically acceptable acid addition salts thereof and hydrates thereof may be normally administered systemically or partially, usually by oral or parenteral administration.

The doses to be administered are determined depending upon age, body weight, symptom, the desired therapeutic effect, the route of administration, and the duration of the treatment etc. In the human adult, the doses per person are generally between 1 mg and 1000 mg, by oral administration, up to several times per day, and between 1 mg and 100 mg, by parenteral administration up to several times per day, or continuous administration between 1 and 24 hrs. per day intravenously.

As mentioned above, the doses to be used depend upon various conditions. Therefore, there are cases in which doses lower than or greater than the ranges specified above may be used.

Administration of the compounds of the present invention, may be as solid compositions, liquid compositions or other compositions for oral administration, as injections, liniments or suppositories etc. for parenteral administration.

Solid compositions for oral administration include compressed tablets, pills, capsules, dispersible powders, and granules. Capsules include hard capsules and soft capsules.

In such compositions, one or more of the active compound(s) is or are, admixed with at least one inert diluent (such as lactose, mannitol, glucose, hydroxypropyl cellulose, micro crystalline cellulose, starch, polyvinylpyrrolidone, magnesium metasilicate aluminate etc.) The compositions may also comprise, as is normal practice, additional substances other than inert diluents: e.g. lubricating agents (such as magnesium stearate etc.), disintegrating agents (such as cellulose calcium glycolate etc.), stabilizing agents (such as lactose etc.), and assisting agents for dissolving (such as glutamic acid, aspartic acid etc.).

The tablets or pills may, if desired, be coated with film of gastric or enteric material (such as sugar, gelatin, hydroxypropyl cellulose or hydroxypropylmethyl cellulose phthalate etc.), or be coated with more than two films. And further, coating may include containment within capsules of absorbable materials such as gelatin.

Liquid compositions for oral administration include pharmaceutically-acceptable solutions, emulsions, suspensions, syrups and elixirs.

In such compositions, one or more of the active compound(s) is or are comprise in inert diluent(s) commonly used in the art (purified water, ethanol etc.).

Besides inert diluents, such compositions may also comprise adjuvants (such as wetting agents, suspending agents etc.), sweetening agents, flavouring agents, perfuming agents and preserving agents.

Other compositions for oral administration include spray compositions which may be prepared by known methods and which comprise one or more of the active compound(s).

Spray compositions may comprise additional substances other than inert diluents: e.g. stabilizing agents (sodium sulfite etc.), isotonic buffer (sodium chloride, sodium citrate, citric acid etc.)

For preparation of such spray compositions, for example, the method described in the U.S. Pat. No. 2,868,691 or 3,095,355 (herein incorporated in their entireties by reference) may be used.

Injections for parenteral administration include sterile aqueous or non-aqueous solutions, suspensions and emulsions. In such compositions, one more of active compound(s)is or are admixed with at least one of inert aqueous diluent(s) (distilled water for injection, physiological salt solution etc.) or inert non-aqueous diluent(s) (propylene glycol, polyethylene glycol, olive oil, ethanol, POLYSOLBATE80 (registered trade mark) etc.).

Injections may comprise additional other than inert diluents: e.g. preserving agents, wetting agents, emulsifying agents, dispersing agents, stabilizing agent (lactose etc.), assisting agents such as assisting agents for dissolving (glutamic acid, aspartic acid etc.).

They may be sterilized for example, by filtration through a bacteria-retaining filter, by incorporation of sterilizing agents in the compositions or by irradiation. They also be manufactured in the form of sterile solid compositions, for example, by freeze- drying, and which can be dissolved in sterile water or some other sterile diluents for injection immediately before used.

Other compositions for parenteral administration include liquids for external use, and endermic liniments (ointment etc.), suppositories and pessaries which comprise one or more of the active compound(s) and may be prepared by known methods.

Reference Example and Examples

The following Reference examples and examples are intended to illustrate, but not limit, the present invention. In Reference examples and examples, "mp" shows "melting point".

Reference example 1

4-fluoroisatoic anhydride

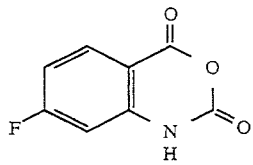

To a solution of 2-amino-4-fluorobenzoic acid (4.65 g) in 50 mL of mixed solvent (10:1=toluene:tetrahydrofuran) was added phosgene (4.46 g, 1.93M solution of toluene) dropwise via a drop funnel. The mixture was stirred at room temperature for 1 hour and then heated to reflux over night. The mixture was concentrated to about 10 mL and cooled in refrigerator. The precipitate was filtered, washed with ether (5 mL×2) and air-dried to give the title compound (5.43 g) as a white solid having the following physical data.

NMR (200 MHz, DMSO-d6): δ6.92 (dd, 1H), 7.11 (td, 1H), 8.00 (dd, 1H), 11.92 (broad, 1H).

Reference example 2

4-fluoroanthranilamide

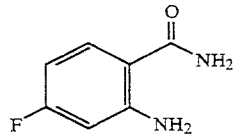

A solution of the isatoic anhydride compound (3.62 g, prepared in Reference example 1) in 100 mL of tetrahydrofuran was placed in a 200 mL round bottle equipped with gas in- and outlet. The anhydrous ammonia gas was gently bubbled into the solution for 1.5 to 2 hours. After removal of the solvent the residue was taken up in methylene chloride (30 mL) and water (30 mL). The precipitate was collected by filtration and washed with methylene chloride (10 mL) to give the title compound (1.95 g) as a pale white solid having the following physical data.

NMR (200 MHz, DMSO-d6): δ6.70 (m, 1H), 6.82 (m, 1H), 6.90 (broad, 2H), 7.72 (m, 1H).

The following compounds were obtained by the same procedure as Reference example 1 and Reference example 2, by using the corresponding substituted anthranilic acid compound.

Reference example 2(a).

5-methylanthranilamide

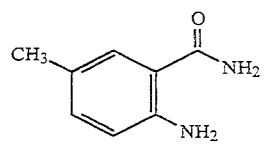

The product was collected by filtration as a pale solid.

NMR (200 MHz, DMSO-d6): δ 2.24 (s, 3H), 5.50 (broad, 2H), 6.62 (d, 1H), 7.07 (dd, 1H), 7.16 (d, 1H).

Reference example 2(b)

5-chloroanthranilamide

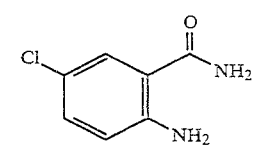

The product was collected by filtration as a pale solid.

NMR (200 MHz, DMSO-d6): δ 5.68 (broad, 2H), 6.64 (d, 1H), 7.20 (dd, 1H), 7.35 (d, 1H).

Reference example 2(C)

5-bromoanthranilamide

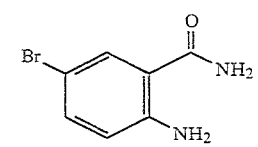

The product was collected by filtration as a pale brown.

NMR (200 MHz, DMSO-d6): δ 6.66 (dd, 1H), 6.72 (broad, 2H), 7.20 (broad, 1H), 7.26 (dt, 1H), 7.70 (t, 1H), 7.82 (broad, 1H).

Reference example 2(d)

5-nitroanthranilamide

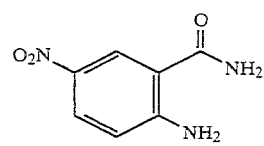

The product was collected by filtration as a solid.

NMR (200 MHz, DMSO-dG): δ 6.80 (dd,1 H), 7.40 (broad, 1H), 7.90 (broad, 2H), 8.03 (dt, 1H), 8.20 (broad, 1H), 8.56 (t, 1H).

Reference example 3

4-fluoro-2-[N-(3-pyridylcarbonyl)amino]benzamide

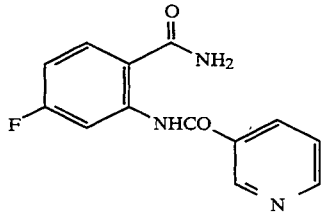

To a solution of the anthranilamide compound (1.54 g, prepared in Reference example 2) and triethylamine (1.4 g) in 100 mL of tetrahydrofuran was added nicotinoyl chloride hydrochloride (1.95 g). The resulting mixture was heated to reflux for one to three days and then concentrated. The residue was taken up in water (25 mL) and chloroform (30 mL). The insoluble crude product was collected by filtration and then vacuum dried. The crude product was triturated with 10 mL of ether and pentane solution (1:1) to afford the title compound (2.27 g) as a white solid having the following physical data.

NMR (200 MHz, DMSO-d6): δ 7.10 (td, 1H), 7.80 (m, 1H), 7.99 (broad, 1H), 8.07 (m, 1H), 8.40–8.55 (m, 3H), 8.90 (m, 1H), 9.15 (m, 1H).

Reference example 4

7-fluoro-2-(3-pyridyl)quinazolin-4-one

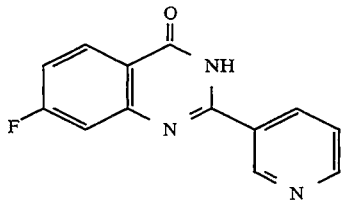

To a suspension of the benzamide compound (1.6 g, prepared in Reference example 3) in 60 mL of toluene was added sodium methoxide (853 mg). The solution was heated to reflux for one to three days. After cooling to room temperature, the mixture was quenched with ammonium chloride solution (30 mL) with a vigorously shaking. The mixture was cooled in refrigerator and the insoluble product was collected by filtration and dried in vacuum to give the title compound (1.39 g) as a white solid having the following physical data.

NMR (200 MHz, DMSO-d6): ,5 7.43 (td, 1H), 7.53–7.64 (m, 2H), 8.20–8.28 (m, 1H), 8.50 (dt, 1H), 8.78 (dd, 1H), 9.29 (m, 1H).

Reference example 5

4-chloro-7-fluoro-2-(3-pyridyl)quinazoline hydrochloride

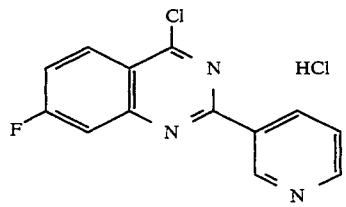

A suspension of the quinazolinone compound (1.2 g, prepared in Reference example 4) in 20 mL of thionyl chloride was heated to reflux for three hours. The excess of thionyl chloride was removed by distillation. The residue was distilled azeotropically with benzene (5 mL×3) and then reduced the total volume to about 5 mL. After cooling in refrigerator, precipitate was collected by filtration and washed with benzene twice to give the title compound (1.38 g) as a crystalline solid having the following physical data.

NMR (200 MHz, DMSO-d6): δ 7.80–7.95 (m, 2H), 8.07 (dd, 1H), 8.43–8.49 (m, 1H), 8.95 (d, 1H), 9.06 (dt, 1H), 9.65 (m, 1H).

The following compounds were obtained by the same procedure as Reference example 3→Reference example 4→ Reference example 5, by using the anthranilamide compound prepared in Reference example 2(a), 2(b) or 2(c), or being on sale, and the corresponding acid chloride.

Reference example 5(a)

4-chloro-6-methyl-2-(3-pyridyl)quinazoline hydrochloride

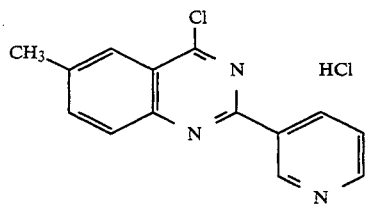

The product was collected by filtration as a white solid.

NMR (200 MHz, DMSO-d6): δ 2.62 (s, 3H), 7.96–8.14 (m, 4H), 8.98 (d, 1H), 9.16 (d, 1H), 9.63 (m, 1H).

Reference example 5(b)

4,6-dichloro-2-(3-pyridyl)quinazoline hydrochloride

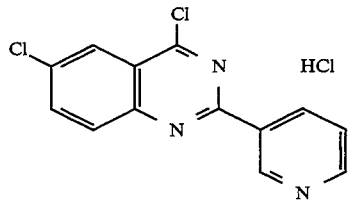

The product was collected by filtration as a white solid.

mp :210–214° C. NMR (CDCl₃): δ 7.28–8.17 (m, 3H), 8.35 (m, 1H), 8.89 (dd, 1H), 9.55 (dt, 1H), 9.98 (d, 1H).

Reference example 5(c)

4-chloro-6,7-dimethoxy-2-(3-pyridyl)quinazoline hydrochloride

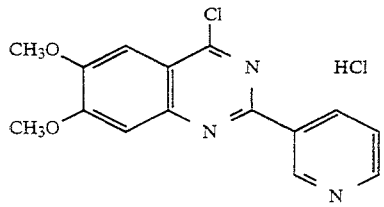

The product was collected by filtration as a white solid.

NMR (200 MHz, DMSO-d6): δ 4.04 (s, 3H), 4.06 (s, 3H), 7.46 (s, 1H), 7.56 (s, 1H), 7.95 (m, 1H), 8.93 (d, 1H), 9.09 (d, 1H), 9.60 (m, 1H).

Reference example 5(d)

4-chloro-2-(2-pyridyl)quinazoline

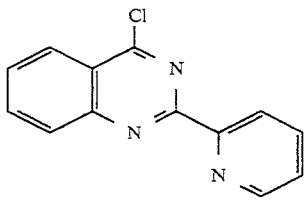

The product was collected by filtration as a light brown powder.

mp: 120°–121° C.

Reference example 5(e)

6-bromo-4-chloro-2-(3-pyridyl)quinazoline hydrochloride

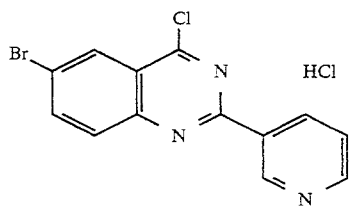

NMR (200 MHz, DMSO-d6): δ 8.02 (m, 1H), 8.14 (dd, 1H), 8.33 (dt, 1H), 8.50 (t, 1H), 9,01 (d, 1H), 9.14(d, 1H), 9.64 (t, 1H).

Reference example 6

2-[N-(3-pyridylcarbonyl)amino]benzamide

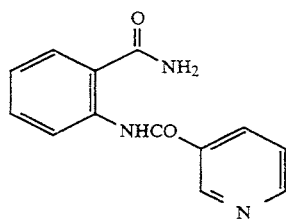

To a solution of anthranilamide (8.2 g, being on sale) and triethylamine (18.0 g)in 100 mL of tetrahydrofuran/methylene chloride (1:1), was added nicotinoyl chloride hydrochloride (10.8 g). The mixture was allowed to stir at room temperature, under nitrogen atmosphere, for six hours. The solution was then concentrated under reduced pressure. The concentrate was taken up in ethyl acetate and water and the mixture filtered. The solid material was triturated in ether and filtered to give the title compound (11.5 g) as a yellow powder having the following physical data.

mp :220°–222° C.

Reference example 7

2-(3-pyridyl)quinazolin-4-one

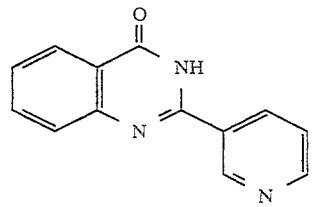

To a solution of the benzamide compound (11.5 g, prepared in Reference example 6) in 100 mL of toluene was added 95% sodium methoxide (5.7 g). The solution was heated at 60°–80° C. for three hours under nitrogen atmosphere. After cooling to room temperature, the solution was diluted with ammonium chloride solution. After stirring for one-half hour, the mixture was filtered. An NMR of the filtered material indicated the reaction was incomplete. The material was taken up in toluene and ethanol and 95% sodium methoxide (5.7 g) was added. The resulting solution was heated to reflux and stirred via a mechanical stirrer, under nitrogen atmosphere, overnight. The solvent had evaporated and the concentrate in the flask was collected and washed with ammonium chloride solution and methylene chloride. The solid material was collected by filtration and allowed to dry to give the title compound as a gray powder having the following physical data.

mp :275°–276° C. NMR (200 MHz, DMSO-d6): δ 7.50–7.61 (m, 2H), 7.75–7.90 (m, 2), 8.16 (d, 1H), 8.49 (m, 1H), 8.77 (d, 1H), 9.31 (s, 1H). IR (KBr): ν 3185 (w), 3045 (m), 2915 (w), 1677 (s), 1603 (m), 1558 (w), 1474 (m), 769 (m)cm⁻¹.

Reference example 8

4-chloro-2-(3-pyridyl)quinazoline

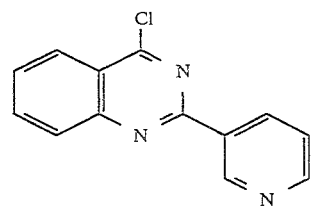

A solution of the quinazolinone compound (6.7 g, prepared in Reference example 7) and 5.7 mL of N,N-dimethylaniline in 200 mL of benzene was heated to reflux, under nitrogen atmosphere, for one-half hour with the removal of 15 mL of distillate. After cooling to room temperature, phosphorus oxychloride (4.5 g) was added and the resulting solution heated to reflux for six hours. After cooling to room temperature, the solution was washed with ice water and dilute sodium hydroxide solution. The organic extract was dried over sodium sulfate and concentrated under reduced pressure. The concentrate was triturated in ether and collected to give the title compound (3.0 g) having the following physical data.

mp: 178°–179° C.

The following compounds were obtained by the same procedure as Reference example 6→Reference example 7→Reference example 8, by using anthranilamide and the corresponding acid chloride.

Reference example 8(a)

4-chloro-2-( 4-pyridyl)quinazoline

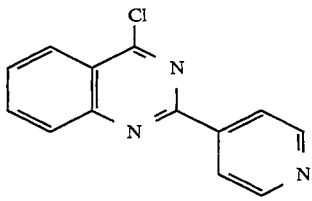

The product was collected by filtration as a brown solid.

mp: 158°–160° C.

Reference example 8(b)

4-chloro-2-( 2-chloro-5-pyridyl)quinazoline

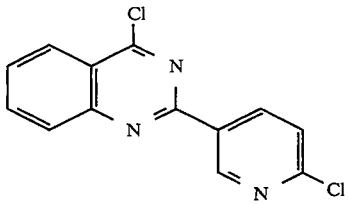

NMR (CDCl₃): δ7.47 (d, 1H), 7.73 (t, 1H), 7.95 (t, 1H), 8.05–8.32 (m, 2H), 8.81 (dd, 1H), 9.55 (ds, 1H).

Reference example 8(c)

4-chloro-2-(2-thienyl)quinazoline

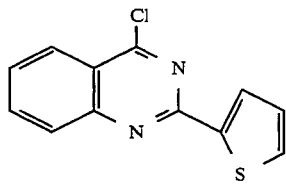

The product was collected by filtration as a tan powder.

mp: 121°–124° C.

Reference example 8(d)

4-chloro-2-(2-furyl)quinazoline

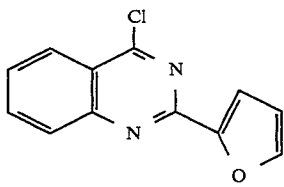

The product was collected by the filtration as a tan powder.

mp:116°–119° C.

Reference example 9

5-nitro-2-[N-(3-pyridylcarbonyl)amino]benzamide

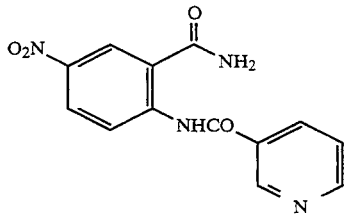

The title compound was obtained by the same procedure as Reference example 3, by using 5-nitroanthranilamide (prepared in Reference example 2 (d)).

The product was collected by filtration as a white solid.

NMR (200 MHz, DMSO-d6): δ 7.70 (m, 1H), 8.20 (broad, 1H), 8.35 (dt, 1H), 8.49 (dd, 1H), 8.85–8.92 (m, 3H), 9.15 (t, 1H).

Reference example 10

4-chloro-6-nitro-2-(3-pyridyl)quinazoline

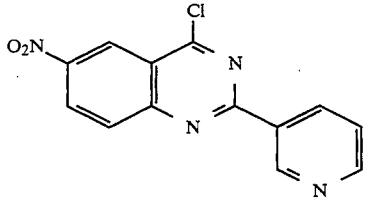

A suspension of the benzamide compound (0.925 g, prepared in Reference example 9) in phosphorous oxychloride (6 mL) was heated to reflux for 16 hours. After cooling to room temperature, the mixture was diluted by chloroform (30 mL) and then poured into 30 mL of ice-water mixture. The mixture was cooled in ice bath and carefully neutralized to pH 8 with a temperature control under 10° C. The aqueous layer was extracted with chloroform (50 mL×3). Combined organic layers were dried over with potassium carbonate and concentrated under reduced pressure to give the title compound (0.8 g) having the following physical data.

NMR (CDCl₃): δ 7.27–7.35 (m, 2H), 7.52 (dd, 1H), 8.46–8.63 (m, 3H), 8.87 (d, 1H), 9.42 (s, 1H).

EXAMPLE 1

4-phenylmethylamino-7-fluoro-2-(3-pyridyl)quinazoline

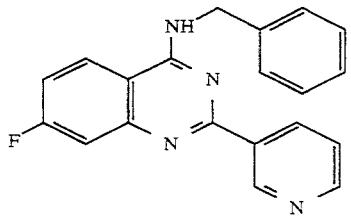

To a warm solution of the 4-chloroquinazoline compound (1.18 g, prepared in Reference example 5)in 50 mL ethanol was added phenylmethylamine (2.00 g). The mixture was heated to reflux for sixteen hours. The solution was then concentrated and the residue taken up in chloroform and ammonium chloride solution. The aqueous layer was extracted with chloroform (30 mL×3) and dried over sodium sulfate. After concentration, the residue was triturated in pentane/ether solution to give the title compound (0.88 g) as a pale white solid having the following physical data.

mp: 199°–203° C. NMR (CDCl$_3$): δ 5.00 (d, 2H), 6.01 (broad, 1H), 7.20 (td, 1H), 7.25–7.50 (m, 6H), 7.55 (dd, 1H), 7.70–7.77 (m, 1H), 8.70 (dd, 1H), 8.79 (dt, 1H), 9.74 (m, 1H). IR (KBr): ν 697 (s), 775 (s), 1166 (m), 1259 (m), 1341 (s), 1375 (s), 1444 (s), 1535 (s), 1592 (s), 1626 (s), 3135 (m), 3250 (m)cm$^{-1}$.

EXAMPLE 2

4-phenylmethylamino-7-fluoro-2-(3-pyridyl)quinazoline dihydrochloride

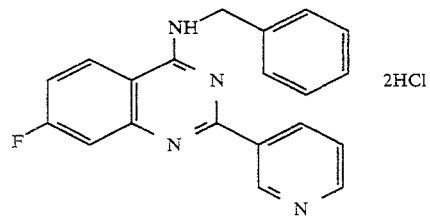

To a suspension of the free base (0.70 g, prepared in Example 1) in 10 ml methanol was added excess amount of HCl in methanol. The mixture was stirred at room temperature for a half of an hour. The solvent was removed and the residue was triturated in ether (30 ml). The title compound (0.84 g) as a white powder having the following physical data, was obtained after filtration.

mp: 250° C.

NMR (CDCl$_3$): δ 4.50 (d, 2H), 7.25–7.40 (m, 3H), 7.49–7.53 (m, 2H), 7.64 (dt, 1H), 7.82 (dd, 1H), 7.99 (m, 1H), 8.67 (m, 1H), 8.97 (dd, 1H), 9.15 (dd, 1H), 9.60 (d, 1H), 10.18 (broad, 1H). IR (KBr): ν 704 (m), 1266 (m), 1457 (s), 1574 (s), 1632 (s), 2920–2440 (broad, s), 3115 (broad, s) cm$^{-1}$.

EXAMPLE 3

The following compounds were obtained by the same procedure as Example 1, or Example 1 and Example 2, by using the corresponding 4-chloroquinazoline compound prepared by Reference example 5, 5(a) to 5(e) or Reference example 8, 8(a) to 8(d) and the proper amine.

EXAMPLE 3(a)

4-phenylmethylamino-6-methyl-2-(3-pyridyl)quinazoline and its salt

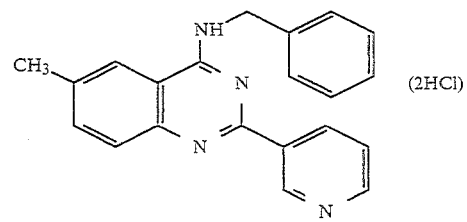

(free base)

The product was collected by filtration as a white solid.

mp: 179°–180° C. (dec.). NMR (CDCl$_3$): δ 5.03 (d, 2H), 5.97 (broad, 1H), 7.28–7.53 (m, 7H), 7.61 (dd, 1H), 7.86 (d, 1H), 8.69 (dt, 1H), 8.80 (dt, 1H), 9.76 (m, 1H). IR (KBr): ν 699 (w), 1365 (m), 1407 (w), 1437 (w), 1535 (s), 1569 (s), 1591 (s), 3200 (m) cm$^{-1}$.

(2HCl salt)

The product was collected by filtration as a white powder.

mp :265°–269° C. (dec.). NMR (CDCl$_3$): δ 2.50 (s, 3H), 5.03 (d, 2H), 7.28–7.42 (m, 3H), 7.48–7.53 (m, 2H), 7.80–7.91 (m, 2H), 8.06 (d, 1H), 8.45 (s, 1H), 8.91–9.00 (m, 2H), 9.5 (m, 1H). IR (KBr): ν 704 (w), 1388 (m), 1568 (s), 1593 (s), 1617 (s), 2400–3100 (broad, s), 3200 (m), 3410 (broad, m) cm$^{-1}$.

EXAMPLE 3(b)

4-phenylmethylamino-6-chloro-2-(3-pyridyl)quinazoline and its salt

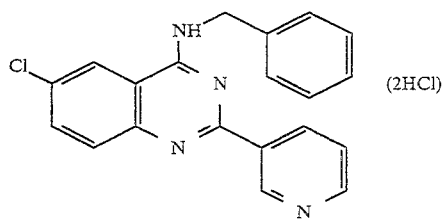

(free base)

The product was purified by column chromatography.

mp :240° C.

NMR (CDCl$_3$): δ 5.00 (d, 2H), 5.92 (broad, 1H), 7.32–7.51 (m, 6H), 7.71 (m, 2H), 7.90 (d, 1H), 8.71 (dd, 1H), 8.79 (dt, 1H), 9.75 (d, 1H). IR (KBr): ν 697 (m), 1368 (s), 1419 (m), 1439 (m), 1534 (s), 1568 (s), 1590 (s), 3260 (w) cm$^{-1}$.

(2HCl salt)

The product was collected by filtration as a white powder.

mp: 255° C. (dec.). NMR (CDCl$_3$): δ 4.99 (d, 2H), 7.25–7.42 (m, 3H), 7.45–7.55 (m, 2H), 7.96–8.10 (m, 3H), 8.72 (m, 1H), 8.96 (d, 1H), 9.15 (d, 1H), 9.60 (m, 1H). IR (KBr):δ 671 (w), 709 (m), 1356 (m), 1387 (s), 1457 (m), 1488 (m), 1518 (s), 1569 (s), 1608 (s), 1631 (s), 2335–2890 (broad, s), 3825 (s), 3230 (m), 3425 (m) cm$^{-1}$.

EXAMPLE 3(c)

4-phenylmethylamino-6,7-dimethoxy-2-(3-pyridyl)-quinazoline and its salt

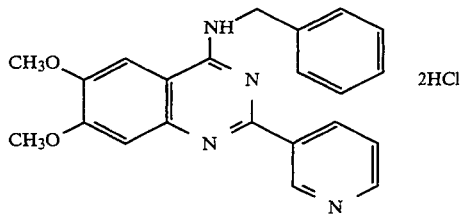

(free base)

The product was collected by filtration as a white solid.

mp: 193°–196° C. NMR (200 MHz, DMSO-d6): ,5 3.92 (s, 3H), 3.94 (s, 3H), 4.92 (d, 2H), 6.90 (broad, 1H), 7.23–7.38 (m, 4H), 7.46–7.55 (m, 3H), 7.76 (s, 1H), 8.62–8.78 (m, 3H), 9.52 (m, 1H). IR (KBr): ν 698 (m), 850 (m), 1026 (m), 1131 (m), 1183 (m), 1213 (s), 1243 (s), 1366 (s), 1450 (s), 1501 (s), 1528 (s), 1591 (s), 1622 (m), 3270 (w) cm$^{-1}$.

(2HCl salt)

The product was collected by filtration as a white solid.

mp: 240° C. (dec.). NMR (200 MHz, DMSO-d6): <5 3.98 (s, 6H), 5.01–5.06 (m, 2H), 7.25–7.41 (m, 3H), 7.74 (s, 1H), 7.85 (m, 1H), 8.14 (s, 1H), a.90–8.95 (m, 2H), 9.56 (m, 1H). IR (KBr): ν 1243 (w), 1287 (s), 1378 (m), 1473 (m), 1 504 (s), 1542 (m), 1596 (m), 1634 (s), 2400–3200 (broad, s), 3440 (broad, s) cm$^{-1}$.

EXAMPLE 3(d)

4-phenylmethylamino-2-(2-pyridyl)quinazoline and its salt

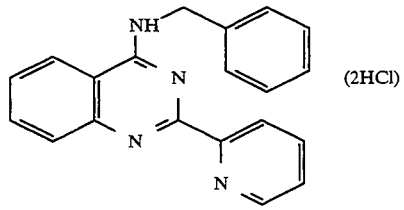

(free base):
The product was collected by filtration as a tan solid.
mp: 165°–169° C.
(2HCl salt)
mp: 140°–155° C. NMR (200 MHz, DMSO-d6): δ 5.12 (d, 2H), 7.35 (m, 3H), 7.58 (d, 2H), 7.83 (qd, 2H), 8.07 (t, 1H), 8.19–8.36 (m, 2H), 8.64 (d, 1H), 8.82 (d, 1H), 8.93 (d, 1H), 11.40 (t, 1H). IR (KBr): ν 3370 (m), 3220 (m), 3200–2700 (m), 1625 (s), 1562 (m), 1524 (m), 1466 (m), 1385 (m), 765 (m) cm$^{-1}$.

EXAMPLE 3(e)

4-phenylmethylamino-2-(3-pyridyl)quinazoline and its salt

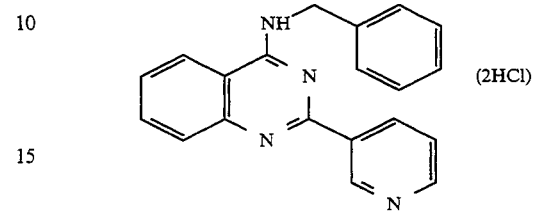

(free base)
mp: 137°–138° C. NMR (CDCl3): <3 5.01 (d, 2H), 6.20 (t, 1H), 7.26–7.49 (m, 6H), 7.71–7.79 (t, 3H), 7.95 (d, 1H), 8.68 (bs, 1H), 8.82 (d, 1H), 9.75 (bs, 1H). IR (KBr): ν 3305 (m), 1584 (s), 1520 (s), 1437 (m), 1410 (m), 1365 (s), 1325 (w), 765 (m), 694 (m) cm$^{-1}$.

(2HCl salt)

mp :225°–235° C. NMR (200 MHz, DMSO-d6): δ 5.05 (d, 2H), 7.22–7.43 (m, 3H), 7.52 (m, 2H), 7.78 (t, 1H), 7.94–8.13 (m, 2H), 8.36 (s, 1H), 8.78 (d, 1H), 9.00 (dd, 1H), 9.12 (dd, 1H), 9.70 (s, 1H), 11.16 (broad t, 1H). IR (KBr): ν 3300–2615 (broad,s), 1629 (s), 1605 (s), 1569 (s), 1456 (m), 1384 (m), 763 (m), 705 (m)cm$^{-1}$.

EXAMPLE 3(f)

4-phenylamino-2-(3-pyridyl)quinazoline

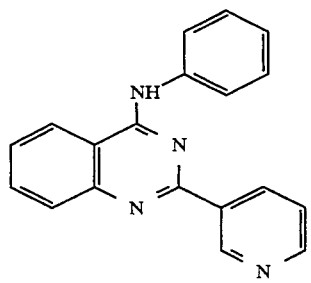

The product was collected by filtration as a yellow powder.

mp: 173°–178° C. NMR (200 MHz, DMSO-d6): δ 7.29 (t, 1H), 7.53 (t, 2H), 7.72–8.17 (m, 6H), 8.80 (d, 1H), 8.93 (d, 1H), 9.05 (d, 1H), 9.52 (s, 1H), 10.81 (bs, 1H). IR (KBr): ν 3160 (bw), 1559 (s), 1520 (s), 1411 (m), 1363 (m), 754 (m) cm$^{-1}$.

EXAMPLE 3(g)

4-(3-methoxycarbonylphenyl)amino-2-(3-pyridyl)-quinazoline

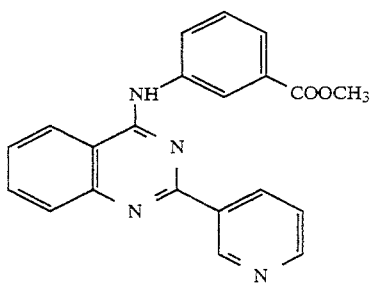

The product was collected by filtration as a yellow powder.

mp: 228°–245° C. NMR (200 MHz, DMSO-d6): δ 3.94 (s, 3H), 7.56–8.04 (m, 7H), 8.72–9.08 (m, 4H), 9.57 (s, 1H), 10.61 (bs, 1H). IR (KBr): ν 3400 (bw), 1717(m), 1562 (s), 1520 (m), 1447 (m), 1374 (m), 1299 (m), 1278(m), 752 (m), 672 (w)cm$^{-1}$.

EXAMPLE 3(h)

4-(4-carboxyphenylmethyl)amino-2-(3-pyridyl)quinazoline

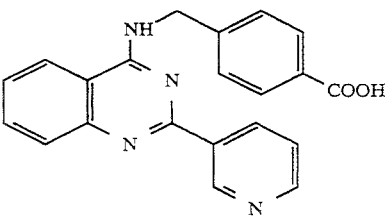

mp: 285°–294° C. NMR (200 MHz, DMSO-d6): δ 4.98 (d, 2H), 7.50–7.62 (m, 4H), 7.81 (d, 2H), 7.90 (d, 2H), 8.37 (d, 1H), 8.65 (m, 2H), 9.13 (t, 1H), 9.49 (s, 1H). IR (KBr): ν 3340 (broad), 1747 (m), 1586 (s), 1531 (s), 1366 (m), 765 (m) cm$^{-1}$.

EXAMPLE 3(i)

4-(2-thienylmethyl)amino-2-(3-pyridyl)quinazoline and its salt

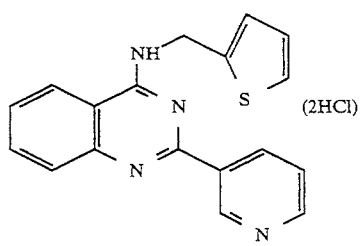

(free base)
mp: 195°–197° C. NMR (200 MHz, DMSO-d6): δ 5.08 (d, 2H), 6.99 (m, 1H), 7.19 (m, 1H), 7.35 (dd, 1H), 7.55 (m, 2H), 8.30 (s, 1H), 8.69 (m, 1H), 8.83 (m, 1H), 9.13 (t, 1H). IR (KBr): ν 3260 (bw), 1583 (s), 1525 (s), 1449 (m), 1359 (s), 763 (m), 747 (m), 720 (m) cm$^{-1}$
(2HCl salt)
mp: 255° C. (dec.). NMR (200 MHz, DMSO-d6): <5 5.20 (d, 2H), 7.01 (m, 1H), 7.22 (m, 1H), 7.43 (s, 1H), 7.77 (t, 1H), 8.00 (m, 3H), 8.21 (d, 1H), 8.61 (d, 1H), 8.99 (d, 1H), 9.23 (d, 1H), 9.74 (s, 1H), 10.45 (bs, 1H). IR (KBr): ν 3405 (w), 3060–2615 (broad, m), 2363 (w), 1631 (s), 1608 (s), 1570 (s), 1458 (m), 1387 (m), 773 (m), 712 (m)cm$^{-1}$.

EXAMPLE 3(j)

4-(3-chlorophenylmethyl)amino-2-(3-pyridyl)quinazoline and its salt

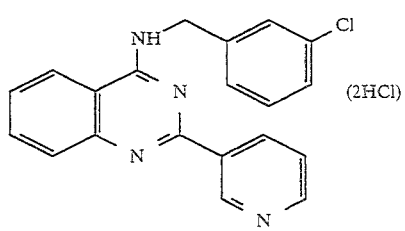

(free base)
mp: 203°–205° C. NMR (200 MHz, DMSO-d6): <5 4.92 (d, 2H), 7.27–7.61 (m, 6H), 7.82 (d, 2H), 8.33 (d, 1H), 8.66 (m, 2H), 9.08 (t, 1H), 9.53 (s, 1H). IR (KBr): ν 3245 (w), 3050–2800 (w), 1586 (s), 1533 (m), 1436 (w), 1412 (w), 1366 (m), 765 (w) cm$^{-1}$.
(2HCl salt)
mp: 235°–250° C. NMR (200 MHz, DMSO-d6): ,5 5.05 (d, 2H), 7.35 (m, 2H), 7.49 (m, 1H), 7.62 (s, 1H), 7.78 (t, 1H), 7.90–8.12 (m, 2H), 8.28 (s, 1H), 8.97 (m, 1H), 9.13 (dd, 1H), 9.66 (s, 1H), 10.97 (bs, 1H). IR (KBr): ν 3035 (m), 2900–2700 (m), 1634 (m), 1610 (m), 1569 (m), 1387 (w), 780 (w), 71 0 (w) cm$^{-1}$.

EXAMPLE 3(k)

4-(3-pyridylmethyl)amino-2-(3-pyridyl)quinazoline and its salt

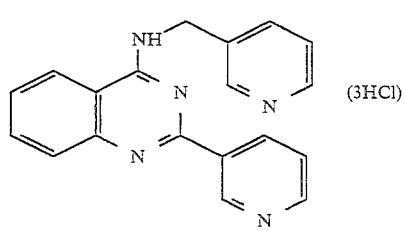

(free base)
mp: 157°–161° C. NMR (200 MHz, DMSO-d6): δ 4.95 (d, 2H), 7.33 (m, 1H), 7.55 (m, 2H), 7.85 (m, 3H), 8.33 (d, 1H), 8.46 (dd, 1H), 8.65–8.76 (m, 3H), 9.10 (t, 1H), 9.57 (s, 1H). IR (KBr): ν 3255 (m), 3050–2900 (w), 1586 (s), 1533 (s), 1438 (m), 368 (s), 763 (m), 700 (m)cm$^{-1}$.
(3HCl salt)
mp: 240°–257° C. NMR (200 MHz, DMSO-d6): δ 5.25 (d, 2H), 7.77 (t, 1H), 8.07 (m, 2H), 8.29 (d, 1H), 8.83 (m, 4H), 9.00 (d, 1H), 9.19 (m, 2H), 9.69 (s, 1H), 11.25 (bs, 1H). IR (KBr):δ 3500 (w), 3100–2500 (broad, m), 1633 (s), 1611(s), 1569 (m), 1542 (m), 1457 (w), 790 (w), 720 (w) cm$^{-1}$.

EXAMPLE 3(l)

4-(3,4-dimethoxyphenylmethyl)amino-2-(3-pyridyl)-quinazoline and its salt

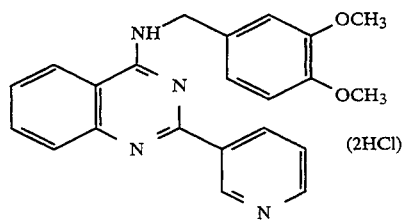

(2HCl)

(free base)

mp: 155°–159° C. NMR (200 MHz, DMSO-d6): δ 3.71 (d, 6H), 4.85 (d, 2H), 6.83–7.05 (m, 2H), 7.18 (s, 1H), 7.54 (m, 2H), 7.82 (d, 2H), 8.32 (d, 1H), 8.68 (dd, 1H), 8.77 (dd, 1H), 9.01 (t, 1H), 9.63 (s, 1H). IR (KBr): ν 3395 (w), 3200–2900 (w), 1584 (s), 1514 (s), 1364 (m), 1263 (m), 1025 (m), 764 (w) cm$^{-1}$.

(2HCl salt)

mp: 21 5°–220° C.

NMR (200 MHz, DMSO-d6): δ 3.70 (s, 6H), 4.97 (d, 2H), 6.90 (d, 1 H), 7.02 (d, 1H), 7.24 (s, 1H), 7.77 (t, 1H), 7.92 (m, 1H), 8.04 (t, 1H), 8.73 (d, 1H), 8.97 (d, 1H), 9.16 (dd, 1H), 9.70 (s, 1H), 10.94 (bs, 1H). IR (KBr): ν 3404 (m), 3200–2300 (m), 1631 (s), 1610 (s), 1569 (s), 1514 (s), 1264 (m), 765 (m) cm$^{-1}$

EXAMPLE 3(m)

4-phenylethylamino-2-(3-pyridyl)quinazoline and its salt

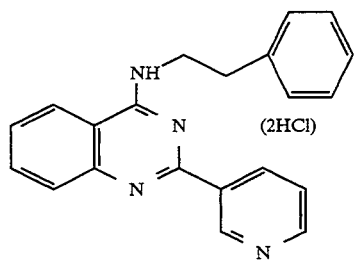

(2HCl)

(free base)

mp: 136°–139° C. NMR (200 MHz, DMSO-d6): δ 3.07 (t, 2H), 3.89 (q, 2H), 7.20–7.30 (m, 3H), 7.32 (d, 2H), 7.55 (m, 2H), 7.82 (s, 2H), 8.26 (s, 1H), 8.59 (t, 1H), 8.70 (m, 2H), 9.65 (s, 1H). IR (KBr): ν 3290 (m), 3050–2900 (w), 1591 (s), 1514 (s), 1534 (s), 1442 (m), 1370 (s), 761 (m), 702 (m) cm$^{-1}$.

(2HCl salt)

mp:220°–250° C. (dec.). NMR (200 MHz, DMSO-d6): ,δ 3.11 (t, 2H), 4.05 (q, 2H), 7.15–7.38 (m, 5H), 7.77 (t, 1H), 8.01 (m, 2H), 8.35 (d, 1H), 8.70 (d, 1H), 9.01 (d, 1H), 9.15 (d, 1H), 9.69 (s, 1H), 10.68 (bs, 1H). IR (KBr): ν 3400 (w), 3100–2500 (m), 1633 (s), 1613 (s), 1570 (m), 1457 (m), 1385 (m), 790 (w), 720 (w) cm$^{-1}$.

EXAMPLE 3(n)

4-(3-trifluoromethylphenylmethyl)amino-2-(3-pyridyl)-quinazoline dihydrochloride

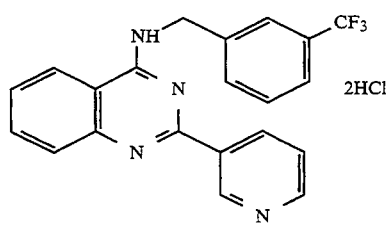

2HCl mp :>280° C. NMR (200 MHz, DMSO-d6): ,δ 5.14 (d, 2H), 7.52–8.35 (m, 8H), 8.70–9.20 (m, 3H), 9.67 (m, 1H).

EXAMPLE 3(o)

4-(4-(N,N-dimethylamino)phenylmethyl)amino-2-(3-pyridyl)quinazoline trihydrochloride

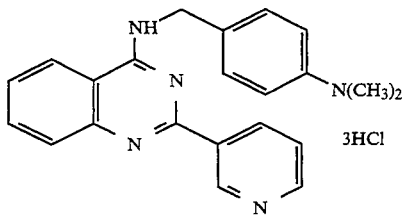

3HCl mp: 200°–250° C. (dec.). NMR (200 MHz, DMSO-d6): δ 3.04 (s, 6H), 5.05 (d, 2H), 7.50–8.30 (m, 8H), 8.72 (s, 1H), 8.92–9.12 (m, 2H), 9.60 (m, 1H).

EXAMPLE 3(p)

4-(4-sulfamoylphenylmethyl)amino-2-(3-pyridyl)-quinazoline dihydrochloride

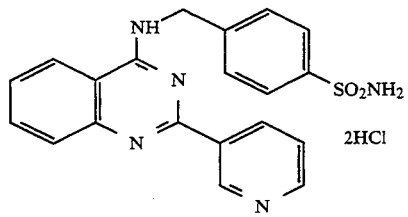

2HCl mp: 255°–265° C. NMR (200 MHz, DMSO-d6): <δ 5.10 (d, 2H), 7.32 (bs, 2H), 7.66–8.20 (m, 8H), 8.62 (d, 1H), 8.95 (m, 2H), 9.56 (ms, 1H).

EXAMPLE 3(q)

4-phenylmethylamino-2-(4-pyridyl)quinazoline and its salt

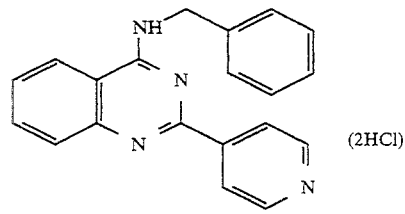

(2HCl)

(free base)
mp: 195°–197° C. NMR (200 MHz, DMSO-d6): δ 4.96 (d, 2H), 7.19–7.66 (m, 6H), 7.83 (d, 2H), 8.30 (d, 2H), 8.39 (d, 1H), 8.72 (d, 2H), 9.10 (t, 1H). IR (KBr):δ 3250 (w), 1585 (s), 1561 (s), 1529 (s), 1411 (m), 1374 (s), 1325 (s), 768 (m), 702 (m) cm$^{-1}$.

(2HCl salt):
mp: 260°–270° C. NMR (200 MHz, DMSO-d6): δ 5.02 (d, 2H), 7.22–7.40 (m, 3H), 7.51 (d, 2H), 7.75 (t, 1H), 8.00 (t, 1H), 8.16 (d, 1H), 8.66 (d, 1H), 8.81 (d, 2H), 9.06 (d, 2H), 10.32 (bs, 1H). IR (KBr): ν 3385 (m), 3210 (m), 3060–2600 (s), 1627 (s), 1604 (s), 1567 (s), 1505 (m), 1452 (m), 1383 (m), 760 (m), 709 (m) cm$^{-1}$.

EXAMPLE 3(r)

4-phenylamino-2-(4-pyridyl)quinazoline

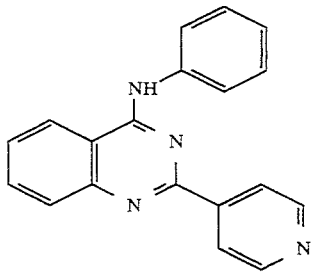

mp: 270°–274° C. NMR (200 MHz, DMSO-d6): δ 7.22 (t, 1H), 7.70 (m, 1H), 7.94 (m, 4H), 8.37 (m, 2H), 8.68 (d, 1H), 8.82 (d, 2H), 10.13 (s, 1H). IR (KBr): ν 3270 (m), 3145 (m), 1620 (s), 1572 (s), 1524 (s), 1488 (s), 1443 (s), 1414 (s), 1374 (s), 749 (m), 702 (m) cm$^{-1}$.

EXAMPLE 3(s)

4-phenylmethylamino-2-(2-chloro-5-pyridyl)quinazoline

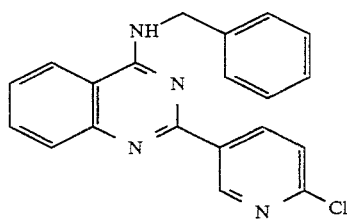

mp: 212°–214° C. NMR (CDCl3): δ 4.96 (d, 2H), 6.03 (bs, 1H), 7.20–7.55 (m, 7H), 7.66–7.95 (m, 3H), 8.78 (m, 1H), 9.52 (m, 1H). IR (KBr): ν 3315 (w), 1580 (s), 1532 (ms), 1446 (mw), 1343 (m), 1269 (w) cm$^{-1}$.

EXAMPLE 3(t)

4-phenylmethylamino-2-(2-thienyl)quinazoline

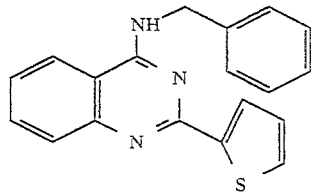

mp: 158°–163° C. NMR (200 MHz, DMSO-d6): δ 4.88 (d, 2H), 7.14–7.53 (m, 6H), 7.62–7.81 (m, 3H), 7.92 (m, 1H), 8.30 (d, 1H), 8.97 (t, 1H). IR (KBr):δ 3305 (w), 1571 (s), 1519 (s), 1451 (m), 1408 (m), 1377 (s), 769 (m), 730 (m), 737 (m) cm$^{-1}$.

EXAMPLE 3(u)

4-phenylamino-2-(2-thienyl)quinazoline

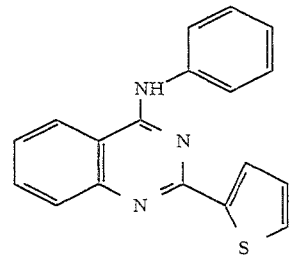

mp: 137°–139° C. NMR (200 MHz, DMSO-d6): δ 7.20 (m, 2H), 7.62–8.09 (m, 9H), 8.58 (d, 1H), 9.85 (s, 1H). IR (KBr): ν 3430 (w), 1616 (w), 1662 (w), 1561 (s), 1461 (m), 1488 (m), 1461 (m), 1406 (m), 1374 (m), 749 (w)cm$^{-1}$.

EXAMPLE 3(v)

4-phenylmethylamino-2-(2-furyl)quinazoline

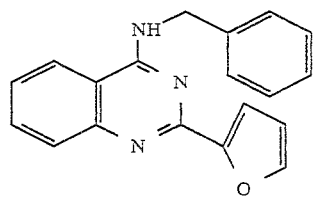

mp: 152°–154° C. NMR (CDCl3): δ 4.95 (d, 2H), 6.00 (t, 1H), 6.56 (m, 1H), 7.31–7.49 (m, 7H), 7.62–7.76 (m, 3H), 7.97 (d, 1H). IR (KBr): ν 3290 (m), 1589 (m), 1531(s), 1365 (s), 1015 (m), 890 (m), 762 (s) cm$^{-1}$.

EXAMPLE 3(w)

4-phenylamino-2-(2-furyl)quinazoline

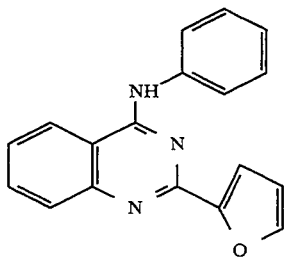

mp: 183°–184° C. NMR (CDCl₃): δ 6.58 (m, 1H), 7.13–7.37 (m, 2H), 7.39–7.58 (q, 4H), 7.65 (s, 1H), 7.72–7.94 (m, 4H), 8.03 (d, 1H). IR (KBr): ν 3456 (w), 1607 (m), 1559 (s), 1524 (s), 1485 (s), 1446 (m), 1419 (m), 1360 (m), 748 (m) cm⁻¹.

EXAMPLE 3(x)

6-chloro-4-(2-(1-methyl-2-pyrrolyl)ethyl)amino-2-(3-pyridyl)quinazoline and its salt

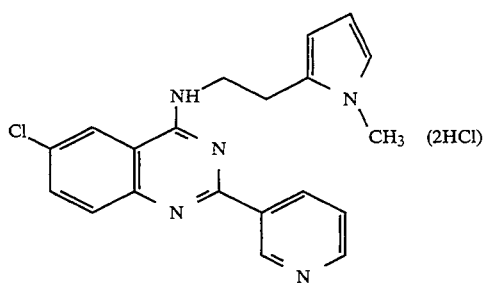

(free base)

The product was collected by filtration as a white solid.

NMR (200 MHz, DMSO-d6): <δ 2.99 (t, 2H), 3.58 (s, 3H), 3.89 (q, 2H), 5.90 (m, 2H), 6.62 (m, 1H), 7.55 (m, 1H), 7.83 (m, 2H), 8.44 (d, 1H), 8.70–8.75 (m, 3H), 9.61 (m, 1H).

(2HCl salt)

The product was collected by filtration as a white powder.

mp: 190°–194° C. (dec.). NMR (200 MHz, DMSO-d6): δ 3.02 (t, 2H), 3.58 (s, 3H), 3.97 (q, 2H), 5.88 (m, 2H), 6.60 (t, 1H), 7.97–8.14 (m, 2H), 8.16 (d, 1H), 8.74 (d, 1H), 8.99 (dd, 1H), 9.16 (d, 1H), 9.63 (d, 1H), 10.00 (broad, 1H). IR (KBr): ν 711 (w), 709 (m), 1359 (m), 1388 (s), 1438 (m), 1549 (s), 1570 (s), 1599 (s), 1634 (s), 2065 (m), 2365 (m), 2555 (s), 3110 (m), 3360 (m) cm⁻¹.

EXAMPLE 3(y)

4-phenylmethylamino-6-bromo-2-(3-pyridyl)quinazoline and its salt

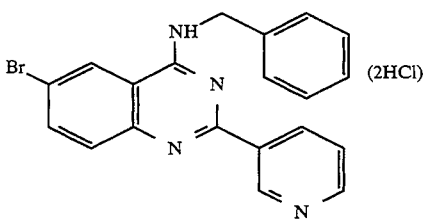

(free base)

The product was collected by filtration as a solid.

NMR (200 MHz, DMSO-d6): <δ 4.90 (d, 2H), 7.25–7.56 (m, 6H), 7.75 (d, 2H), 7.94 (dd, 1H), 8.66–8.71 (m, 3H), 9.18 (broad, 1H), 9.54 (d, 1H).

(2HCl salt)

mp: 233°–240° C. (dec.). NMR (200 MHz, DMSO-d6): <δ 4.99 (d, 2H), 7.25–7.42 (m, 3H), 7.51–7.57 (m, 3H), 7.96–8.03 (m, 1H), 8.07–8.10 (m, 2H), 8.93–9.00 (m, 2H), 9.19 (d, 1H), 9.62 (d, 1H), 10.30 (broad, 1H). IR (KBr): ν 701 (m), 1357 (m), 1404 (s), 1446 (m), 1519 (s), 1549 (s), 1628 (s), 2400–3000 (broad, s), 3140 (s) cm⁻¹.

EXAMPLE 3(z)

4-phenylmethylamino-6-nitro-2-(3-pyridyl)quinazoline and its salt

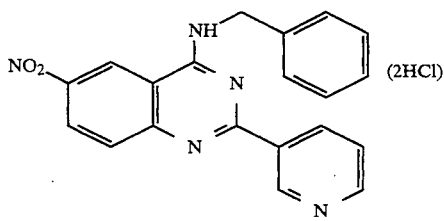

(free base)

The product was collected by filtration as a solid.

NMR (200 MHz, DMSO-d6): δ 4.95 (d, 2H), 7.25–7.40 (m, 3H), 7.48–7.58 (m, 3H), 7.93 (dd, 1H), 8.50 (dt, 1H), 8.70–8.80 (m, 2H), 9.46 (d, 1H), 9.58 (d, 9.70 (broad, 1H).

(2HCl salt)

mp: 289°–292° C. (dec.). NMR (200 MHz, DMSO-d6): δ 5.00 (d, 2H), 7.25–7.42 (m, 3H), 7.51–7.55 (m, 2H), 8.04–8.09 (m, 2H), 8.59 (dt, 1H), 9.00 (dd, 1H), 9.27 (d, 1H), 9.54 (d, 1H), 9.67 (s, 1H), 10.18 (broad, 1H). IR (KBr): ν 671 (m), 709 (m), 757 (m), 784 (m), 1349 (s), 1514 (s), 1578 (s), 1636 (s), 2445 (broad, s), 2860 (w), 3070 (m) cm⁻¹.

EXAMPLE 3(aa)

4-(cyclopropylmethyl)amino-2-(3-pyridyl)quinazoline and its salt

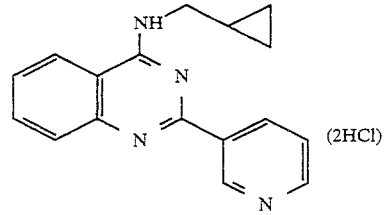

(free base)

mp: 162°–163° C. NMR (200 MHz, DMSO-d6): δ 0.38 (m, 2H), 0.49 (m, 2H), 1.33 (m, 1H), 3.58 (t, 2H), 7.55 (m, 2H), 7.79 (m, 2H), 8.32 (d, 1H), 8.56 (t, 1H), 8.69 (m, 2H), 9.62 (s, 1H). IR(KBr):δ 3265(w), 1537 (s), 1525 (s), 1437 (w), 1369 (s), 762 (m) cm⁻¹.

(2HCl salt)

mp: 230°–239° C. NMR (200 MHz, DMSO-d6): ,5 0.43 (m, 2H), 0.50 (m, 2H), 1.32 (m, 1H), 3.71 (t, 2H), 7.78 (t, 1H), 7.93 (m, 1H), 8.05 (t, 1H), 8.34 (d, 1H), 8.77 (d, 1H), 8.99 (d, 1H), 9.08 (dd, 1H), 9.68 (s, 1H), 10.68 (bs, 1H). IR (KBr): ν 3405-2700 (broad, s), 2365 (w), 1632 (s), 1600 (s), 1570 (m), 1542 (m), 1458 (w), 1383 (m), 1321 (w), 767 (w), 669 (w) cm⁻¹.

EXAMPLE 3(bb)

4-(3-methylphenylmethyl)amino-2-(3-pyridyl)quinazoline and its salt

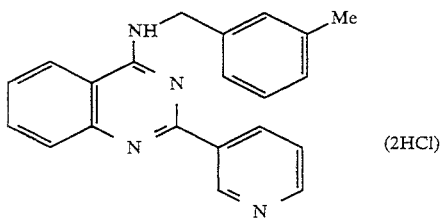

(free base)

mp: 166°–169° C. NMR (200 MHz, DMSO-d6): δ 2.28 (s, 3H), 4.90 (s, 2H), 7.03 (bd, 1H), 7.18-7.32 (m, 3H), 7.47-7.61 (m, 2H), 7.81 (d, 1H), 8.35 (d, 1H), 8.69 (m, 2H), 9.02 (bt, 1H), 9.58 (s, 1H). IR (KBr): ν 3245 (m), 1567 (s), 1533 (s), 1438 (m), 1443 (m),1368 (s), 1326 (m), 762 (m), 699 (m)cm⁻¹.

(2HCl salt)

mp: 225°–244° C. NMR (200 MHz, DMSO-d6): <5 2.29 (s, 3H), 5.03 (s, 2H), 7.10 (d, 1H), 7.20-7.38 (m, 3H), 7.77 (t, 1H), 7.92-8.10 (m, 2H), 8.34 (d, 1H), 8.76 (d, 1H), 9.02 (d, 2H), 9.20 (d, 2H), 9.69 (s, 1H), 11.05 (bt, 1H). IR (KBr): ν 3400 (m), 3050-2600 (broad, m), 1627 (s), 1570 (s), 1542 (m), 1457 (m), 1385 (m), 770 (m), 680 (m) cm⁻¹

EXAMPLE 3(cc)

4-(2-(1-methyl-2-pyrrolyl)ethyl)amino-2-(3-pyridyl)-quinazoline

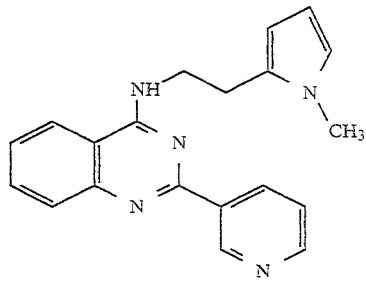

mp: 140°–142° C. NMR (200 MHz, DMSO-d6): δ 3.00 (t, 2H), 3.58 (s, 3H), 3.88 (qd, 2H), 5.91 (m, 2H), 6.63 (t, 1H), 7.53 (m, 2H), 7.80 (d, 2H), 8.24 (d, 1H), 8.59 (t, 1H), 8.79 (m, 2H), 9.62 (s, 1H). IR (KBr): ν 3445 (m), 3130-2900 (w), 2369 (w), 1567 (s), 1514 (s), 1533 (s), 1443 (m), 1438 (m), 1368 (s), 1351 (m), 1187 (w), 762 (m), 699 (m) cm⁻¹.

EXAMPLE 3(dd)

4-(3-nitrophenylmethyl)amino-2-(3-pyridyl)quinazoline and its salt

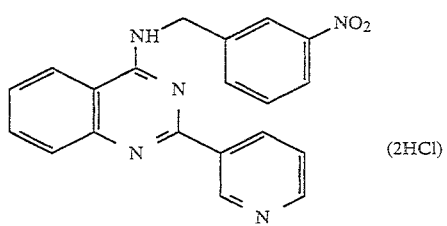

(free base)

mp: 21 8°–220° C. NMR (200 MHz, DMSO-d6): δ 5.05 (d, 2H), 7.46-7.69 (m, 3H), 7.83 (m, 2H), 7.84 (d, 1H), 8.13 (d, 1H), 8.37 (m, 2H), 8.67 (m, 2H), 9.18 (t, 1H), 9.52 (s, 1H).

(2HCl salt)

mp: 263°–265° C. NMR (200 MHz, DMSO-d6): δ 5.15 (d, 2H), 7.60-7.86 (m, 3H), 7.90-8.19 (m, 5H), 8.26 (d, 1H), 8.43 (s, 1H), 8.75 (d, 1H), 9.00 (d, 1H), 9.18 (d, 1H), 9.65 (s, 1H), 11.03 (bs, 1H).

EXAMPLE 3(ee)

4-(5-methyl-3-isoxazolyl)amino-2-(3-pyridyl)quinazoline and its salt

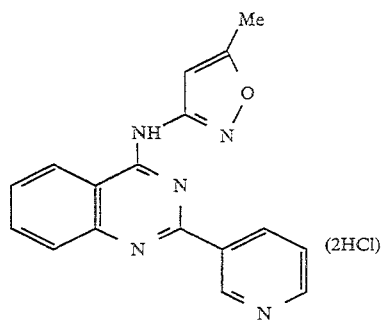

(free base)

NMR (200 MHz, DMSO-d6): δ 2.28 (s, 3H), 7.64 (s, 1H), 7.52–7.71 (m, 2H), 7.95 (m, 2H), 8.72 (m, 4H), 9.68 (m, 1H), 10.98 (s, 1H).

(2HCl salt)

mp: 228°–230° C. NMR (200 MHz, DMSO-d6): δ 2.53 (s, 3H), 7.09 (s, 1H), 7.74 (m, 1H), 8.04 (m, 2H), 8.18 (m, 1H), 8.75 (d, 1H), 9.06 (d, 1H), 9.34 (d, 1H), 9.64 (s, 1H).

The following compounds were obtained by the same procedure as described in Reference examples 2, 3, 4 and 5 and examples 1 and 2 or in Reference example 6, 7 and 8 and examples 1 and 2, by using isatoic anhydride.

EXAMPLE 3(ff)

6-iodo-4-phenylmethylamino-2-(3-pyridyl)quinazoline dihydrochloride

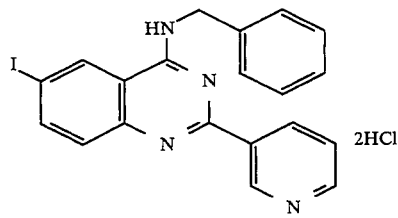

mp:205°–10° C., (dec.) NMR (200 MHz, DMSO-d6) δ: 5.00 (d, 2H), 7.28–7.41 (m, 3H), 7.47–7.53 (m, 2H), 7.80 (d, 1H), 7.95 (m, 1H), 8.23 (dd, 1H), 8.92–8.98 (m, 2H), 9.08 (d, 1H), 9.59 (m, 1H), 10.00 (broad, 1H).

EXAMPLE 3(gg)

6-fluoro-4-phenylmethylamino-2-(3-pyridyl)quinazoline dihydrochloride

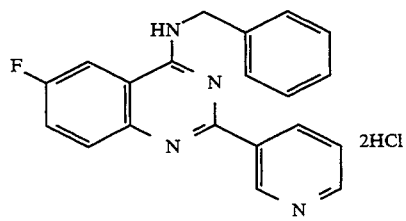

mp: 200°–2° C., (dec.) NMR (200 MHz, DMSO-d6) δ: 5.02 (d, 2H), 7.28–7.41 (m, 3H), 7.51–7.54 (m, 2H), 7.82–8.02 (m, 2H), 8.07–8.20 (m, 1H), 8.40–8.52 (d, 1H), 8.97 (dd, 1H), 9.15 (d, 1H), 9.61 (s, 1H), 10.08 (broad, 1H).

EXAMPLE 3(hh)

4-(3-carboxyphenyl)amino-2-(4-pyridyl)quinazoline

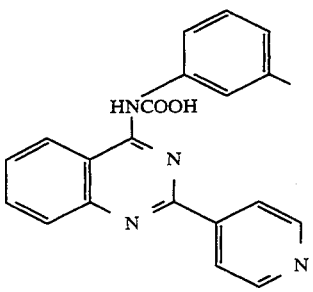

mp: >300° C. NMR (200 MHz, DMSO-d6) δ:7.65 (t, 1H), 7.78 (m, 2H), 7.99 (d, 2H), 8.22 (d, 1H), 8.68 (d, 2H), 8.75 (d, 1H), 8.87 (m, 3H), 10.44 (s, 1H). IR (KBr)ν: 3370–2800 (w, broad), 1712 (m), 1632 (m), 1571 (s), 1545 (s), 1473 (m), 1437 (m), 1376 (m), 764 (m) cm$^{-1}$.

EXAMPLE 4

6-acetylamino-4-phenylmethylamino-2-(3-pyridyl)-quinazoline

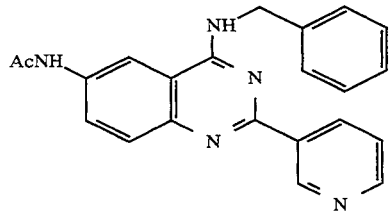

To warmed suspension of the nitroquinazoline compound (141 mg, prepared in Example 3(z)) in acetic acid (4 mL) was added zinc dust (80 mg). The red mixture was heated to reflux for overnight. After cooling down to room temperature the precipitate was removed by filtration. The filtrate was neutralized to pH 8 and extracted with chloroform. The insoluble solid was removed by filtration during the extraction. The chloroform was dried over potassium carbonate and then concentrated to 0.5 mL (total volume). The precipitate was collected by filtration to give the title compound (20 mg) having the following physical data.

mp: 127° C. (dec.). NMR (200 MHz, DMSO-d6): δ 2.12 (s, 3H), 4.88 (d, 2H), 7.22–7.37 (m, 3H), 7.45–7.53 (m, 2H), 7.75 (m, 1H), 8.32 (m, 2H), 8.58–8.69 (m, 3H), 8.94 (broad 1H), 9.52 (m, 1H), 10.23 (broad, 1H). IR (KBr): ν 700 (w), 840 (w), 1318 (m), 1368 (m), 1426 (m), 1537 (s), 1584 (s), 1676 (m), 3065 (m), 3365 (m) cm$^{-1}$.

Reference Example 11

6-chloro-(1H,3H)-quinazolin-2,4-dione

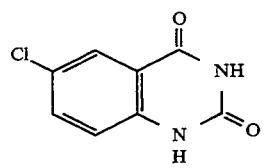

To a solution of 5-chloroanthranilamide (3.4 g)in tetrahydrofuran (50 mL) was added phosgene (16 mL, 1.93M solution in toluene) via an addition funnel. The reaction mixture was stirred at room temperature for 4 hours and then heated to reflux for another two hours. The reaction mixture was concentrated to a total volume about 10 mL. After cooling, the title compound (3.72 g) having the following physical data, was collected by filtration and dried in vacuum.

NMR (200 MHz, DMSO-d6): δ 7.19 (d, 1H), 7.69 (dd, 1H), 7.82 (d, 1H), 11.28 (broad, 1H), 11.45 (broad, 1H).

Reference example 12

4-chloro-2-chloromethylquinazoline

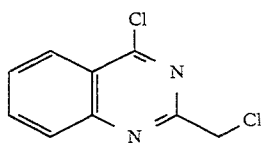

To a solution of anthranilonitrile (11.8 g) and chloroacetonitrile (7.5 g) in 1,4-dioxane (200 mL), cooled in an ice bath, was bubbled HCl gas. The reaction mixture was stirred for two and one-half hours at which time the reaction was allowed to warm to room temperature and continued to bubble HCl gas for 16 hours. After the HCl gas bubbling was ceased, nitrogen gas was bubbled through to remove any unreacted HCl gas. The mixture was concentrated at 45° C. in vacuo. The mixture was partitioned between methylene chloride (300 mL) and water (400 mL). The organic layer was separated, dried over anhydrous magnesium sulfate, and concentrated. The concentrate was dissolved in 200 mL of warm hexane, filtered and allowed to cool to room temperature. The title compound (9.1 g) was collected by filtration.

Reference example 13

2,4-dichloroquinazoline

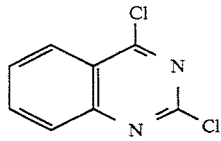

A mixture of benzoyleneurea (20.0 g), phosphorus oxychloride (100 mL) and N,N-dimethylaniline (12 mL) was refluxed for five hours. After stirring overnight at room temperature, the mixture was heated to reflux once more for an additional four hours. The cooled mixture was then poured into ice and the precipitate collected. The precipitate was purified on silica gel column with 5% methanol/chloroform as eluent. The isolated product was triturated in ether/hexane and collected to obtain the title compound (6.9 g).

The following compound was obtained by the same procedure as Reference example 13, by using 6-chloro-(1H,3H)-quinazolin-2,4-dione prepared by Reference example 11.

Reference example 13(a)

2,4,6-trichloroquinazoline

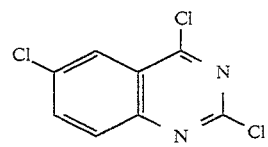

mp: 125° C. NMR (200 MHz, DMSO-d6): δ 8.09 (d, 1H), 8.21 (dd, 1H), 8.33 (d, 1H).

Reference example 14

4-phenylmethylamino-2-chloroquinazoline

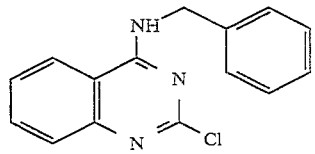

The title compound having the following physical data, was obtained by the same procedure as Example 1, by using the dichloroquinazoline prepared in Reference example 13 and phenylmethylamine (equivalent to dichloroquinazoline).

mp: 178°–180° C. NMR (CDCl3): δ 4.86 (d, 2H), 6.05 (s, 1H), 7.32–7.51 (m, 6H), 7.62–7.85 (m, 3H).

The following compounds were obtained by the same procedure as Reference example 14, by using the corresponding 4-chloro compounds prepared in Reference example 13(a) and 12, respectively.

Reference example 14(a)

4-phenylmethylamino-2,6-dichloroquinazoline

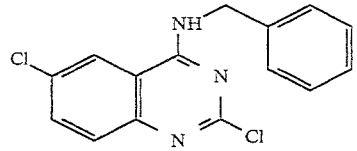

NMR (200 MHz, DMSO-d6): δ 4.74 (d, 2H), 7.28–7.43 (m, 5H), 7.67 (d, 1H), 7.85 (dd, 1H), 8.50 (d, 1H), 9.36 (broad, 1H).

Reference example 14(b)

4-phenylmethylamino-2-chloromethylquinazoline

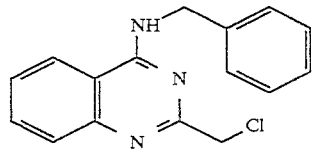

mp: 137°–139° C. NMR (CDCl3): δ 4.68 (s, 2H), 4.90 (d, 2H), 6.00 (bs, 1H), 7.27–7.90 (m, 9H).

EXAMPLE 5

4-phenylmethylamino-2-(1-imidazolyl)quinazoline

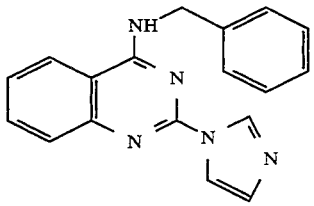

A mixture of the 2-chloro compound (0.81 g, prepared in Reference example 14), imidazole (0.81 g) and phenol (3.0 g) was heated to reflux for four and one-half hours. The mixture was then taken up in chloroform, washed twice with sodium hydroxide solution, dried over anhydrous potassium carbonate and concentrated. The concentrate was triturated in ether and collected to obtain the title compound (0.7 g) as a yellow solid having the following physical data.

mp: 21 2°–21 4° C. NMR (CDCl$_3$): ,5 4.86 (d, 2H), 6.05 (broad s, 1H), 7.32–7.51 (m, 6H), 7.62–7.85 (m, 3H).

The following compounds were obtained by the same procedure as Example 5, by using 4-phenylmethylamino-2-chloroquinazoline prepared in Reference example 14, 14(a) and 14(b) or corresponding quinazoline, and the proper heterocyclic compounds.

EXAMPLE 5(a)

4-phenylmethylamino-2-(2-methyl-1-imidazolyl)-quinazoline

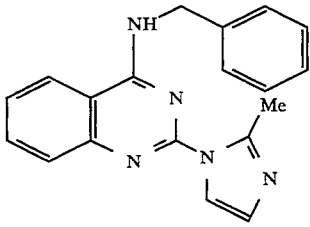

mp: 182°–186° C. NMR (CDCl$_3$): δ2.89 (s, 3H), 4.92 (d, 2H), 6.30 (broad, 1H), 6.97 (s, 1H), 7.30–7.50 (m, 5H), 7.73–7.82 (m, 3H), 7.96 (s, 1H). IR (KBr): ν 3240 (w), 3060 (w), 1618 (m), 1595 (s), 1559 (s), 1439 (m), 1403 (s), 1380 (s), 1305 (s), 766 (w), 696 (w)cm$^{-1}$.

EXAMPLE 5(b)

4-phenylmethylamino-2-(1,2,4-triazol-1-yl)quinazoline

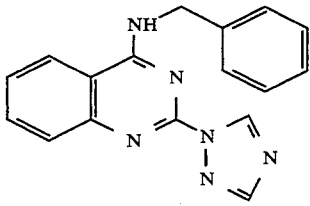

mp: 193°–195° C. NMR (CDCl$_3$): ,5 4.73 (d, 2H), 6.02 (bs, 1H), 7.17–7.74 (m, 8H), 7.59–7.65 (m, 3H). IR (KBr): ν 3240 (w), 3125 (w), 1618 (m), 1596 (s), 1580 (s), 1547 (s), 1491 (m), 1384 (s), 1314 (s), 1207 (s), 1052 (w), 763 (m), 698 (m)cm$^{-1}$.

EXAMPLE 5(c)

4-phenylmethylamino-6-chloro-2-(1-imidazolyl)-quinazoline

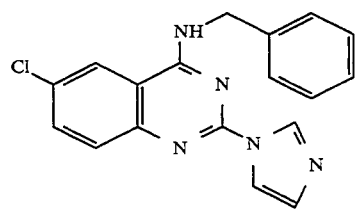

mp: 260°–264° C. (dec.). NMR (200 MHz, DMSO-d6): δ 4.84 (d, 2H), 7.09 (s, 1H), 7.28–7.50 (m, 5H), 7.70 (d, 1H), 7.82 (dd, 1H), 7.93 (s, 1H), 8.52 (d, 1H), 8.56 (s, 1H), 9.40 (broad. 1H).

EXAMPLE 5(d)

4-phenylmethylamino-2-((1-imidazolyl)methyl)-quinazoline

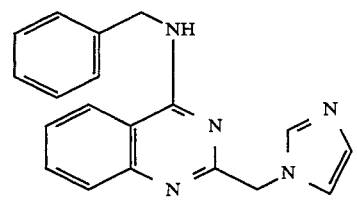

mp: 174°–176° C. NMR (200 MHz, DMSO-d6): ,5 4.70 (d, 2H), 5.18 (s, 2H), 6.88 (s, 1H), 7.16 (s, 1H), 7.17–7.40 (m, 4H), 7.50 (m, 1H), 7.60–7.82 (m, 3H), 8.28 (d, 1H), 8.92 (m, 1H).

EXAMPLE 5(e)

6-ethoxycarbonyl-4-phenylmethylamino-2-(1-imidazolyl)quinazoline

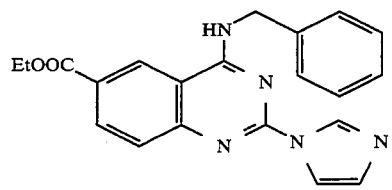

mp: 193° C. (dec.) NMR (200 MHz, CDCl$_3$) δ: 1.58 (t, 3H), 4.69–4.80(m, 4H), 6.62 (br, 1H), 7.17 (s, 1H), 7.35–7.44 (m, 5H), 7.89 (d, 1H), 7.98 (s, 1H), 8.24 (dd, 1H), 8.58 (d, 1H), 8.67 (s, 1H). IR (KBr)ν: 3275, 1652, 1626, 1588, 1472, 1438, 1314, 1093, 1055, 1014 cm$^{-1}$.

EXAMPLE 6

4-phenylmethylamino-2-(1-imidazolyl)quinazoline dihydrochloride

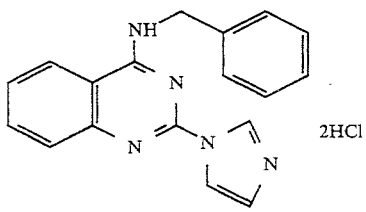

The title compound having the following physical data, was obtained by the same procedure as Example 2, by using the free base prepared in Example 5 and HCl/methanol solution.

mp: 248°–250° C. NMR (200 MHz, DMSO-d6): δ 4.96 (d, 2H), 7.20–7.40 (m, 3H), 7.50–7.54 (m, 2H), 7.63 (t, 1H), 7.75–7.81 (m, 1H), 7.88–7.90 (m, 2H), 8.43 (s, 1H), 8.55 (d, 1H), 9.85 (broad t, 1H), 10.03 (s, 1H). IR (KBr): ν 3055 (broad), 2655 (broad), 1634 (s), 1569 (s), 1520 (m), 1472 (m), 1395 (s), 760 (w) cm$^{-1}$.

By the same procedure as described in Reference example 13 and 14 and Example 5 and 6, the below compounds having the following physical data were given.

EXAMPLE 6(a)

4-phenylmethylamino-6-chloro-2-(1-imidazolyl)-quinazoline dihydrochloride

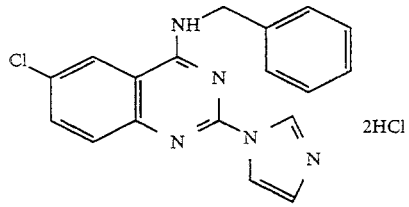

mp: 1 86° C. (dec.). NMR (200 MHz, DMSO-d6): δ 4.95 (m, 2H), 7.25–7.40 (m, 3H), 7.49–7.53 (m, 2H), 7.78 (d, 1H), 7.90 (t, 1H), 7.92 (dd, 1H), 8.43 (t, 1H), 8.71 (d, 1H), 9.88 (broad, 1H), 10.03 (t, 1H).

EXAMPLE 6(b)

4-phenylmethylamino-2-((1-imidazolyl)methyl)-quinazoline dihydrochloride

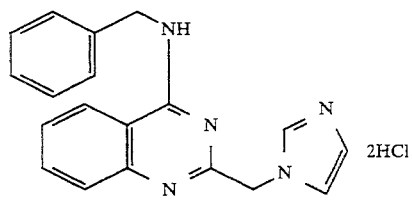

mp: 306° C.(dec.). NMR (200 MHz, DMSO-d6): δ 4.64 (m, 2H), 5.81 (s, 2H), 7.17–7.40 (m, 5H), 7.68–8.10 (m, 5H), 8.68 (m, 1H), 9.26 (s, 1H).

The following compound was obtained by the same procedure as described in Reference example 13, 14 and example 5 and 6, by using the corresponding (1H,3H)-quinazoline-2,4-dione or its derivative and corresponding amine.

EXAMPLE 6(c)

6-bromo-4-phenylmethylamino-2-(1-imidazolyl)-quinazoline dihydrochloride

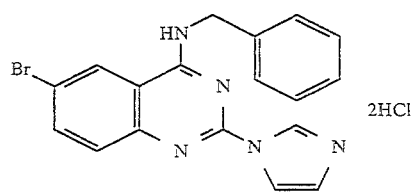

mp:199°–202° C., (dec.) NMR (200 MHz, DMSO-d6) δ: 4.95 (m, 2H), 7.25–7.40 (m, 3H), 7.49–7.53 (m, 2H), 7.70 (d, 1H), 7.81 (t, 1H), 8.01 (dt, 1H), 8.38 (d, 1H), 8.81 (d, 1H), 9.80 (broad, 1H), 9.88 (d, 1H).

EXAMPLE 6(d)

7-chloro-4-phenylmethylamino-2-(1-imidazolyl)-quinazoline

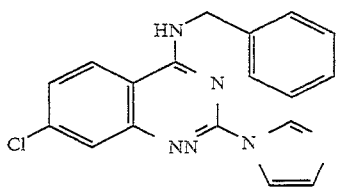

mp: 265°–268° C. NMR (200 MHz, DMSO-d6):δ 4.85 (s, 2H), 7.08 (s, 1H), 7.21–7.40 (m, 3H), 7.42–7.58 (m, 2H), 7.71 (s, 1H), 7.91 (s, 1H), 8.35 (d, 1H), 8.54 (s, 1H). IR (KBr): ν 3260 (w), 3135 (w), 1609 (s), 1570 (s), 1473 (s), 1451 (s), 1418 (s), 1349 (m), 1307 (m), 1037 (m), 778 (w), 698 (w) cm$^{-1}$.

EXAMPLE 6(e)

6-chloro-4-phenylmethylamino-2-(1-imidazolylmethyl)-quinazoline dihydrochloride

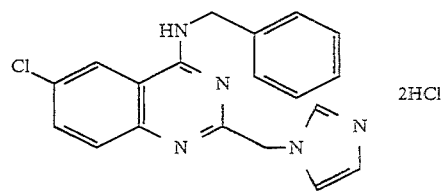

mp: 290° C., (dec.) NMR (200 MHz, DMSO-d6):δ 4.66 (d, 2H), 5.72 (s, 2H), 7.18–7.42 (m, 5H), 7.72–8.05 (m, 4H), 8.76 (s, 1H), 9.27 (s, 1H).

EXAMPLE 6(f)

6-nitro-4-phenylmethylamino-2-(1-imidazolyl)quinazoline hydrochloride

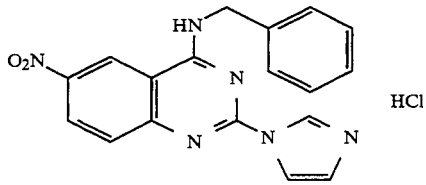

mp: 190° C., (dec.) NMR (200 MHz, DMSO-d6) δ: 5.00 (m, 2H), 7.25–7.42 (m, 3H), 7.45–7.53 (m, 2H), 7.76 (broad, 1H), 7.87–7.93 (d, 1H), 8.39 (broad, 1H), 8.57–8.65 (d, 1H) 9.56 (s, 1H), 9.82 (broad, 1H), 10.28 (broad, 1H). IR (KBr)ν: 1335(s), 1403(s), 1438(w), 1518(w), 1601(s), 3405(broad), 3445(w) cm$^{-1}$.

EXAMPLE 6(g)

6-methoxy-4-phenylmethylamino-2-(1-imidazolyl)-quinazoline dihydrochloride

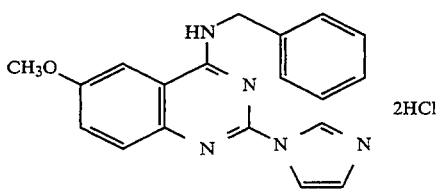

mp: 196° C., (dec.) NMR (200 MHz, DMSO-d6) δ:3.93 (s,3H), 4.98 (m, 2H), 7.25–7.42 (m, 3H), 7.45–7.57 (m, 2H), 7.74 (d, 1H), 7.87 (d, 1H), 7.95 (d, 1H), 8.41 (d, 1H), 9.55 (broad, 1H), 9.96 (d, 1 H). IR (KBr)ν: 1254(m), 1395(s), 1506(m), 1558(s), 1601(s), 3065(w), 3245(w), and 3395(w) cm$^{-1}$.

EXAMPLE 6(h)

6-chloro-4-phenylamino-2-(1-imidazolylmethyl)-quinazoline dihydrochloride

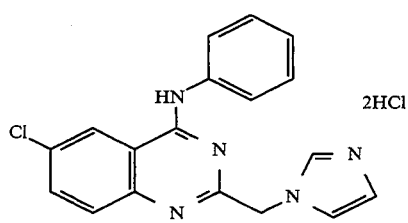

mp: 280° C., (dec.) NMR (200 MHz, DMSO-d6) 67 : 5.72 (s, 2H), 7.12–8.03 (m, 9H), 8.99 (m, 1H), 9.26 (s, 1H), 10.65 (bs, 1H). IR (KBr) ν: 3100 (m), 2830 (m), 2565 (m), 1635 (m), 1608 (m), 1578 (sd), 1492 (ms), 1151 (m) cm$^{-1}$.

EXAMPLE 6(i)

6-chloro-4-(3-carboxyphenyl)amino-2-(1-imidazolylmethyl)quinazoline dihydrochloride

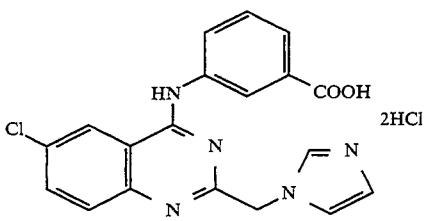

mp: 285 PC, (dec.) NMR (200 MHz, DMSO-d6) δ: 5.69 (s, 2H), 7.49 (t, 1H), 7.70–8.02 (m, 6H), 8.26 (m, 1H), 8.90 (m, 1H), 9.26 (s, 1H), 10.50 (bs, 1H). IR (KBr)ν: 3326 (m), 3065 (m), 2835 (m), 1698 (m), 1631 (m), 1602 (m), 1561 (s), 1486 (m), 1444 (m), 1400 (m), 1376 (mw) cm$^{-1}$.

EXAMPLE 6(j)

6-dimethylaminosulfonyl-4-phenylmethylamino-2-(1-imidazolyl)quinazoline hydrochloride

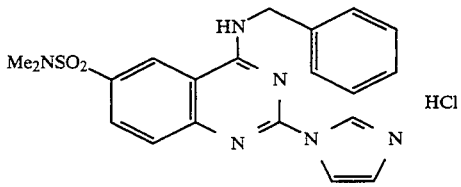

mp: 264°–266° C. NMR (200 MHz, DMSO-d6) δ: 2.69(s, 6H), 5.00(d, 2H), 7.25–7.45(m, 3H), 7.46–7.54(m, 2H), 7.78(m, 1H), 7.93(dd, 1H), 8.13(d, 1H), 8.40(m, 1H), 8.95(m, 1H), 9.84(m, 1H), 10.13(br, 1H). IR (KBr):δ 3400(m), 3320(m), 2960(w), 1597(s), 1556(m), 1520(m), 1445(m), 1398(s), 1341(s), 1164(s), 728(s), 579(s)cm$^{-1}$.

EXAMPLE 6(k)

4-(2-furylmethyl)amino-2-(1-imidazolyl)quinazoline dihydrochloride

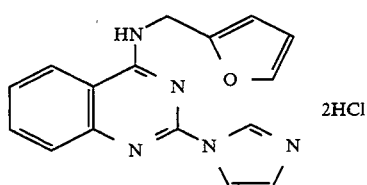

mp: 230° C., (dec.) NMR (200 MHz, DMSO-d6)δ:4.99 (d, 2H), 6.48 (m, 2H), 7.57–7.97 (m, 5H), 8.49 (m, 2H), 9.64 (t, 1H), 10.08 (s, 1H).

EXAMPLE 6(I)

4-(2-thienylmethyl)amino-2-(1-imidazolyl)quinazoline

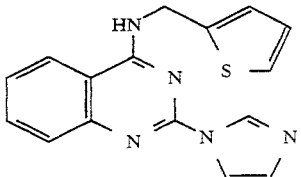

mp: 234°–235° C. NMR (200 MHz, DMSO-d6): δ 5.03 (d, 2H), 7.00 (m, 1H), 7.13 (s, 1H), 7.18 (d, 1H), 7.37 (d, 1H), 7.52 (t, 1H), 7.78 (m, 2H), 8.02 (s, 1H), 8.28 (d, 1H), 8.67 (s, 1H), 9.40 (t, 1H). IR (KBr): ν 3255 (w, broad), 1617 (w), 1668 (s), 1470 (s), 1402 (s), 1321 (m) cm$^{-1}$.

EXAMPLE 6(m)

4-(2-tetrahydrofuranylmethyl)amino-2-(1-imidazolyl)-quinazoline

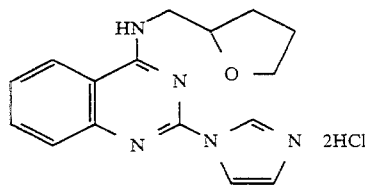

mp: 98°–150° C. NMR (200 MHz, DMSO-d6)δ:1.62–2.13 (m, 4H), 3.62–3.90 (m, 4H), 4,12–4.31 (m, 2H), 7.54–7.97 (m, 4H), 8.44 (s, 1H), 9.32 (t, 1H), 10.02 (s, 1H). IR (KBr) ν: 3500–2700 (s, broad), 1635 (m), 1576 (m), 1396 (m), 1063 (w), 765 (w) cm$^{-1}$.

EXAMPLE 6(n)

4-(2-methoxyethyl)amino-2-(1-imidazolyl)quinazoline dihydrochloride

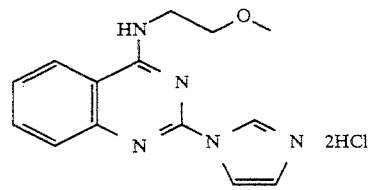

mp: 210°–215° C. NMR (200 MHz, DMSO-d6) δ: 3.31 (s, 3H), 3.66 (t, 2H), 3.85 (q, 2H), 7.61 (t, 1H), 7.78 (d, 1H), 7.85 (m, 1H), 8.42 (m, 2H), 9.23 (t, 1H), 9.95 (s, 1H).

EXAMPLE 6(o)

4-phenylmethylamino-2-(1-imidazolyl)-5,6,7,8-tetrahydro-quinazoline dihydrochloride

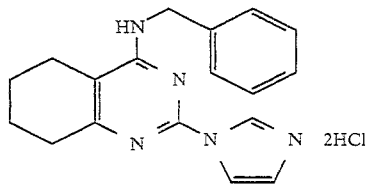

mp: 195° C., (dec.) NMR (200 MHz, DMSO-d6)δ:1.79 (m, 4H), 2.45 (m, 2H), 2.66 (m, 2H), 4.74 (d, 2H), 7.17–7.48 (m, 5H), 7.83 (cs, 1H), 8.13 (t, 1H), 8.24 (cs, 1H), 9.84 (cs, 1H).

EXAMPLE 6(p)

6-dimethylaminomethylideneaminosulfonyl-4-phenylmethylamino-2-(1-imidazolyl)quinazoline dihydrochloride

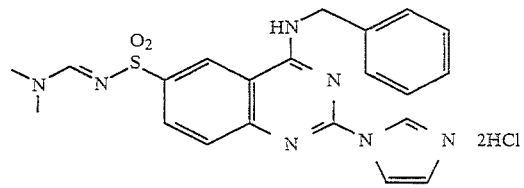

mp: 225° C. NMR (200 MHz, DMSO-d6) δ: 2.93 (s, 3H), 3.18 (s, 3H), 4.97 (d, 2H), 7.25–7.40 (m, 3H), 7.49–7.53 (m, 2H), 7.79 (s, 1H), 7.84 (d, 1H), 8.15 (dt, 1H), 8.30 (s, 1H), 8.39 (s, 1H), 9.00 (s, 1H), 9.86 (s, 1H), 10.10 (t, 1H).

EXAMPLE 6(q)

6-(phenylmethylaminosulfonyl)-4-phenylmethylamino-2-(1-imidazolyl)quinazoline

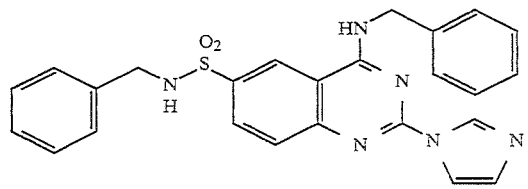

mp: 207°–8° C. NMR (200 MHz, DMSO-d6) δ: 4.09 (d, 2H), 4.89 (m, 2H), 7.11 (s, 1H), 7.16–7.52 (m, 10H), 7.79 (d, 1H), 7.96 (d, 1H), 8.07 (dd, 1H), 8.28 (t, 1H), 8.60 (s, 1H), 8.83 (m, 1H), 9.80 (broad t, 1H).

EXAMPLE 6(r)

4-(2-phenylethyl)amino-2-(1-imidazolyl)quinazoline dihydrochloride

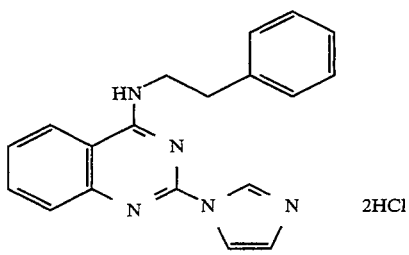

mp: 70°–100° C. NMR (200 MHz, DMSO-d6) δ: 3.05 (t, 2H), 3.95 (q, 2H), 7.12–7.38 (m, 6H), 7.57 (t, 1H), 7.73 (m, 2H), 7.89 (m, 3H), 8.41 (m, 2H), 9.38 (t, 1H), 9.96 (s, 1H).

EXAMPLE 6(s)

4-cyclohexylmethylamino-2-(1-imidazolyl)quinazoline dihydrochloride

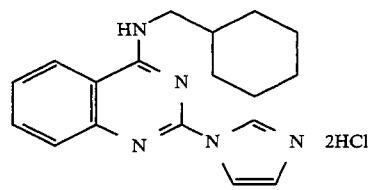

mp: 140°–150° C. NMR (200 MHz, DMSO-d6)δ:0.98–1.32 (m, 5H), 1.53–1.90 (m, 6H), 3.58 (t, 2H), 7.59 (t, 1H), 7.77 (m, 1H), 7.89 (t, 2H), 8.41 (s, 1H), 8.56 (d, 1H), 9.28 (t, 1H), 9.97 (s, 1H).

EXAMPLE 6(t)

6-carboxy-4-phenylmethylamino-2-(1-imidazolyl)-5,6,7,8-tetrahydroquinazoline dihydrochloride

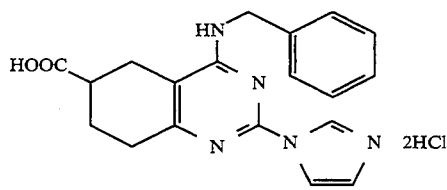

mp: 105° C. (dec.) NMR (200 MHz, DMSO-d6) δ:1.82 (m, 1H), 2.10 (m, 1H), 2.71 (m, 5H), 4.74 (d, 2H), 7.18–7.47 (m, 5H), 7.82 (s, 1H), 8.24 (s, 1H), 8.25 (m, 1H), 9.84 (s, 1H). IR (KBr)ν: 3140 (bin), 2935 (bin), 1718 (mw), 1654 (m), 1617 (ms), 1522 (mw), 1394 (m) cm⁻¹.

EXAMPLE 6(u)

6-phenylmethylaminocarbonyl-4-phenylmethylamino-2-(1-imidazolyl)quinazoline dihydrochloride

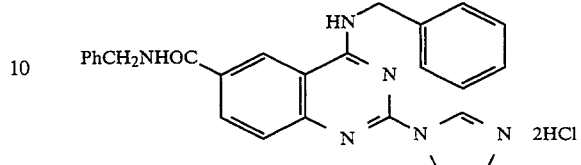

mp: 235°–237° C. NMR (200 MHz, DMSO-d6) δ: 4.54 (d, 2H), 7.20–7.40 (m, 8H), 7.48–7.52 (m, 2H), 7.70 (s, 1H), 7.81 (d, 1H), 8.31 (dd, 1H), 8.37 (s, 1H), 9.09 (s, 1H), 9.22 (br, 1H), 9.82 (s, 1H), 9.89 (br, 1H). IR (KBr) ν: 3500–3000 (br), 1647, 1604, 1555, 1453, 1398, 1 31 5, 699 cm⁻¹.

EXAMPLE 6(v)

4-(4-tetrahdyropyranylmethyl)amino-2-(1-imidazolyl)-quinazoline dihydrochloride

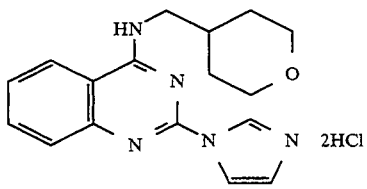

mp: 160°–195° C. NMR (200 MHz, DMSO-d6) δ: 10.0 (m, 1H), 9.29 (m, 1H), 8.53 (d, 1H), 8.45 (m, 1H), 7.82–7.95 (d, 2H), 7.75 (d, 1H), 7.60 (t, 1H), 3.86 (m, 2H), 3.64 (m, 2H) 3.28 (t, 2H), 2.02 (m, 1H), 1.60–1.75 (m, 2H), 1.21–1.48 (m, 2H). IR (KBr)ν: 1635, 1604, 1562, 1524, 1471, 1443, 1393, 1091, 762 cm⁻¹.

EXAMPLE 6(w)

6-methoxy-4-(4-tetrahydropyranylmethyl)amino-2-(1-imidazolyl)quinazoline dihydrochloride

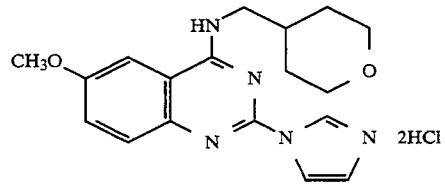

mp: 170°–190° C. NMR (200 MHz, DMSO-d6) δ: 9.96 (s, 1H), 9.15 (m, 1H), 9.42 (s, 1H), 7.98 (s, 1H), 7.89 (s, 1H), 7.71 (d, 1H), 7.52 (dd, 1H), 3.94 (s, 3H), 3.80–3.95 (m, 2H), 3.62 (m, 2H), 3.29 (t, 2H), 2.02 (m, 1H), 1.60–1.75 (m, 2H), 1.20–1.49 (m, 2H). IR (KBr)ν: 1637, 1605, 1569, 1524, 1473, 1440, 1391, 1251, 1091, 1020 cm⁻¹.

EXAMPLE 6(x)

6-chloro-4-(4-tetrahydropyranylmethyl)amino-2-(1-imidazolyl)quinazoline dihydrochloride

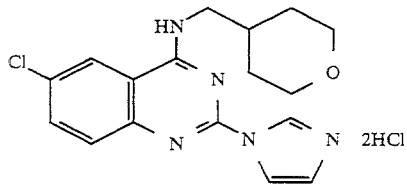

mp: 155°–185° C. NMR (200 MHz, DMSO-d6) 8:9.89 (s, 1H), 9.25 (m, 1H), 8.66 (m, 1H), 8.41 (m, 1H), 7.72–7.96 (m, 3H), 3.81–3.95 (m, 2H), 3.56–3.70 (m, 2H), 3.28 (t, 2H), 2.02 (m, 1H), 1.63–1.79 (m, 2H), 1.20–1.46 (m, 2H). IR (KBr)ν: 1604, 1577, 1524, 1497, 1446, 1396, 1349, 1089 cm$^{-1}$.

EXAMPLE 6(y)

6-iodo-4-phenylmethylamino-2-(1-imidazolyl)quinazoline dihydrochloride

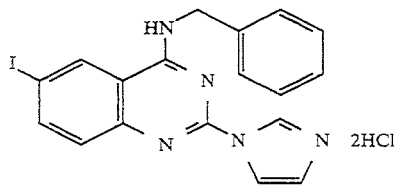

mp: 183° C., (dec.) NMR (200 MHz, DMSO-d6) δ: 4.95 (m, 2H), 7.25–7.40 (m, 3H), 7.45–7.60 (m, 3H), 7.88 (t, 1H), 8.16 (dt, 1H), 8.43 (t, 1H), 8.93 (s, 1H), 9.78 (t, 1H), 10.01 (d, 1H). IR (KBr) ν: 3060, 2685, 1634, 1600, 1541, 1406, 1390 cm$^{-1}$.

EXAMPLE 6(z)

4-(4-trifuloromethoxyphenylmethyl)amino-2-(1-imidazolyl)quinazoline dihydrochloride

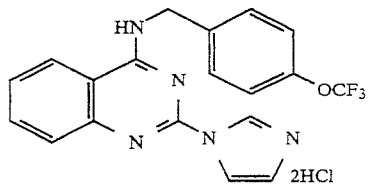

mp: 140°–145° C. NMR (200 MHz, DMSO-d6) δ: 5.01 (m, 2H), 7.30–7.40 (m, 2H), 7.60–7.88 (m, 6H), 8.42–8.55 (m, 2H), 9.78 (bm, 1H), 10.35 (s, 1H). IR (KBr)ν: 3070, 1634, 1604, 1560, 1525, 1394, 1263, 1224, 1164 cm$^{-1}$.

EXAMPLE 6(aa)

4-(3-trifluoromethoxyphenylmethyl)amino-2-(1-imidazolyl)quinazoline dihydrochloride

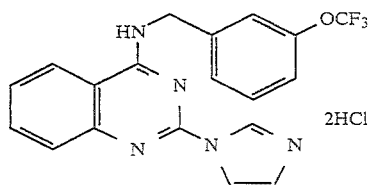

(2HCl salt)

mp: 170°–180° C. NMR (200 MHz, DMSO-d6): 85.01(d, 2H), 7.25(d, 1H), 7.42–7.71(m, 3H), 7.81 (s, 1H), 7.88(m, 2H), 8.44(s, 1H), 8.54(d, 1H), 9.95(t, 1H), 10.06(s, 1H). IR(KBr): ν 3430(w), 3020(w), 2960(w), 1653(s), 1603(s), 1542(m), 1396(s), 1270(s), 1216(m) cm$^{-1}$.

EXAMPLE 6(bb)

6-methoxy-4-(2-(2-hydroxyethoxy)ethyl)amino-2-(1-imidazolyl)quinazoline dihydrochloride

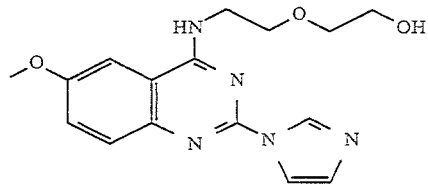

(2HCl salt)

mp:167.5°–170° C. NMR (200 MHz, DMSO-d6): δ 3.51 (s, 4H), 3.75–3.78(m, 2H), 3.85–3.90(m, 2H), 3.93(s, 3H), 7.49(dd, 1H), 7.70(d, 1H), 7.84(t, 1H), 7.98(m, 1H), 8.39(m, 1H), 9.19(br, 1H), 9.90(t, 1H). IR(KBr): ν 3270(s), 2940(m), 1610(s), 1557(m), 1513(s), 1396(s), 1247(m), 1115(m), 1029(w) cm$^{-1}$.

EXAMPLE 6(cc)

4-(2-methoxyethyl)amino-2-(1-imidazolyl)-5,6,7,8-tetrahydroquinazoline dihydrochloride

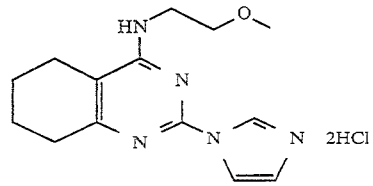

(2HCl salt)

mp: 140°–142.5° C. NMR (200 MHz, DMSO-d6): δ 1.77(s, 4H), 2.38(s, 2H), 2.65(s, 2H), 3.28(s, 3H), 3.54(t, 3H), 3.57(d, 2H), 7.49(br, 1H), 7.84(s, 1H), 8.30(s, 1H), 9.86(s, 1H). IR(KBr): ν 3230–2355(br, m), 1555(s), 1506(s), 1526(s), 1449(w), 1395(s), 1101(m), 828(w), 756(m)cm$^{-1}$.

EXAMPLE 6(dd)

4-(2-methoxyethyl)amino-6-iodo-2-(1-imidazolyl)-
quinazoline dihydrochloride

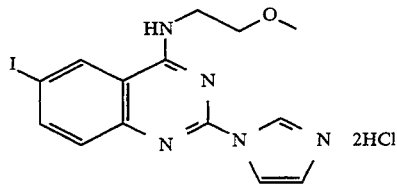

(2HCl salt)

mp: 159°–161° C. NMR (200 MHz, DMSO-d6): δ 3.31 (s, 3H), 3.67(t, 2H), 3.88(t, 2H), 7.54(d, 1H), 7.85(t, 1H), 8.13(dd, 1H), 8.42(t, 1H), 8.89(d, 1H), 9.20(t, 1H), 9.94(t, 1H). IR(KBr): ν 3205–2365(m, br), 1633(s), 1604(s), 1 564(s), 1541 (s), 1506(s), 1459(m), 1409(s), 1367(s), 1193(w), 1114(m), 1011(m), 859(w), 833(m), 777(m), 713(w), 621(w), 526(w)cm$^{-1}$.

EXAMPLE 6(ee)

4-phenylmethylamino-6,8-diiodo-2-(1-imidazolyl)-
quinazoline dihydrochloride

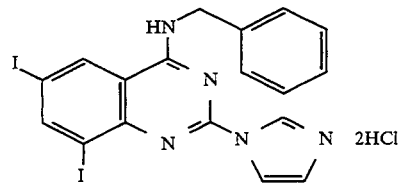

(2HCl salt)

mp:303°–304° C. (dec.) NMR (200 MHz, DMSO-d6): δ 4.94(d, 2H), 7.33(dd, 3H), 7.49(dd, 2H), 7.74(t, 1H), 8.24(t, 1H), 8.67(t, 1H), 8.88(d, 1H), 9.66(s, 1H), 9.77(br, 1 H) . IR(KBr): ν 3410–2365(br, m), 1599(s), 1437(m), 1387(s), 1350(m), 1314(m), 1273(w), 1061(w), 1020(w), 793(w), 748(w), 701(w), 620(w)cm$^{-1}$.

EXAMPLE 6(ff)

4-(2-methaxyethyl)amino-6-methoxy-2-(2-methyl-1-
imidazolyl)quinazoline dihydrochloride

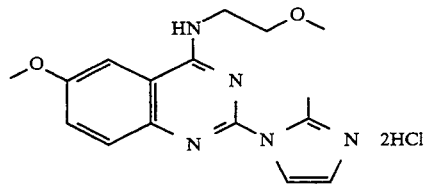

(2HCl salt)

mp: 263°–264° C. NMR (200 MHz, DMSO-d6): δ 3.04(s, 3H), 3.31(s, 3H), 3.68(m, 2H), 3.84(m, 2H), 3.92(s, 3H), 7.50(dd, 2H), 7.72(m, 2H), 7.91(s, 1H), 8.30(s, 1H), 9.10(m, 1H). IR(KBr): ν 3230(w), 2680(w), 1615(s), 1592(s), 1560(s), 1420(s), 1382(m), 1248(m), 909(w) cm$^{-1}$.

EXAMPLE 6(gg)

4-(2-hydroxyethyl)amino-6-methoxy-2-(1-imidazolyl)quinazoline dihydrochloride

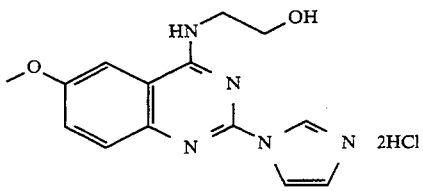

(2HCl salt)

mp: 228°–233° C. NMR (200 MHz, D20): δ 3.63(t, 2H), 3.74(s, 3H), 3.83(t, 2H), 6.90(d, 1H), 7.16(dd, 1H), 7.26(d, 1H), 7.57(d, 1H), 7.96(d, 1H), 9.23(s, 1H). IR(KBr): ν 2700–3400(br), 1605(s), 1569(m), 1520(m), 1394(m), 1246(w), 1040(w), 81 5(w) cm$^{-1}$.

EXAMPLE 6(hh)

4-(2-methoxyethyl)amino-6,8-diiodo-2-(1-imidazolyl)-
quinazoline dihydrochloride

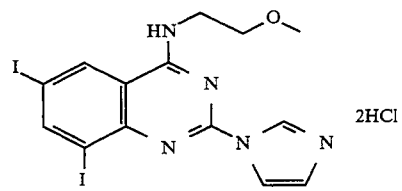

(2HCl salt)

mp: 244°–246.5° C. NMR (200 MHz, DMSO-d6): δ 3.31(3H), 3.65(2H), 3.89(2H), 7.79(s, 1H), 8.29(s, 1H), 8.68(s, 1H), 8.89(s, 1H), 9.32(br, 1H). IR(KBr): ν 3240–2335(br, m), 1598(s), 1553(w), 1523(w), 1476(m), 1436(m), 1383(m), 1354(m), 1275(w), 1107(w), 1086(m), 1018(m), 991(w), 860(w), 793 (m), 752(w), 724(w), 615(w)cm$^{-1}$.

EXAMPLE 6(ii)

4-(2-(2-hydroxyethoxy)ethyl)amino-2-(1-imidazolyl)-
5,6,7,8-tetrahydroquinazoline dihydrochloride

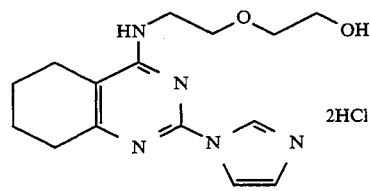

(2HCl salt)

mp: 125°–128° C. NMR (200 MHz, DMSO-d6): δ 1.80(4H), 2.40(2H), 3.65(br, 8H), 7.45(br, 1H), 7.85(d, 1H), 8.30(d, 1H), 9.85(d, 1H). IR(KBr): ν 3380(s), 3120(s), 2945(m), 2755–2460(m), 1615(s), 1540(s), 1457(m), 1428(m), 1390(s), 1350(m), 1319(w), 1103(m), 1070(m), 829(w), 624 (w) cm$^{-1}$.

EXAMPLE 6(jj)

4-(2-phenoxyethyl)amino-6-methoxy-2-(1-imidazolyl)-quinazoline and its dihydrochloride

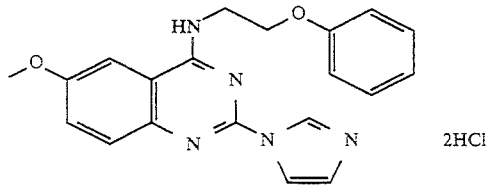

(free base)

mp: 213°–21 4° C. NMR (200 MHz, DMSO-d6): δ 3.89 (s, 3H), 4.04(d, 2H), 4.31(t, 2H), 6.93–7.01 (3H), 7.08(d, 1H), 7.28(td, 2H), 7.45(dd, 1H), 7.64(d, 1H), 7.78(d, 1H), 7.93(t, 1H), 8.57(s, 1H), 9.85(br, 1H). IR(KBr): ν 1599(s), 1555(s), 1491(s), 1409(s), 1382(w), 1310(m), 1242(s), 1051 (s), 752(w) cm$^{-1}$.

(2HCl salt)

mp: 184°–186° C. NMR (200 MHz, DMSO-d6): δ 3.94(s, 3H), 4.12(d, 2H), 4.33(t, 2H), 6.90–7.01 (3H), 7.29(t, 2H), 7.53(dd, 1H), 7.88(t, 1H), 7.96(d, 1H), 8.40(t, 1H), 9.31 (br, 1H), 9.93(d, 1H). IR(KBr): ν 3050(m), 2840–2335(m), 1637(s), 1598(s), 1497(m), 1472(m), 1380(s), 1258(s), 1122(w), 1077(w), 1029(m), 775(m), 747(m)cm$^{-1}$.

EXAMPLE 6(kk)

4-(2-(2-hydroxyethoxy)ethyl)amino-6-iodo-2-(1-imidazolyl)quinazoline and its dihydrochloride

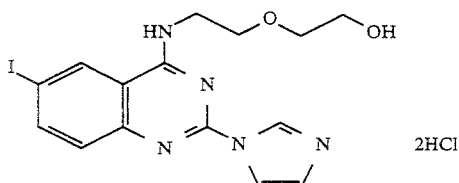

(free base)

NMR (200 MHz, DMSO-d6): δ 3.50(s, 4H), 3.75(dd, 2H), 3.78(d, 2H), 4.59(br, 1H), 7.10(d, 1H), 7.47(dd, 1H), 7.95(d, 1H), 8.05(d, 1H), 8.52(d, 1H), 8.7 (s, 1H), 8.57(br, 1H).

(2HCl salt)

mp: 132°–135° C. NMR (200 MHz, DMSO-d6): δ 3.50(s, 4H), 3.75(d, 2H), 3.86(d, 2H), 7.53(d, 1H), 7.83(s, 1H), 8.15(dd, 1H), 8.40(s, 1H), 8.89(d, 1H), 9.22(br, 1H), 9.90(s, IR(KBr): ν 3230–2720(br, m), 1607(s), 1555(m), 1526(m), 1492(m), 1445(m), 1394(s), 1348(m), 1118(m), 1063(m), 1027(m), 859(m), 622 cm$^{-1}$.

EXAMPLE 6(ll)

4-(2-methoxyethyl)amino-6-methylthio-2-(1-imidazolyl)quinazoline and its dihydrochloride

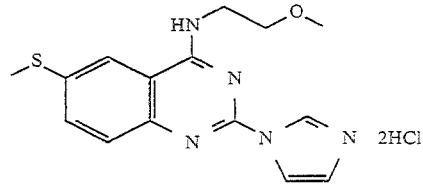

(free base)

mp: 201°–202° C. NMR (200 MHz, DMSO-d6): δ 2.61(s, 3H), 3.32(s, 3H), 3.65(m, 2H), 3.81(m, 2H), 7.10(s, 1H), 7.58–7.73(m, 2H), 7.95(s, 1H), 8.10(s, 1H), 8.59(s, 1H), 8.83 (t, 1H).

(2HCl salt)

mp: 230°–232° C. NMR (200 MHz, DMSO-d6): δ 2.65(s, 3H), 3.31(s, 3H), 3.66(m, 2H), 3.88(m, 2H), 7.64–7.83(m, 2H), 7.89(s, 1H), 8.24(m, 1H), 8.42(s, 1H), 9.28(t, 1H), 9.98(s, 1H).

EXAMPLE 6(mm)

4-(2-(2-hydroxyethoxy)ethyl)amino-6-methylthio-2-(1-imidazolyl)quinazoline

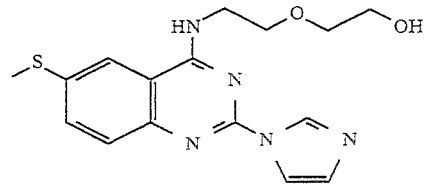

(free base)

mp: 169°–172° C.

NMR (200 MHz, DMSO-d6): δ 2.61(s, 3H), 3.51(s, 4H), 3.76(m, 4H), 4.60(m, 1H), 7.10(s, 1H), 7.57–7.76(m, 2H), 7.95(s, 1H), 8.09(s, 1H), 8.59(s, 1H), 8.82(m, 1H).

EXAMPLE 6(nn)

4-(2-(2-hydroxyethoxy)ethyl)amino-6-methylthio-2-(1-imidazolyl)quinazoline dihydrochloride

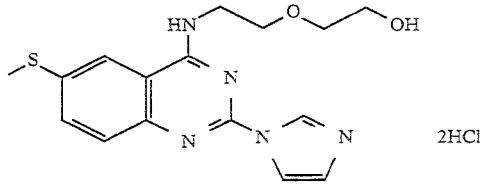

(2HCl salt)

mp: 180°–182° C. NMR (200 MHz, DMSO-d6): δ 2.65(s, 3H), 3.51(s, 4H), 3.75(m, 2H), 3.90(m, 2H), 7.64–7.82(m, 2H), 7.87(m, 1H), a.26(m, 1H), 8.42(1H), 9.34(t, 1H), 9.98 (m, 1H).

EXAMPLE 6(oo)

6-methylthio-4-phenylmethylamino-2-(1-imidazolyl)-quinazoline dihydrochloride

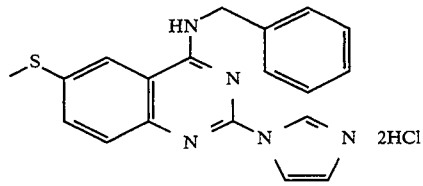

mp: 192°–195° C. NMR (200 MHz, DMSO-d6): δ 2.64(s, 3H), 4.96(d, 2H), 7.31–7.86(m, 9H), 8.26(s, 1H), 8.40(s, 1H), 9.75(t, 1H), 9.96(s, 1H). IR (KBr): ν 3210(w), 3040(m), 2600(m), 1630(s), 1556(s), 1495(m), 1433(m), 1510(s), 1339(m), 1203(w), 1112(w), 1091(w), 1013(w), 823(w), 743(m), 704(m), 615(w)cm$^{-1}$.

EXAMPLE 6(pp)

4-(3-methoxypropyl)amino-6-methoxy-2-(1-imidazolyl)quinazoline dihydrochloride

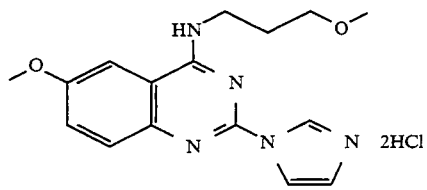

mp: 191°–194° C. NMR (200 MHz, DMSO-d6): δ 1.94(m, 2H), 3.25(s, 3H), 3.42(t, 2H), 3.69(m, 2H), 3.90(s, 3H), 7.45(m, 1H), 7.64(d, 1H), 7.86(m, 1H), 7.99(m, 1H), 8.35(m, 1H), 9.30(m, 1H), 9.88(m, 1H). IR (KBr): ν 1641, 1603, 1587, 1573, 1529, 1421, 1382, 1253, 1111, 1027, 858 cm$^{-1}$.

EXAMPLE 6(qq)

4-(2-methoxyethyl)amino-6-methoxycarbonyl-2-(1-imidazolyl)quinazoline

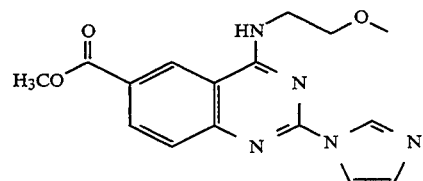

mp: 252°–253° C. NMR (200 MHz, DMSO-d6): δ 3.32(s, 3H), 3.66(t, 2H), 3.83(t, 2H), 3.92(s, 3H), 7.13(s, 1H), 7.75(d, 1H), 7.98(s, 1H), 8.23(s, 1H), 8.63(s, 1H), 9.02(s, 1H), 9.28. IR (KBr):δ 3245(w), 3140(w), 2900(w), 1724(s), 1601(s), 1473(s), 1437(s), 1407(s), 1310(s), 1119(m), 1021(m), 766cm$^{-1}$.

EXAMPLE 6(rr)

4-[2-(2-hydroxyethoxy)ethyl]amino-6-methoxycarbonyl-2-(1-imidazolyl)quinazoline

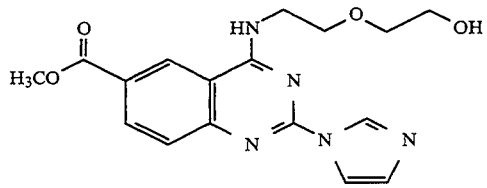

mp: 233°–235° C. NMR (200 MHz, DMSO-d6): δ 3.50(m, 4H), 3.70–3.90(m, 4H), 3.93(s, 3H), 4.60(m, 1H), 7.12(s, 1H), 7.75(d, 1H), 7.99(s, 1H), 8.25(dd, 1H), 8.63(s, 1H), 9.03(m, 1H), 9.28( m, 1H). IR (KBr):δ 3245(mw), 2950(w), 1730(ms), 1626(w), 1603(s), 1558(m), 1474(m), 1437(m), 1406(m), 1309(m), 1281(w), 1229(w), 1125(w), 1102(w), 1051 (w) cm$^{-1}$.

EXAMPLE 6(ss)

4-(2-methylthioethyl)amino-6-methoxy-2-(1-imidazolyl)quinazoline

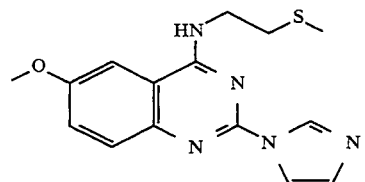

mp: 168°–178° C. NMR (200 MHz, DMSO-d6): δ 2.17(s, 3H), 2.89(t, 2H), 3.90(m, 2H), 3.93(s, 3H), 7.55(dd, 1H), 7.69(d, 1H), 7.87(s, 1H), 7.97(s, 1H), 8.40(s, 1H), 9.34(t, 1H), 9.93(s, 1H). IR (KBr) :ν 3410, 3095, 2675, 1635, 1609, 1587, 1400, 1264, 1018 cm$^{-1}$

EXAMPLE 6(tt)

4-(2-methylsulfinylethyl)amino-6-methoxy-2-(1-imidazolyl)quinazoline

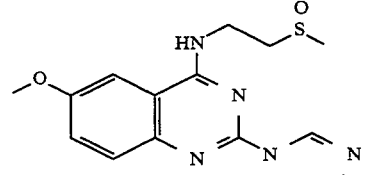

mp: 238°–242° C. NMR (200 MHz, DMSO-d6): δ 2.63(s, 3H), 3.10–3.70(m, 4H), 3.92(s, 3H), 7.53(dd, 1H), 7.72(d, 1H), 7.88(d, 2H), 8.48(s, 1H), 9.43(m, 1H), 10.01 (s, 1H). IR (KBr):n 3435, 3005, 2710, 1625, 1560, 1398, 1248, 1020, 825 cm$^{-1}$.

EXAMPLE 6(uu)

4-(2-methylsulfonylethyl)amino-6-methoxy-2-(1-imidazolyl)quinazoline

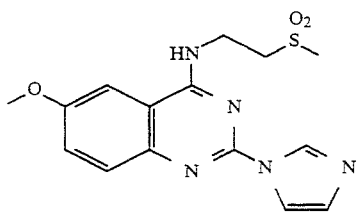

mp: 245°–252° C. NMR (200 MHz, DMSO-d6): δ 3.09(s, 3H), 3.61 (t, 2H), 3.92(s, 3H), 4.09(m, 2H), 7.54(dd, 1H), 7.76(d, 1H), 7.88(s, 2H), 8.45(s, 1H), 9.38(br, 1H), 9.89(s, 1H).

Reference example 15

2-(2-(3-pyridyl)vinyl)quinazolin-4-one

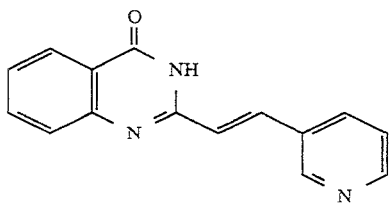

A mixture of 2-methylquinazolin-4-one (6.1 g) and 3-pyridinecarbaldehyde (4.1 g) in acetic acid (80 mL) was heated to reflux for 20 hours. After cooling to room temperature, the precipitate was collected by filtration, washed with methanol and dried to obtain the title compound as an acetic acid salt (10.5 g).

Reference example 16

4-chloro-2-(2-(3-pyridyl)vinyl)quinazoline

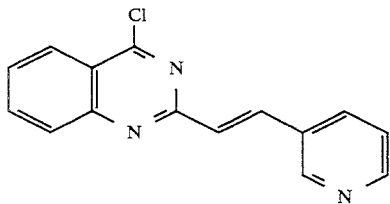

A suspension of the quinazolinone compound (2.9 g, prepared in Reference example 15) in thionyl chloride (25 mL) and a few drops of dimethylformamide was heated at reflux for three hours. The mixture was then concentrated, the concentrate poured into 150 mL portions of chloroform, dried over potassium carbonate and concentrated to obtain the title compound (1.1 g) as a red oil.

EXAMPLE 7

4-phenylmethylamino-2-(2-(3-pyridyl)vinyl)quinazoline

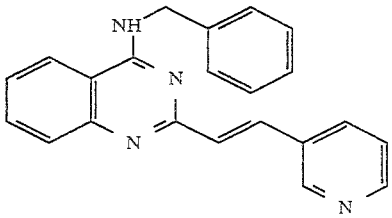

The title compound having the following physical data, was obtained by the same procedure as Example 1, by using the 4-chloro compound prepared in Reference example 16 and phenylmethylamine. The product was purified by column chromatography.

mp: 178°–179° C. NMR (CDCl3): δ 4.96 (d, 2H), 6.11 (broad, 1H), 7.30–7.55 (m, 8H), 7.70–7.81 (m, 2H), 7.99 (d, 1H), 8.34 (s, 1H), 8.36–8.45 (m, 1H), 8.55–8.58 (dd, 1H), 8.90–8.91 (d, 1H). IR (KBr): ν 3300 (m), 1577 (s), 1528 (s), 1434 (m), 1378 (s), 763 (m), 699 (m) cm$^{-1}$.

EXAMPLE 8

6-ethoxycarbonyl-4-phenylmethylamino-2-(1-imidazolyl)-5,6,7,8-tetrahydroquinazoline and its salt

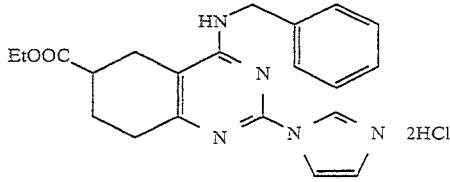

To 349 mg (1.0 mmol) of a compound prepared in example 6(t) dissolved in 20 mL of tetrahydrofuran was added 0.4 mL of thionyl chloride. Initially, a white precipitate formed, but gradually all dissolved. After stirring for 15 minutes, 20 mL of ethanol was added. After stirring an additional 15 minutes, the mixture was concentrated, the concentrate triturated in ether and collected. The solid was found to be very hygroscopic, was taken up in chloroform, treated with potassium carbonate solution, separated, dried over anhydrous magnesium sulfate and concentrated. Obtained 278 mg (0.7 mmol, 73% yield) of the desired product as a white solid (free base).

(free base)
mp: 196°–198° C. NMR (DMSO-$d_6$): δ 1.30 (t, 3H), 1.90 (m, 1H), 2.28 (m, 1H), 2.60 (m, 2H), 2.82 (m, 3H), 4,23 (q, 2H), 4.77 (d, 2H), 5.12 (m, 1H), 7.10 (s, 1H), 7.37 (m, 5H), 7.83 (s, 1H), 8.54 (s, 1H). IR (KBr): 3245 (w), 1725 (ms), 1605 (s), 1532 (w), 1473 (m), 1426 (m), 1333 (w) cm$^{-1}$.

To a suspension of 240 mg (0.64 mmol) of the compound prepared above in 5 mL of ethanol was added 2 mL of ~10% HCl in methanol. All the material gradually dissolved. After ten minutes, the mixture was concentrated in vacuo, triturated in ether and filtered to obtain 229 mg (0.51 mmol) of the desired product.

(2HCl salt)
mp: 158°–161° C. NMR (200 MHz, DMSO-d6)δ: 1.22 (t, 3H), 1.87(m, 1H), 2.14 (m, 1H), 2.55–3.00 (m, 5H), 7.79 (s, 1H), 8.23 (s, 1H), 9.77 (s, 1H). IR (KBr)ν: 3225, 1718, 1642, 1612, 1518, 1393 cm⁻¹.

EXAMPLE 8(a)

6-ethylaminocarbonyl-4-phenylmethylamino-2-(1-imidazolyl)-5,6,7,8-tetrahydroquinazoline dihydrochloride

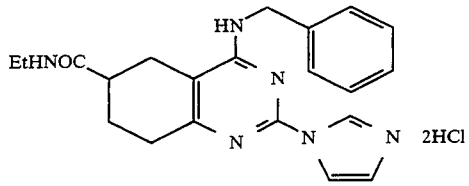

By the same procedure as described in example 8, by using ethylamine instead of ethanol, the title compound having the following physical data was given.

mp: 147° C., (dec.)
NMR (200 MHz, DMSO-d6) δ: 1.04 (q, 3H), 1.65–2.06 (m, 2H), 2.50–2.80 (m, 5H), 3.10 (m, 2H), 4.72 (m, 2H), 7.18–7.48 (m, 5H), 7.81 (s, 1H), 8.05 (t, 1H), 8.18 (M, 1H), 8.24 (m, 1H), 9.82 (s, 1H). IR (KBr) ν: 3265–2580, 2365, 1653, 1 61 3, 1576, 1540, 1449, 1390, 1352, 1144, 1060, 750, 701,624 cm⁻¹.

EXAMPLE 9

4-phenylmethylamino-2-(1-imidazolyl)quinazoline dimethanesulfonate

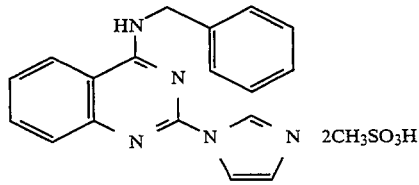

By the same procedure as described in Reference example 13 and 14 and example 5 and 6, by using methanesulfonic acid instead of hydrochloric acid, the title compound and the following compounds having the following physical data were given.

mp: 140°–143° C. NMR (200 MHz, DMSO-d6) δ: 2.38 (s, 6H), 4.95 (m, 2H), 7.20–8.00 (m, 9H), 8.40–8.53 (m, 2H), 9.64 (t, 1H), 10.00 (s, 1H).

EXAMPLE 9(a)

6,7-dimethoxy-4-phenylmethylamino-2-(1-imidazolyl)-quinazoline dimethanesulfonate

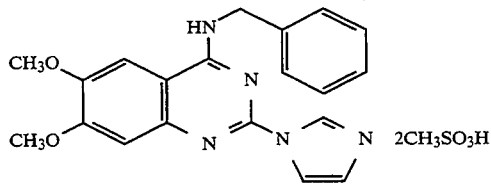

mp: 205° C., (dec.) NMR (200 MHz, DMSO-d6) δ: 2.36 (s, 6H), 3.92 (s, 3H), 3.95 (s, 3H), 4.95 (m, 2H), 7.18 (d, 1H), 7.21–7.53 (m, 5H), 7.82 (s, 1H), 7.87 (m, 1H), 8.39 (m, 1H), 9.21 (t, 1H), 9.94 (m, 1H).

EXAMPLE 9(b)

4-(3,4-dimethoxyphenylmethyl)amino-2-(1-imidazolyl)-quinazoline 1.5 methanesulfonate

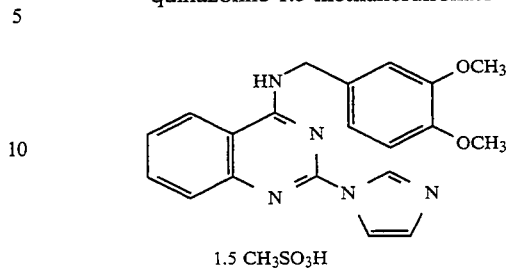

mp: 163°–173° C. NMR (200 MHz, DMSO-d6) δ: 2.34 (s, 4H), 3.73 (d, 6H), 4.88 (d, 2H), 6.02 (d, 1H), 7.03 (d, 1H), 7.16 (s, 1H), 7.62 (t, 1H), 7.78 (d, 1H), 7.89 (m, 2H), 8.45 (d, 1H), 8.48 (s, 1H), 9.55 (t, 1H), 10.02 (s, 1H).

EXAMPLE 9(c)

4-(2-phenoxyethyl)amino-2-(1-imidazolyl)quinazoline dimethanesulfonate

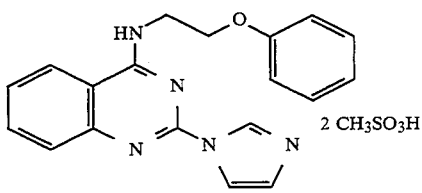

mp: 144°–161° C. NMR (200 MHz, DMSO-d6) δ: 2.39 (s, 6H), 4.12 (q, 2H), 4.34 (t, 2H), 6.97 (m, 3H), 7.28 (t, 2H), 7.63 (m, 1H), 7.80 (s, 1H), 7.89 (m, 2H), 8.45 (m, 2H), 9.30 (m, 2H), 9.97 (s, 1H). IR (KBr) ν: 3700–2800 (broad), 1636 (s), 1211 (s) cm⁻¹.

EXAMPLE 10

6-carboxy-4-phenylmethylamino-2-(1-imidazolyl)-5,6,7,8-tetrahydroquinazoline sodium salt

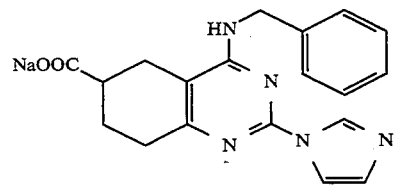

A solution of 200 mg (0.57 mmol) of a compound prepared in example 6(t) dissolved in 25 mL of tetrahydrofuran was filtered to remove dark insoluble material present. To the filtrate was added 0.25 mL (0.62 mmol) of 2.5N sodium hydroxide solution. Some precipitate formed. The mixture was concentrated and pumped in vacuum. The concentrate was triturated in tetrahydrofuran and ether and filtered. The solid was washed with ether and filtered to obtain 190 mg (0.51 mmol) of the desired product as a white solid.

mp: 240° C., (dec.) NMR (200 MHz, DMSO-d6)δ:1.50–1.82 (m, 2H), 1.88–2.35 (m, 2H), 2.59 (m, 3H), 4.62 (s, 2H), 6.98 (s, 1H), 7.12–7.48 (m, 5H), 7.73 (s, 1H), 7.86 (m, 1H), 8.33 (s, 1H).

By the same procedure as described in example 10, the compound having the following physical data was given.

EXAMPLE 10(a)

6-carboxy-4-phenylmethylamino-2-(1-imidazolyl)-quinazoline sodium salt

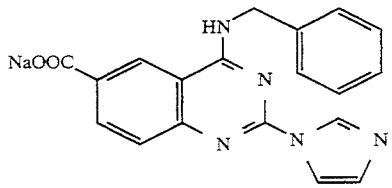

mp: >280° C.
NMR (200 MHz, DMSO-d6) δ: 4.48 (d, 2H), 6.99 (s, 1H), 7.25 (m, 1H), 7.33 (m, 4H), 7.40 (d, 1H), 7.78 (s, 1H), 7.97 (dd, 1H), 8.46 (s, 1H), 8.57 (d, 1H), 9.11 (br, 1H). IR (KBr)ν: 3500–3100 (br), 1620, 1559, 1472, 1399, 1307, 1224, 1056, 699 cm⁻¹.

Reference example 17

4-(1,1-dimethyl-2-methoxyethyl)amino-2-chloroquinazoline

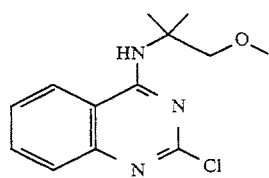

A mixture of 2,4-dichloroquinazoline (995 mg, 5 mmol), triethylamine (0.7 ml, 5 mmol) and 1,1-dimethyl-2-methoxyethylamine (30 mL, 0.5M methanol sol., 15 mmol) was stood at room temperature for 1 week. The reaction mixture was concentrated and partitioned between ethyl acetate and water. Organic layer was washed with water and brine, dried over MgSO₄ and concentrated. The residue was purified on 50 g of silica gel column eluting with 50% ethyl acetate in hexane to obtain the title compound (176 mg) as a white solid.

NMR (CDCl₃): δ 1.60 (s, 6H), 3.46 (s, 3H), 3.56 (s, 2H), 7.38–7.80 (m, 4H).

EXAMPLE 11

4-(1,1-dimethyl-2-methoxyethyl)amino-2-(1-imidazolyl)quinazoline dihydrochloride

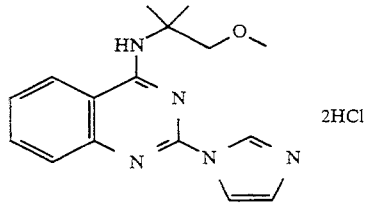

A mixture of the compound prepared in Reference example 17 (165 mg, 0.62 mmol), imidazole (169 mg, 2.48 mmol) and phenol (0.7 g) was heated at 150 ° C for 40 min. After cooling, the reaction mixture was diluted with ethyl acetate, and washed with 1N KOH and brine, and dried over MgSO₄. The filtrate was concentrated to leave a viscous oil, which was purified on 8 g of silica gel column eluting with 50% ethyl acetate in hexane to obtain the title compound (165 mg, 90% yield) as a colorless amorphous.

(free base)
NMR (CDCl₃): δ 1.65 (s, 6H), 3.48 (s, 3H), 3.58 (s, 2H), 6.32 (broad, 1H), 7.17 (s, 1H), 7.40 (m, 1H), 7.62–7.81 (m, 3H), 7.97 (s, 1H), 8.67 (s, 1H).

To a solution of the compound above (160 mg, 0.54 mmol) in methanol (2mL) was added excess HCl-methanol solution (2mL). After stirring for 20 min at room temperature, the reaction mixture was concentrated. Excess HCl was evaporated with methanol (×3) to leave a white solid. Trituration with ether gave HCl salt (185 mg) as a white powder.

(HCl salt)
mp: 223°–225° C. NMR (200 MHz, DMSO-d6) δ: 9.80 (s, 1H), 8.59 (m, 1H), 8.34 (m, 1H), 7.84–7.96 (m, 3H), 7.78 (m, 1H), 7.60 (m, 1H), 3.78 (s, 2H), 3.29 (s, 3H), 1.57 (s, 6H). IR (KBr)ν: 1633, 1610, 1562, 1520, 1474, 1397, 1108, 754 cm⁻¹.

By the same procedure as described in Reference example 17 and example 11, by using corresponding amine, the compounds having the following physical data were given.

EXAMPLE 11 (a)

6-methoxy-4-(2-methoxyethyl)amino-2-(1-imidazolyl)-quinazoline dihydrochloride

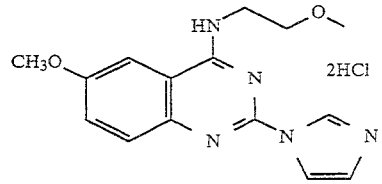

(HCl salt)
mp: 169° C., (dec.) NMR (200 MHz, DMSO-d6) δ: 3.31, (s, 3H), 3.69, (t, 2H), 3.92 (s, 3H), 7.50 (dd, 1H), 7.88 (s, 1H), 7.97 (s, 1H), 8.42 (s, 1H), 9.21 (t, 1H), 9.99 (s, 1H). IR (KBr) ν: 3380, 3200–2700, 1636, 1608, 1569, 1385, 1264, 1111, 101 8 cm⁻¹.

EXAMPLE 11 (b)

6-chloro-4-(2-methoxyethyl)amino-2-(1-imidazolyl)-quinazoline dihydrochloride

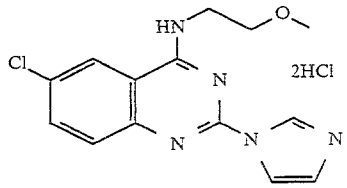

mp: 200°–206° C., (browning) NMR (200 MHz, DMSO-d6) δ: 10.0 (s, 1H), 9.32 (m, 1H), 8.68 (s, 1H), 8.43 (s, 1H), 7.85–7.96 (m, 2H), 7.77 (d, 1H), 3.90 (m, 2H), 3.66 (m, 2H), 3.32 (s, 3H). IR (KBr) ν: 1606, 1578, 1555, 1524, 1498, 1445, 1395, 1354, 1320, 1108, 1012, 876, 829 cm⁻¹.

EXAMPLE 11 (c)

4-(3-ethoxypropyl)amino-2-(1-imidazolyl)quinazoline dihydrochloride

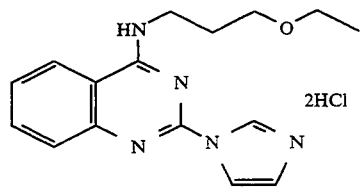

mp: 170°–180° C. NMR (200 MHz, DMSO-d6)δ: 1.11 (t, 3H), 1.95 (qt, 2H), 3.38–3.54 (m, 4H), 3.74 (m, 2H), 7.60 (t, 1H), 7.78 (d, 1H), 7.90 (m, 2H), 8.44 (m, 2H), 9.22 (t, 1H), 9.97 (s, 1H). IR (KBr)ν:2870–3950, 1624, 1556, 1473, 1400, 1311, 1090 cm⁻¹.

EXAMPLE 11 (d)

6-nitro-4-(2-methoxyethyl)amino-2-(1-imidazolyl)-quinazoline hydrochloride

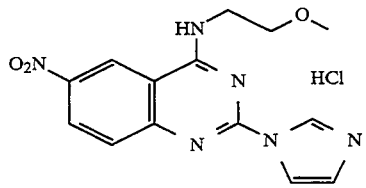

mp: 211° C., (dec.) NMR (200 MHz, DMSO-d6) δ: 3.33 (s, 3H), 3.66–3.71 (m, 2H), 3.90–3.95 (m, 2H), 7.84 (m, 1H), 7.88 (d, 1H), 8.44 (m, 1H), 8.59 (m, 1H), 9.54 (m, 1H), 9.85 (bt, 1 H), 9.94 (d, 1H). IR (KBr) ν: 3430, 3220–2585, 1606, 1579, 1523, 1499, 1444, 1404, 1336, 1259, 1147, 1115, 1091, 1059, 1016, 847, 825 cm⁻¹.

EXAMPLE 11(e)

6-chloro-4-(2-(2-hydroxyethoxy)ethyl)amino-2-(1-imidazolyl)quinazoline dihydrochloride

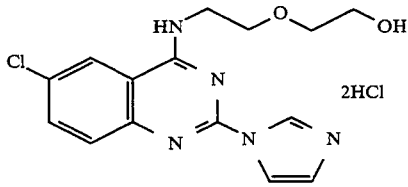

mp: 184°–186° C. NMR (200 MHz, DMSO-d6) δ: 3.51 (s, 4H), 3.75–3.77 (m, 2H), 3.85–3.90 (m, 2H), 7.76 (d, 1H), 7.84 (m, 1H), 7.91 (dd, 1H), 8.40 (t, 1H), 8.67 (m, 1H), 9.30 (bt, 1H), 9.92 (m, 1H). IR (KBr) ν:3320, 3175–2825, 1602, 1574, 1497, 1439, 1398, 1343, 1118cm⁻¹.

EXAMPLE 11 (f)

6,7-dimethoxy-4-(2-methoxyethyl)amino-2-(1-imidazolyl)quinazoline dihydrochloride

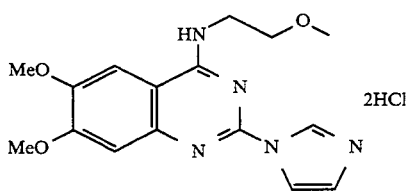

mp: 249°–251° C. NMR (200 MHz, DMSO-d6) δ: 3.32 (s, 3H), 3.65 (t, 2H), 3.85 (m, 2H), 3.94 (s, 6H), 7.16 (s, 1H), 7.88 (s, 2H), 8.39 (s, 1H), 8.92 (t, 1H), 9.95 (s, 1H). IR (KBr)ν: 3425-2365, 1642, 1603, 1573, 1511, 1481, 1456, 1386, 1287, 1240, 1156, 1132, 1109, 1021, 988, 876,770 cm⁻¹.

EXAMPLE 12

6-chloro-4-(2-ethoxyethyl)amino-2-(3-pyridyl)quinazoline and its salt

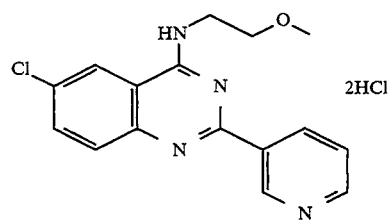

A solution of 2-(3-pyridyl)-4,6-dichloroquinazoline (1.0 g, 3.2 mmol, prepared in Reference example 5(b)) and 2-methoxyethylamine (0.53 g, 7.0 mmol) in 50 mL of ethanol was heated to reflux overnight. The solution was concentrated, taken up in chloroform and water. After some mixing, the water layer was found to be slightly acidic and was basified with sodium carbonate. The mixture was then agitated and separated. The organic layer was dried over potassium carbonate and concentrated. The concentrate was purified on silica gel column with 5% methanol in chloroform as eluent. The product obtained was combined with additional material filtered from the aqueous layer. Obtained a total of 0.35 g (1.1 mmol) of the title compound.

(free base)

mp: 21 0°–21 2° C. NMR (200 MHz, DMSO-d6): <5 3.32 (s, 3H), 3.67 (t, 2H), 3.87 (qd, 2H), 7.53 (m, 1H), 7.82 (s, 2H), 8.48 (s, 1H), 8.71 (m, 3H), 9.59 (s, 1H) IR (KBr): ν 3250 (m), 1692 (s), 1535 (s), 1430 (w), 1412 (w), 1366 (m), 1140 (m), 823 (m) cm⁻¹.

To a mixture of 0.35 g (1.1 mmol) of the compound prepared above in 5 mL of methanol was added 0.5 mL of 10% HCl in methanol. The solution was concentrated to 1 mL, triturated in ether, filtered and dried under vacuum. Obtained 0.33 g (0.85 mmol) of the hydrochloride.

(HCl salt)

mp: 190° C., (dec.) NMR (200 MHz, DMSO-d6) δ: 3.32 (s, 3H), 3.71 (t, 2H), 3.94 (m, 2H), 8.01 (m, 2H), 8.12 (d, 1H), 8.75 (m, 1H), 9.01 (d, 1H), 9.20 (d, 1H), 9.66 (s, 1H). IR (KBr)ν: 3425, 2500–3050, 1633, 1610, 1569, 1387, 1107 cm⁻¹.

By the same procedure as described in Example 12, by using corresponding amine, the compounds having the following physical data was given.

EXAMPLE 12(a)

6-chloro-4-(2-dimethylaminoethyl)amino-2-(3-pyridyl)-quinazoline trihydrochloride

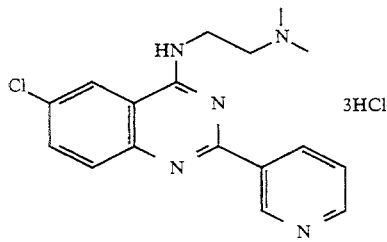

mp =179° C. (dec.). NMR (200 MHz, D$_2$O): δ 2.96 (s, 6H), 3.51 (t, 2H), 4.02 (t, 2H), 7.57 (m, 1H), 7.70 (m, 3H), 8.68 (m, 2H), 9.14 (s, 1H). IR (KBr) ν: 3405, 3215, 2545, 1577, 1536, 1474, 1437, 1396, 1360, 827, 721 cm$^{-1}$.

EXAMPLE 13

6-hydroxy-4-phenylmethylamino-2-(1-imidazolyl)-quinazoline and its salt

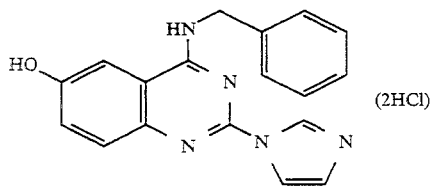

To 66 mg (0.2 mmol) of the compound prepared in Example 6(g) in 1 mL of acetic acid was added 0.8 mL (7 mmol) of 48% HBr in water. The mixture was heated below reflux for 23 hours then heated to full reflux for four hours. After cooling to room temperature, 15 mL of water was added to the solution and the precipitate was filtered and dried under vacuum. The material was purified on a preparative silica gel plate with 10% methanol in chloroform. Obtained 13 mg (41 gmol) of the desired product as a solid.

(free base)
mp: 230° C., (dec.) NMR (200 MHz, CD3OD) δ: 4.86 (s, 2H), 7.05 (s, 1H), 7.15–7.38 (m, 4H), 7.40–7.50 (m, 3H), 7.58–7.66 (m, 1H), 7.92 (s, 1H), 8.52 (s, 1H). IR (KBr)ν: 3370, 3030, 2365, 1749, 1710, 1653, 1596, 1559, 1523, 1488, 1465, 1407, 1376, 1291, 1244, 1162, 1098, 1060, 911,831 cm$^{-1}$.

By the same procedure as described in Example 12, the hydrochloride having the following physical data was given.

(2HCl salt)
mp: 155° C., (dec.)
NMR (200 MHz, DMSO-d6) δ: 4.92 (m, 2H), 7.22–7.77 (m, 8H), 7.86 (s, 1H), 8.38 (s, 1H), 9.36 (m, 1H), 9.94 (s, 1H). IR (KBr)ν: 3395–2640, 2365, 1734, 1628, 1607, 1567, 1542, 1473, 1361, 1353, 1289, 1260, 1201, 1107, 1015, 835, 753, 702 cm$^{-1}$.

EXAMPLE 14

4-(2-(2-hydroxyethoxy)ethyl)amino-6-methylsulfinyl-2-(1-imidazolyl)quinazoline and its dihydrochloride

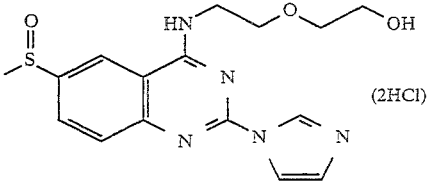

To 1.38 g of the compound prepared in example 6(mm) dissolved in 10 mL of acetic acid was added 4 mL of 30% hydrogen peroxide. The reaction was monitored by TLC. After stirring for 1/2 hour, the mixture was poured into 15 g of 50% w/w sodium hydroxide and ice. The resulting mixture was extracted four times with chloroform, dried over anhydrous magnesium sulfate and concentrated. The concentrate was triturated in ether and collected to obtain 1.26 g of the desired product as a white solid.

To 400 mg of the compound prepared above in 10 ml of methanol was added 1 mL of 10% HCl in methanol. After ten minutes, the mixture was concentrated, triturated in ether and the solid collected. Obtained 441 mg of the desired product as a dihyrochloride salt.

(free base)
mp: 144°–147° C. NMR (200 MHz, DMSO-d6): d 2.85(s, 3H), 3.50(m, 4H), 3.70-3.90(m, 4H), 4.59(m, 1H), 7.11 (s, 1H), 7.82(m, 1H), 7.98(s, 1H), 8.02(m, 1H), 8.e2(s, 1H), 8.67(m, 1H), a. 14(t, 1H).

(2HCl salt)
mp: 190°–192° C. NMR (200 MHz, DMSO-d6): d 2.89(s, 3H), 3.51(s, 4H), 3.76(m, 2H), 3.89(m, 2H), 7.90(m, 2H), 8.14(m, 1H), 8.45(m, 1H), 8.89(m, 1H), 9.62(t, 1H), 10.10(m, 1H).

By the same procedure as described in Example 14, by using corresponding thioether, the compounds having the following physical data were given.

EXAMPLE 14(a)

4-(2-methoxyethyl)amino-6-methylsulfinyl-2-(1-imidazolyl)quinazoline and its dihydrochloride

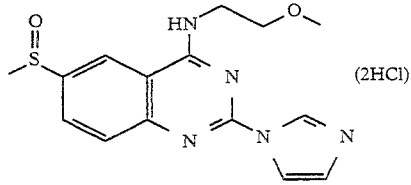

(free base)
mp: 170°–173° C. NMR (200 MHz, DMSO-d6): d 2.85(s, 3H), 3.32(s, 3H), 3.69(m, 2H), 3.83(m, 2H), 7.12(s, 1H), 7.77-8.10(m, 2H), 7.98(s, 1H), 8.68(s, 1H), 9.16(s, 1H).

(2HCl salt)
mp: 191°–193° C. NMR (200 MHz, DMSO-d6): d 2.89(s, 3H), 3.31(s, 3H), 3.67(m, 2H), 3.89(m, 2H), 7.86-8.18(m, 3H), 8.45(m, 1H), 8.89(m, 1H), 9.63(t, 1H), 10.05(m, 1

EXAMPLE 14(b)

6-methylsulfinyl-4-phenylmethylamino-2-(1-imidazolyl)quinazoline dihydrochloride

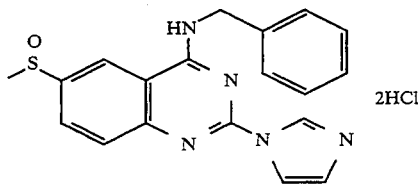

2HCl mp: 167°–170° C. NMR (200 MHz, DMSO-d6): δ 2.87(s, 3H), 4.96(d, 2H), 7.32–7.53(m, 5H), 7.87(d, 1H), 7.93(s, 1H), 8.15(s, 1H), 8.42(s, 1H), 8.86(s, 1H),10.01(s, 1H), 10.10(t, 1H). IR (KBr): ν 3370(w), 3220(w), 3060(m), 2825(m), 1617(s), 1577(s), 1541(m), 1497(w), 1444(m), 1396(s), 1355(w), 1014(m), a36(w), 788(w), 702(w) cm$^{-1}$.

EXAMPLE 15

4-(2-methoxyethyl)amino-6-methylsulfonyl-2-(1-imidazolyl)quinazoline hydrochloride

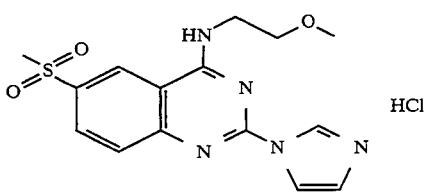

HCl

To 0.63 g of the compound prepared in example 6(11) (free base) in 7 mL of acetic acid was added 3 ml of 30% hydrogen peroxide solution and the mixture was stirred at room temperature for 17 hour. The mixture was then poured into a solution of 50% w/w sodium hydroxide in ice. The resulting mixture was extracted twice with 70 mL portions of chloroform, dried over anhydrous magnesium sulfate and concentrated. The concentrate was triturated in ether and the solid collected to obtain 0.36 g of the desired product as a white powder.

To a suspension of 300 mg of the compound above in 15 mL of methanol was added 1 mL of 10% HCl in methanol. The mixture become clear then a precipitate formed. The mixture was concentrated to approximately 5 mL, diluted with ether and filtered to obtain 319 mg of the desired product as a white solid.

(free base)
mp: 241°–243° C.
(HCl salt)
mp: 226°–228° C. NMR (200 MHz, DMSO-d6): d 3.32(s, 3H), 3.36(s, 3H), 3.67(m, 2H), 3.93(m, 2H), 7.81(s, 1H), 7.93(m, 1H), 8.30(m, 1H), 8.42(s, 1H), 9.16(m, 1H), 9.72(t, 1H), 9.92(s, 1 H).

By the same procedure as described in Example 15, the below compound having the following physical data was given.

EXAMPLE 15(a)

6-methylsulfonyl-4-phenylmethylamino-2-(1-imidazolyl)quinazoline hydrochloride

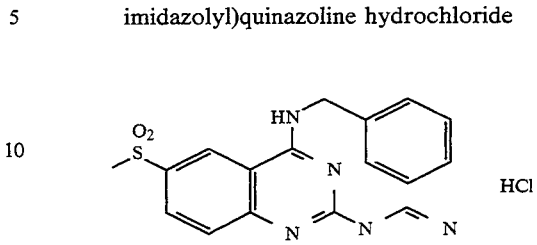

HCl mp: 125°–130° C. NMR (200 MHz, DMSO-d6): δ 3.34(s, 3H), 4.97(d, 2H), 7.31–7.50(m, 5H), 7.85(s, 1H), 7.93(d, 1H), 8.32(d, 1H), a.44(s, 1H), 9.14(s, 1H), 9.9a(s, 1H), 10.12(t, 1H). IR (KBr): ν 3230(s), 3040(s), 2705(s), 2370(m), 1616(s), 1572(s), 1524(s), 1497(m), 1399(s), 1326(s), 1258(m), 1204(w), 1147(s), 1008(m), 834(w), 783(s), 730(w), 620(w), 535(m) cm$^{-1}$.

EXAMPLE 16

6-hydroxymethyl-4-phenylmethylamino-2-(1-imidazolyl)quinazoline

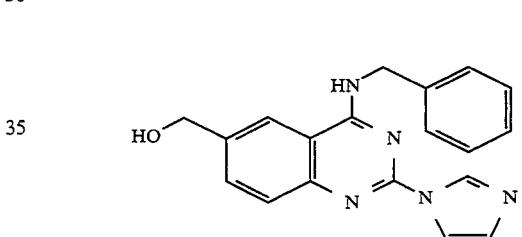

To a suspension of 0.68 g of the compound prepared in example 5(e) in 50 mL of anhydrous tetrahydrofuran was added 2 mL of 2M lithium borohydride in tetrahydrofuran. The reaction mixture was heated at reflux for two days. The mixture was then concentrated, diluted with water and the basic solution was acidified with 1N hydrochloric acid. The resulting solution was then basified with potassium carbonate, filtered and the solid washed with water and allowed to dry. The solid material was purified on silica gel column eluting with 5% methanol in chloroform. Obtained 85 mg of the desired product.

mp: 173° C. (dec.). NMR (200 MHz, DMSO-d6): δ 4.67(d, 1H), 4.90(d, 1H), 5.47(t, 1H), 7.23(m, 1H), 7.25–7.51(m, 5H), 7.67–7.85(m, 2H), 8.12(m, 1H), 8.34(m, 1H), 8.9 (s, H), 9.5 (t, H). IR (KBr): ν 3445(mw), 2365(mw), 1599(s), 1559(m), 1505(mw), 1444(w), 1410(m), 1340(w), 1161(w), 1073(w)cm$^{-1}$.

By the same procedure as described in Example 16, the below compounds having the following physical data were given.

EXAMPLE 16(a)

4-(2-methoxyethyl)amino-6-hydroxymethyl-2-(1-imidazolyl)quinazoline

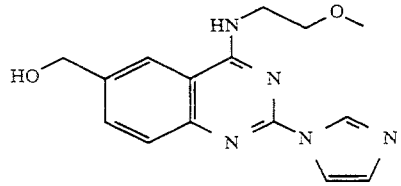

mp: 165°–168° C. NMR (200 MHz, DMSO-d6): S 3.35(s, 3H), 3.68(t, 2H), 3.80(t, 2H), 4.65(d, 2H), 5.45(t, 1H), 7.12(s, 1H), 7.68(m, 2H), 7.99(s, 1H), 8.27(s, 1H), 8.62(s, 1H), 8.83(s, 1H). IR (KBr): ν 3370(m), 1597(s), 1559(m), 1474(m), 1409(m) cm$^{-1}$.

EXAMPLE 16(b)

4-[2-(2-hydroxyethoxy)ethyl]amino-6-hydroxymethyl-2-(1-imidazolyl)quinazoline

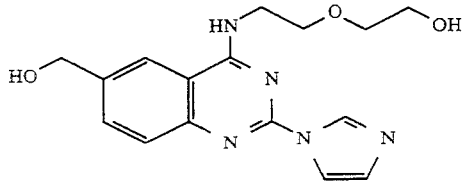

mp: 183° C. NMR (200 MHz, DMSO-d6): δ 3.48(s, 4H), 3.76(m, 4H), 4.62(d, 2H), 5.44(t, 1H), 7.10(s, 1H), 7.62–7.80(m, 2H), 7.97(s, 1H), 8.27(s, 1H), 8.60(s, 1H), 8.82(bs, 1H). IR (KBr): ν 3311 (row), 3156(w), 1597(s), 1558(w), 1487(w), 1438(w), 1408(ms), 1052(w) cm$^{-1}$.

Reference example 18

6-iodoquinazolin-2,4-dione

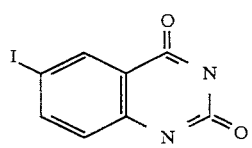

To a mixture of 25.36 g of 2-amino-5-iodobenzoic acid in 250 ml of water and 90 mL of THF was added 7.40 g of glacial acetic acid and stirred at room temperature. Then was added 7.82 g of potassium cyanate in water dropwise. Left to overnight. Added another 5.47 g of potassium cyanate. Stirred overnight. A total of 160 g of NaOH pellets were added portionwise, keeping the mixture cool in ice-water bath. The mixture was stirred at room temperature overnight. The mixture was cooled in a refrigerator and the precipitate filtered through a sintered glass funnel. The precipitate was then dissolved in water and acidified with 4N HCl. The precipitate was collected by filtration. The solid was dried in a vacuum oven to yield 25.44 g of the title compound.

Reference example 19

6-(2-triethylsilylethylnyl)quinazolin-2,4-dione

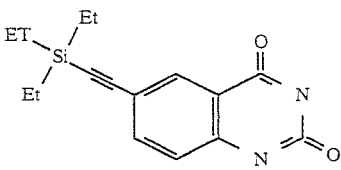

In a flusk was placed 0.544 g of triphenylphosphine, 0.184 g of palladium chloride, and 5 mL of diethylamine. Stirred under a nitrogen atmosphere. To the resulting yellow mixture was added 75 mL of diethylamine, followed by 10.02 g of the compound prepared in reference example 18. Then added 19.8 mg of cuprous iodine to the purple suspension. Turned gray after 10 minutes. After 0.5 hr added 5.36 g of triethylsilyl acetylene and stirred at room temperature. After 3 hrs the solution turned purple. After another 1.5 hrs. the solution turned brown. Left to stir overnight. Monitored reaction by TLC. Removed the solvent under reduced pressure at 40° C. and added water. Acidified with 1N—HCl. The precipitated solid was collected by filtration, washed with water, and dried in a vacuum oven. The solid was then passed through a silica gel column, eluting with THF. After drying yielded 10.22 g of the title compound having the following physical data.

NMR (200 MHz, DMSO-d6): δ 0.65(dd, 6H), 0.93(dd, 9H), 7.15(d, 1H), 7.69(d, 1H), 11.38(br, 2H).

Reference example 20

2,4-dichloro-6-(2-triethylsilylethylnyl)quinazoline

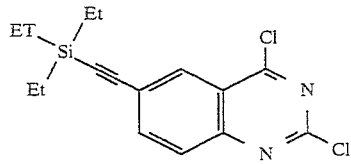

To 5.09 g of the compound prepared in reference example 19, was added 25 mL of POCl$_3$ and warmed. Then added 1.03 g of N,N-dimethylaniline and heated to reflux. After 3.5 hrs, the excess POCl3 was removed under reduced pressure and the residue diluted in chloroform and poured slowly over ice. The organic layer was collected and the solvent removed. The residue was passed through a silica gel column using 20% EtOAc/hexane as a solvent. Yielded 1.4 g of the product having the following physical data.

NMR (200 MHz, CDCl$_3$): δ 0.72(m, 6H), 1.00(m, 9H), 7.98(d, 1H), 8.33(s, 1H).

Reference example 21

2-chloro-4-(2-methoxyethyl)amino-6-(2-triethylsilylethynyl)quinazoline

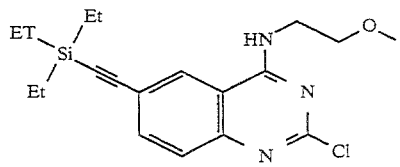

To 1.4 g of the compound prepared in reference example 20 in 20 mL of chloroform was added 2-methoxyethylamine and stirred at room temperature for 1.5 hr. Then added 4.2 ml of 1N-NaOH and heated to reflux. Left to reflux overnight. The solvent was removed under reduced pressure and the residue taken up in chloroform and water. The organic layer was collected and dried over anhydrous potassium carbonate. Removal of solvent under reduced pressure yielded 1.44 g of the title compound.

NMR (200 MHz, CDCl$_3$): δ 0.73 (m, 6H), 1.07(m, 9H), 3.45(s, 3H), 3.69(t, 2H), 3.88(dd, 2H), 6.32(br, 1H), 7.69(d, 1H), 7.78(dd, 1H), 7.80(s, 1H).

EXAMPLE 17

2-(1-imidazolyl)-4-(2-methoxyethyl)amino-6-(2-triethylsilylethynyl)quinazoline

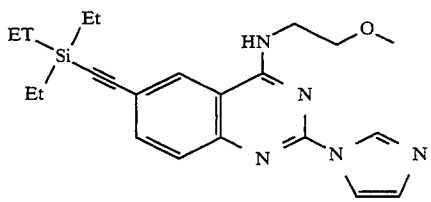

To 1.32 g of the compound prepared in reference example 21 in 5 mL of ethanol was added excess imidazole (0.93 g) and heated in an oil bath to 115° C. After 1.5 hrs. removed from heat and diluted in chloroform and washed with 1N-NaOH, collected the organic layer and washed with water. The organic layer was extracted and dried over anhydrous potassium carbonate. Removal or solvent yielded 1.33 g of the title compound.

mp: 158°–160° C. NMR (200 MHz, DMSO-d6): δ 0.70(q, 6H), 1.05(t, 9H), 3.30(s, 3H), 3.64(t, 2H), 3.81(dd, 2H), 7.10(s, 1H), 7.65(d, 1H), 7.78(dd, 1H), 7.96(s, 1H), 8.01(s, 1H), 8.60(s, 1H), a.95(br, 1H).

By the same procedures as described in reference examples 18, 19, 20 and 21, and example 17, the following compound was obtained.

EXAMPLE 17(a)

2-(1-imidazolyl)-4-[2-(2-hydroxyethoxy)ethyl]amino-6-(2-triisopropylsilylethynyl)quinazoline

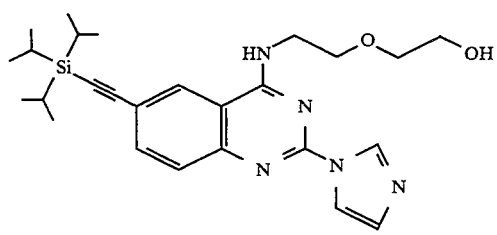

mp: 155°–156° C.; NMR (200 MHz, CDCl$_3$): δ 1.09 (s, 3H), 1.16 (s, 18H), 2.28 (br, 1H), 3.70 (m, 2H), 3.84 (dd, 4H), 3.95 (t, 2H), 6.65 (br, 1H), 7.14 (s, 1H), 7.68 (d, 1H), 7.75 (dd, 1H), 7.87 (s, 1H), 7.93 (s, 1H), 8.65 (s, 1H).

EXAMPLE 17(b)

2-(1-imidazolyl)-4-phenylmethylamino-6-(2-triisopropylsilylethynyl) quinazoline

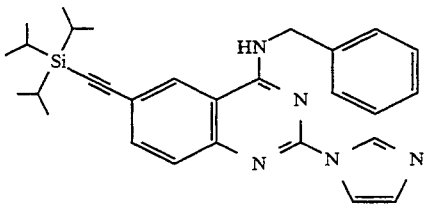

(200 MHz, DMSO-d6): δ 1.13 (s, 21H), 4.85 (s, 2H), 7.08 (m, 1H), 7.21–7.40 (m, 3H), 7.46 (m, 2H), 7.65–7.82 (m, 2H), 7.93 (m, 1H), 8.55 (m, 2H), 9.50 (s, 1H).

EXAMPLE 18

6-ethynyl-4-(2-methoxyethyl)amino-2-(1-imidazolyl)-quinazoline

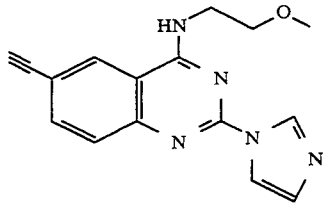

To 1.35 g of the compound prepared in example 17 in 20 mL of THF was added 3.3 mL of tetrabutylammonium fluoride (1M in THF). Stirred at room temperature for 1.5 hrs. The excess THF was removed under reduced pressure and the residue taken up in chloroform and water. The insoluble precipitate was collected by filtration. Yielded 0.83 g of the title compound.

NMR (200 MHz, DMSO-d6): δ. 3.33(s, 3H), 3.66(m, 2H), 3.83(m, 2H), 4.34(s, 1H), 7.11(s, 1H), 7.65(d, 1H), 7.82(dd, 1H), 7.96(s, 1H), 8.57(d, 1H), 8.62(s, 1H), 8.90(broad, 1H). IR (KBr): ν 3290(s), 2945(m), 1606(s), 1559(s), 1451(s), 1352(s), 1106(s), 835(s) cm$^{-1}$.

By the same procedure as described in example 18, the following compound was given.

EXAMPLE 18(a)

2-(1-imidazolyl)-4-[2-(2-hydroxyethoxy)ethyl]amino-6-ethynylquinazoline and its salt

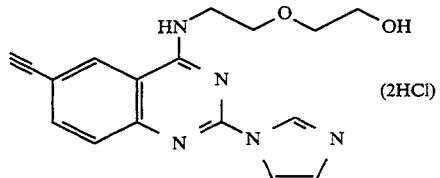

(free base)
mp: 166°–167° C.; NMR (200 MHz, DMSO-d6): δ 3.50 (s, 4H), 3.78 (m, 4H), 4.35 (s, 1H), 4.59 (t, 1H), 7.10 (s, 1H), 7.65 (d, 1H), 7.80 (dd, 1H), 7.97 (s, 1H), 8.55 (d, 1H). 8.61 (s, 1H), 8.90 (br, 1H).

(HCl salt)
mp: 178° C.; NMR (200 MHz, DMSO-d6): δ 3.51 (s, 4H), 3.74 (m, 2H), 3.87 (m, 2H), 4.44 (s, 1H), 7.73 (d, 1H), 7.82 (s, 1H), 7.90 (d, 1H), 8.40 (s, 1H), 8.67 (s, 1H), 9.25(br, 1H), 9.88 (s, H).

EXAMPLE 18(b)

2-(1-imidazolyl)-4-phenylmethylamino-6-ethynyl-quinazoline dihydrochloride

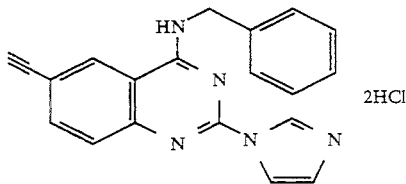

mp: 203°–205° C. NMR (200 MHz, DMSO-d6): δ 4.43(s, 1H), 4.97(d, 2H), 7.33(m, 3H), 7.50(d, 2H), 7.55(d, 1H), 7.85(m, 2H), 8.40(s, 1H), 8.74(s, 1H), 9.88(t, 1H), 9.97(s, 1H). IR (KBr) :ν 3400, 3235, 1598, 1396, 899, 842, 762, 620 cm$^{-1}$.

EXAMPLE 19

6-acetyl-4-(2-methoxyethyl)amino-2-(1-imidazolyl)-quinazoline

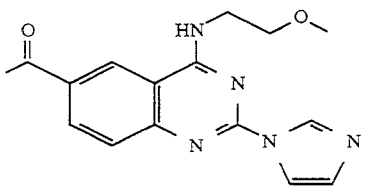

To 0.541 g of the compound prepared in example 18 in 10 ml of acetic acid was added 0.7 mL of 10% H2SO4 and 0.10 g of mercury II sulfate and heated to reflux. After 2 hours removed from heat and basified. The yellow precipitate was filtered. The solid was washed with THF. Removed the solvent under reduced pressure and titrated the residue in 50% ether/pentane. The solid was collected by filtration. Yielded 0.063 g of the desired product.

mp: 208°–210° C. NMR (200 MHz, CDCl3): δ 2.64(s, 3H), 3.49(s, 3H), 3.79(t, 2H), 3.95(q, 2H), 7.00(broad, 1H), 7.16(t, 1H), 7.74(d, 1H), 7.95(t, 1H), 8.17(dd, 1H), 8.42(d, 1H), 8.67(t, 1H).

By the same procedure as described in Example 19, the below compound having the following physical data was given.

EXAMPLE 19(a)

4-[2-(2-hydroxyethoxy)ethyl]amino-6-acetyl-2-(1-imidazolyl)quinazoline

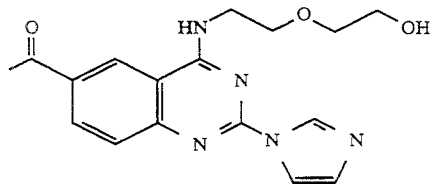

mp: 164°–166° C. NMR (200 MHz, DMSO-d6): δ 2.69(s, 3H), 3.51 (s, 4H), 3.76(m, 2H), 3.84(t, 2H), 4.60(br, 1H), 7.12(s, 1H), 7.73(d, 1H), 7.98(s, 1H), 8.27(dd, 1H), 8.64(s, 1H), 9.00(s, 1H), 9.25(br, 1H). IR (KBr):ν 3350, 1671, 1623, 1593, 1558, 1474, 1447, 1418, 1365, 1307, 1270, 1111, 1051 cm$^{-1}$.

Formulation Example 1

The following components were admixed in conventional method and punched out to obtain 100 tablets each containing 50 mg of active ingredient.

| | |
|---|---|
| 6-ethynyl-4-(2-methoxyethyl)amino-2-(1-imidazolyl)quinazoline | 5.0 g |
| cellulose calcium glycolate (disintegrating agent) | 0.2 g |
| magnesium stearate (lubricating agent) | 0.1 g |
| micro crystalline cellulose | 4.7 g |

What is claimed is:
1. A quinazoline derivative of the formula(I):

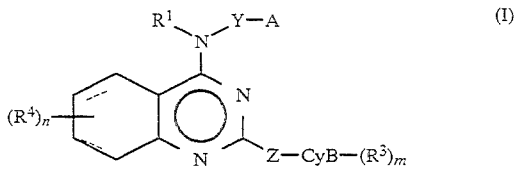

wherein R$^1$ is hydrogen or C1–4 alkyl;
Y is single bond or C1–6 alkylene;
A is
 (i) —CyA—(R$^2$)$_l$,
 (ii) —O—R$^0$ or —S(O)$_p$—R$^0$,
in which R$^0$ is R$^{0A}$ or R$^{0B}$;
R$^{0A}$ is —CyA—(R$^2$)l;
R$^{0B}$ is hydrogen or C1–4 alkyl;
p is 0–2;
CyA is
 (1) 3–7 membered, saturated or unsaturated, monocyclic carbocyclic ring,
 (2) 7-membered, unsaturated or partially saturated, monocyclic hetero ring containing as hetero atoms, one nitrogen atom, one nitrogen and one oxygen atoms, two nitrogen and one oxygen atoms, or one nitrogen and two oxygen atoms,
 (3) 6-membered, unsaturated or partially saturated, monocyclic hetero ring containing as hetero atoms, one nitrogen and one oxygen atoms, two nitrogen and one oxygen atoms, or one nitrogen and two oxygen atoms,
 (4) 6-membered, unsaturated or partially saturated, monocyclic hetero ring containing as a hetero atom, one nitrogen atom,
 (5) 4- or 5-membered, unsaturated or partially saturated, monocyclic hetero ring containing as hetero atoms, one nitrogen atom, one nitrogen and one oxygen atoms, two nitrogen and one oxygen atoms, or one nitrogen and two oxygen atoms,
 (6) 4–7 membered, unsaturated or partially saturated, monocyclic hetero ring containing as hetero atoms, one or two sulfur atoms or
 (7) 4–7 membered, unsaturated or partially or fully saturated, monocyclic hetero ring containing as hetero atoms, one or two oxygen atom;
R$^2$ is R$^{2A}$ or R$^{2B}$;
R$^{2A}$ is (1) —NR$^{6A}$R$^{7A}$, in which R$^{6A}$ and R$^{7A}$ independently are hydrogen or C1–4 alkyl (with the proviso that R$^{6A}$ and R$^{7A}$ are not hydrogen at same time), (2) —SO$_2$NR$^6$R$^7$, in which R$^6$ and R$^7$ independently are hydrogen or C1–4 alkyl, (3) trifluoromethyl or (4) trifluoromethoxy;

$R^{2B}$ is (1) hydrogen, (2) C1–4 alkyl, (3) C1–4 alkoxy, (4) —COOR$^5$, in which R$^5$ is hydrogen or C1–4 alkyl, (5) halogen, (6) nitro or (7) —NR$^{GB}$R$^{7B}$, in which R$^{6B}$ and R$^{7B}$ are hydrogen;

Z is $Z^A$ or $Z^B$;

$Z^A$ is methylene, ethylene, vinylene or ethynylene;

$Z^B$ is single bond;

CyB is
(1) 7-membered, unsaturated or partially saturated, monocyclic hetero ring containing as hetero atoms, one, two or three nitrogen atoms,
(2) 6-membered, unsaturated or partially saturated, monocyclic hetero ring containing as hetero atoms, two or three nitrogen atoms,
(3) 6-membered, unsaturated or partially saturated, monocyclic hetero ring containing as a hetero atom, one nitrogen atom,
(4) 4- or 5-membered, unsaturated or partially saturated, monocyclic hetero ring containing as hetero atoms, one, two or three nitrogen atoms, or
(5) 4–7 membered, unsaturated or partially saturated, monocyclic hetero ring containing as hetero atoms, one or two oxygen atoms, or one or two sulfur atoms;

$R^3$ is hydrogen, C1–4 alkyl, C1–4 alkoxy, halogen or trifluoromethyl;

$R^4$ is $R^{4A}$ or $R^{4B}$;

$R^{4A}$ is (1) —NHSO$_2$R$^{11}$, in which R$^{11}$ is C1–4 alkyl, (2) SO$_2$NR$^9$R$^{10}$, in which $R^9$ is hydrogen, C1–4 alkyl or phenyl(C1–4 alkyl) and R$^{10}$ is hydrogen or C1–4 alkyl, (3) —OCOR$^{11}$, in which R$^{11}$ is as hereinbefore defined, (4) hydroxy, (5) —SO$_2$N=CHNR$^{12}$R$^{13}$ in which R$^{12}$ is hydrogen or C1–4 alkyl and R$^{13}$ is C1–4 alkyl, (6) —CONR$^{14}$R$^{15}$ in which R$^{14}$ is hydrogen or C1–4 alkyl and R$^{15}$ is C1–4 alkyl or phenyl(C1–4 alkyl), (7) ethynyl, (8) tri(C1–4 alkyl)silylethynyl or (9) acetyl;

$R^{4B}$ is (1) hydrogen, (2) C1–4 alkyl, (3) C1–4 alkoxy, (4) —COOR$^8$, in which R$^8$ is hydrogen or C1–4 alkyl, (5) —NR$^9$R$^{10}$, in which R$^9$ and R$^{10}$ are as hereinbefore defined, (6) —NHCOR$^{11}$, in which R$^{11}$ is as hereinbefore defined, (7) halogen, (8) trifluoromethyl, (9) nitro, (10) cyano, (11) C1–4 alkylthio, (12) C1–4 alkylsulfinyl, (13) C1–4 alkylsulfonyl, (14) hydroxymethyl, and l, m and n independently are 1 or 2; with the proviso that
(1) the group of the formula: —CyA—(R$^2$)$_l$ does not represent a cyclopentyl and trifluoromethylphenyl group when Y is a single bond, that
(2) a CyB ring does not bond to Z through a nitrogen atom in the CyB ring when Z is vinylene or ethynylene, that
(3) a CyB ring is not pyridine or thiophene when CyA is a ring of CyA—(7) that
(4) Y is not a single bond, when A is (ii) —O—R$^0$ or —S(O)$_p$—R$^0$ and that
(5) A is not —CyA—(R$^2$B)l and —OR$^{0B}$, when Z is $Z^B$ and R$^4$ is $R^{4B}$; or pharmaceutically acceptable acid addition salts thereof, pharmaceutically acceptable salts thereof, or hydrates thereof.

2. A compound according to claim 1, which is compound of the formula [I-(A)];

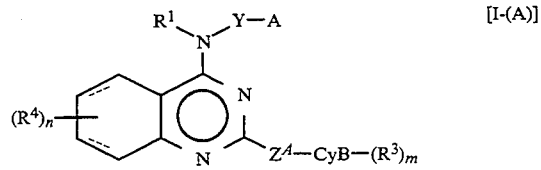

(wherein $Z^A$ is methylene, ethylene, vinylene or ethynylene.

3. A compound according to claim 1, which is compound of the formula [I(B)];

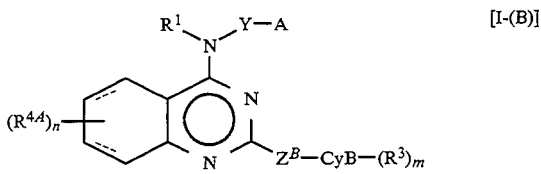

(wherein $Z^B$ is single bond; $R^{4A}$ is —NHSO$_2$R$^{11}$, SO$_2$NR$^9$R$^{10}$, —OCOR$^{11}$, hydroxy, —SO$_2$N=CHNR$^{12}$R$^{13}$, —CONR$^{14}$R$^{15}$, ethynyl, tri(C1–4 alkyl)silylethynyl or acetyl.

4. A compound according to claim 1, which is compound of the formula [I-(C)];

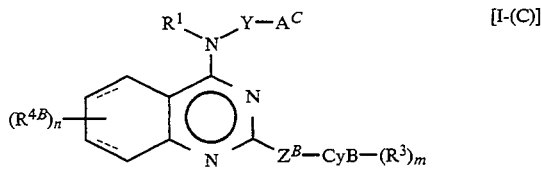

(wherein $Z^B$ is single bond; $A^C$ is —CyA—(R$^2$A)l, —O—R$^{0A}$ or —S(O)p—R$^0$; R$^{0A}$ is —CyA—(R$^2$)l; R$^0$ is hydrogen, C1–4 alkyl or—CyA—(R$^2$)l; p is 0–2; R$^{2A}$ is —NR$^{GA}$R$^{7A}$ (with the proviso that R$^{6A}$ and R$^{7A}$ are not hydrogen at same time), —SO$_2$NR$^6$R$^7$, trifluoromethyl or trifluoromethoxy; R$^{4B}$ is hydrogen, C1–4 alkyl, C1–4 alkoxy, —COOR$^8$, —NR$^9$R$^{10}$, —NHCOR$^{11}$, halogen, trifluoromethyl, nitro, cyano, C1–4 alkylthio, C1–4 alkylsulfinyl, C1–4 alkylsulfonyl, hydroxymethyl.

5. A compound according to claim 1, wherein CyB is 7-membered, unsaturated or partially saturated, monocyclic hetero ring containing as hetero atoms, one, two or three nitrogen atoms.

6. A compound according to claim 1, wherein CyB is 6-membered, unsaturated or partially saturated, monocyclic hetero ring containing as hetero atoms, two or three nitrogen atoms.

7. A compound according to claim 1, wherein CyB is 6-membered, unsaturated or partially saturated, monocyclic hetero ring containing as hetero atoms, one nitrogen atom.

8. A compound according to claim 1, wherein CyB is 4- or 5-membered, unsaturated or partially saturated, monocyclic hetero ring containing as hetero atoms, one, two or three nitrogen atoms.

9. A compound according to claim 1, wherein CyB is 4–7 membered, unsaturated or partially saturated, monocyclic hetero ring containing as hetero atoms, one or two oxygen atoms, or one or two sulfur atoms.

10. A compound according to claim 1, wherein CyB is pyridine ring.

11. A compound according to claim 1, wherein CyB is imidazole ring.

12. A compound according to claim 1, wherein CyB is triazole or pyrrole ring.

13. A compound according to claim 1, wherein CyB is furan or thiophene ring.

14. A compound according to claim 1, wherein A is OH, —O—C1-4 alkyl, —S(O)p—H, or —S(O)p—C1-4 alkyl.

15. A compound according to claim 1, wherein A is —CyA—($R^2$)l, —O—CyA—($R^2$)l or —S(O)-p—CyA—($R^2$)l.

16. A compound according to claim 1, wherein Y is single bond.

17. A compound according to claim 1, wherein Y is methylene or ethylene.

18. A compound according to claim 1, wherein Z is single bond.

19. A compound according to claim 1, wherein Z is methylene.

20. A compound according to claim 2, which is:
4-phenylmethylamino-2-((1-imidazolyl)methyl)-quinazoline,
4-phenylmethylamino-2-((1-imidazolyl)methyl)-quinazoline,
6-chloro-4-phenylmethylamino-2-(1-imidazolylmethyl)quinazoline,
6-chloro-4-phenylamino-2-(1-imidazolylmethyl)-quinazoline,
6-chloro-4-(3-carboxyphenyl)amino-2-(1-imidazolylmethyl)quinazoline
or
4-phenylmethylamino-2-(2-(3-pyridyl)vinyl)quinazoline,
and pharmaceutically acceptable acid addition salts thereof, pharmaceutically acceptable salts thereof, or hydrates thereof.

21. A compound according to claim 3, which is:
6-dimethylaminosulfonyl-4-phenylmethylamino-2-(1-imidazolyl)quinazoline,
6-dimethylaminomethylideneaminosulfonyl-4-phenylmethylamino-2-(1-imidazolyl)quinazoline,
6-(phenylmethylaminosulfonyl)-4-phenylmethylamino-2-(1-imidazolyl)quinazoline,
6-phenylmethylaminocarbonyl-4-phenylmethylamino-2-(1-imidazolyl)quinazoline,
6-ethylaminocarbonyl-4-phenylmethylamino-2-(1-imidazolyl)-5,6,7,8-tetrahydroquinazoline,
6-hydroxy-4-phenylmethylamino-2-(1-imidazolyl)-quinazoline,
6-(1-i midazolyl)-4-(2-methoxyethyl)amino-6-(2-triethylsilylethynyl)quinazoline,
6-ethynyl-4-(2-methoxyethyl)amino-2-(1-imidazolyl)-quinazoline,
6-(1-imidazolyl)-4-phenylmethylamino-6-ethynyl-quinazoline or
6-acetyl-4-(2-methoxyethyl)amino-2-(1-imidazolyl)-quinazoline,
and pharmaceutically acceptable acid addition salts thereof, pharmaceutically acceptable salts thereof, or hydrates thereof.

22. A compound according to claim 4, which is:
4-(2-methylthioethyl)amino-6-methoxy-2-(1-imidazolyl)quinazoline,
4-(2-methylsulfinylethyl)amino-6-methoxy-2-(1-imidazolyl)quinazoline,
4-(2-methylsulfonylethyl)amino-6-methoxy-2-(1-imidazolyl)quinazoline,
4-(3-trifluoromethylphenylmethyl)amino-2-(3-pyridyl)quinazoline,
4-(4-(N,N-dimethylamino)phenylmethyl)amino-2-(3-pyridyl)quinazoline,
4-(4-sulfamoylphenylmethyl)amino-2-(3-pyridyl)-quinazoline,
4-(4-trifuloromethoxyphenylmethyl)amino-2-(1-imidazolyl)quinazoline,
4-(3-trifluoromethoxyphenylmethyl)amino-2-(1-imidazolyl)quinazoline,
4-(2-phenoxyethyl)amino-6-methoxy-2-(1-imidazolyl)quinazoline or
4-(2-phenoxyethyl)amino-2-(1-imidazolyl)quinazoline,
and pharmaceutically acceptable acid addition salts thereof, pharmaceutically acceptable salts thereof, or hydrates thereof.

23. A pharmaceutical composition for the treatment of mammals, which comprises, as active ingredient, an effective amount of a compound of the formula (I),

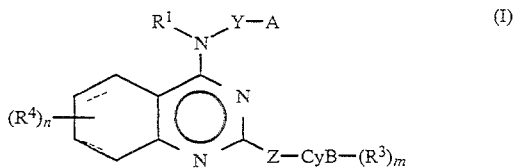

wherein Y, A, Z, CyB, $R^1$, $R^3$, $R^4$, m and n are as defined in claim 1,
pharmaceutically acceptable acid addition salts thereof, pharmaceutically acceptable salts thereof, or hydrates thereof and a pharmaceutically acceptable carrier.

24. A method for the treatment of mammals, to prevent or treat at least one disease selected from the group consisting of hypertension, heart failure, myocardial infarction, angina, atherosclerosis, cardiac edema, renal insufficiency, nephrotic edema, hepatic edema, asthma, bronchitis, dementia, immunodeficiency and pulmonary hypertension which method comprises administering to a patient an effective amount of a compound of the formula (I)

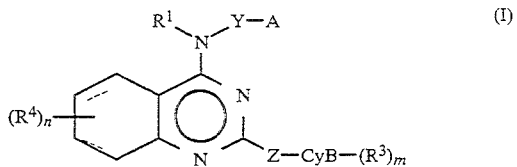

wherein Y, A, Z, CyB, $R^1$, $R^3$, $R^4$, m and n are as defined in claim 1,
pharmaceutically acceptable acid addition salts thereof, pharmaceutically acceptable salts thereof, or hydrates thereof.

25. The composition of claim 23 wherein the mammals are humans.

26. The method of claim 24 wherein the mammals are humans.

* * * * *